US012685528B2

(12) United States Patent
Erickson et al.

(10) Patent No.: US 12,685,528 B2
(45) Date of Patent: Jul. 21, 2026

(54) COMPRESSION STAPLE SYSTEMS AND METHODS

(71) Applicant: Vilex, LLC, McMinnville, TN (US)

(72) Inventors: Nathan W. Erickson, Collinston, UT (US); Tristan T. Spencer, Logan, UT (US); Brock L. Johnson, Draper, UT (US); Daniel J. Triplett, Huntsville, UT (US); Robert Willoughby, Heber, UT (US)

(73) Assignee: Vilex LLC, Park City, UT (US)

( * ) Notice: Subject to any disclaimer, the term of this patent is extended or adjusted under 35 U.S.C. 154(b) by 14 days.

(21) Appl. No.: 18/963,615

(22) Filed: Nov. 28, 2024

(65) Prior Publication Data

US 2026/0144541 A1     May 28, 2026

(51) Int. Cl.
| *A61B 17/064* | (2006.01) |
| *A61B 17/10* | (2006.01) |
| *A61B 17/17* | (2006.01) |

(52) U.S. Cl.
CPC .......... *A61B 17/0642* (2013.01); *A61B 17/10* (2013.01); *A61B 17/17* (2013.01)

(58) Field of Classification Search
CPC ...... A61B 17/17; A61B 17/10; A61B 17/0642
USPC ...................................................... 606/75, 99
See application file for complete search history.

(56) References Cited

U.S. PATENT DOCUMENTS

| 5,250,055 | A | * | 10/1993 | Moore | A61B 17/1778 |
| | | | | | 606/86 R |
| 5,507,801 | A | * | 4/1996 | Gisin | B25H 1/0078 |
| | | | | | 606/86 R |
| 7,635,367 | B2 | * | 12/2009 | Groiso | A61B 17/68 |
| | | | | | 606/75 |
| 7,699,203 | B2 | * | 4/2010 | McBride | A61B 17/064 |
| | | | | | 227/19 |
| 8,062,297 | B2 | * | 11/2011 | Faillace | A61B 17/0642 |
| | | | | | 606/75 |
| 8,235,995 | B2 | * | 8/2012 | Focht | A61B 17/068 |
| | | | | | 606/75 |
| 9,017,331 | B2 | * | 4/2015 | Fox | A61B 17/10 |
| | | | | | 606/75 |
| 9,220,609 | B2 | * | 12/2015 | Mueller | A61B 17/7059 |
| 9,839,458 | B2 | * | 12/2017 | Bouduban | A61F 2/0811 |
| 9,855,036 | B2 | * | 1/2018 | Palmer | A61B 17/7266 |
| 10,058,366 | B2 | | 8/2018 | Bouduban | |
| 10,105,134 | B2 | * | 10/2018 | Biedermann | A61B 17/083 |

(Continued)

*Primary Examiner* — Jessica Weiss
(74) *Attorney, Agent, or Firm* — David Meibos; Maywood IP Law

(57) ABSTRACT

A method for bone fixation using a compression staple system may include loading a compression staple including legs into an inserter, positioning a drill guide proximate first and second bone portions, using the drill guide and a drill to create a first and second hole in the first and second bone portions, wherein the first and second holes may be configured to receive the legs of the staple, using the drill guide and a first and second drill pin, driving the first and second drill pins into the first and second bone portions, withdrawing the drill guide and leaving the drill pins in the first and second bone portions, guiding the inserter and the staple over the first and second drill pins, inserting the legs of the staple into the first and second holes, actuating the inserter to release the staple, withdrawing the inserter, and removing the drill pins.

17 Claims, 33 Drawing Sheets

(56)  References Cited

U.S. PATENT DOCUMENTS

| | | | | |
|---|---|---|---|---|
| 10,117,647 | B2 | 11/2018 | Cheney | |
| 10,285,743 | B2 | 5/2019 | Bouduban | |
| 10,456,130 | B2 | 10/2019 | Cheney | |
| 10,456,131 | B2 | 10/2019 | Cheney | |
| 10,492,841 | B2 * | 12/2019 | Hartdegen | A61B 17/8085 |
| 10,779,816 | B2 * | 9/2020 | Goldstein | A61B 17/8095 |
| 10,820,902 | B2 | 11/2020 | Cheney | |
| 10,918,484 | B2 * | 2/2021 | Ellington | A61B 17/7059 |
| 10,987,101 | B2 * | 4/2021 | Ducharme | A61B 17/0642 |
| 11,051,804 | B2 * | 7/2021 | Gaston | A61B 17/1637 |
| 11,154,341 | B2 * | 10/2021 | Rogers | A61B 17/8061 |
| 11,179,149 | B2 * | 11/2021 | Hartdegen | A61B 17/68 |
| 11,202,626 | B2 * | 12/2021 | Hartdegen | A61B 17/808 |
| 11,246,588 | B2 * | 2/2022 | Maclure | A61B 17/0642 |
| 11,284,886 | B2 * | 3/2022 | Hartdegen | A61B 17/10 |
| 11,311,289 | B1 * | 4/2022 | Ritz | A61B 17/1615 |
| 11,864,753 | B2 * | 1/2024 | Hollis | A61B 17/0642 |
| 2005/0234467 | A1 * | 10/2005 | Rains | A61B 17/1735 606/96 |
| 2010/0125301 | A1 * | 5/2010 | Kinmon | A61B 17/1775 606/300 |
| 2012/0228355 | A1 * | 9/2012 | Combrowski | A61B 17/0642 227/175.1 |
| 2016/0030039 | A1 * | 2/2016 | Seavey | A61B 17/16 227/175.2 |
| 2017/0056083 | A1 * | 3/2017 | Fallin | A61B 17/8872 |
| 2017/0202552 | A1 * | 7/2017 | Coleman | A61B 17/0642 |
| 2017/0209193 | A1 * | 7/2017 | Hartdegen | A61B 17/8004 |
| 2017/0252036 | A1 * | 9/2017 | Palmer | A61B 17/866 |
| 2017/0296174 | A1 * | 10/2017 | Wahl | A61B 17/0682 |
| 2018/0344375 | A1 * | 12/2018 | Seavey | A61B 90/06 |
| 2021/0228364 | A1 * | 7/2021 | Cheney | A61B 17/10 |
| 2023/0060073 | A1 * | 2/2023 | Niver | A61B 17/0642 |
| 2023/0109346 | A1 * | 4/2023 | Carlo, III | A61B 17/17 606/96 |
| 2023/0255623 | A1 * | 8/2023 | Ritz | A61B 17/0642 606/75 |
| 2023/0270435 | A1 * | 8/2023 | Fox | A61B 17/0642 606/75 |
| 2023/0285116 | A1 * | 9/2023 | McGurk | A61B 17/1728 |

* cited by examiner

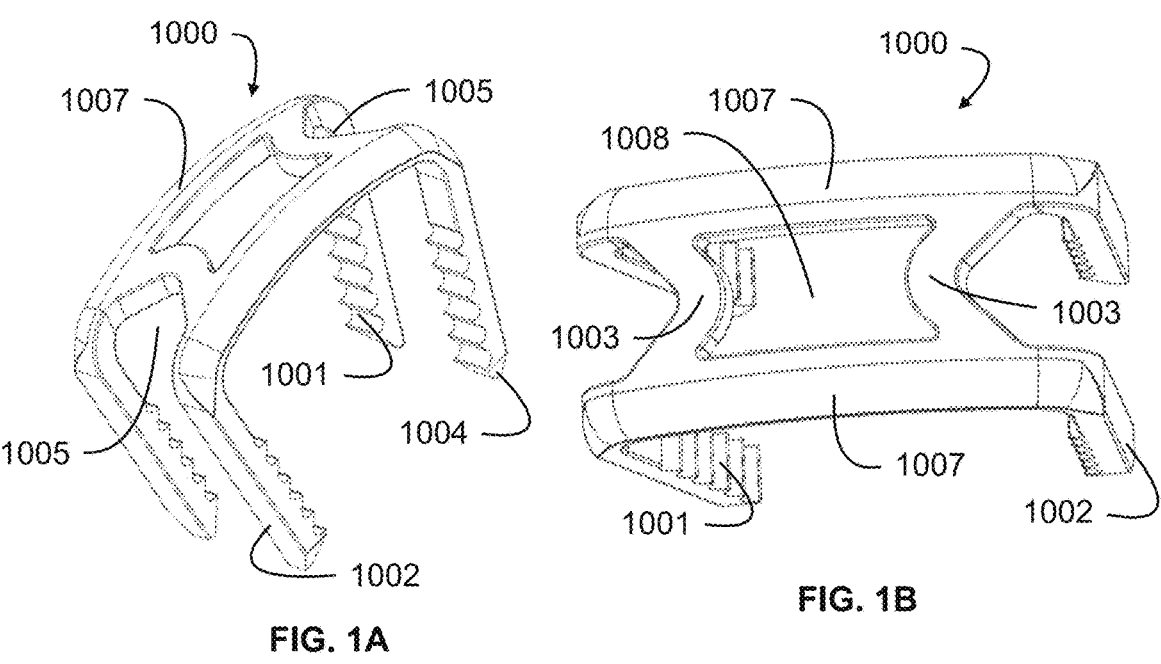
FIG. 1A
FIG. 1B
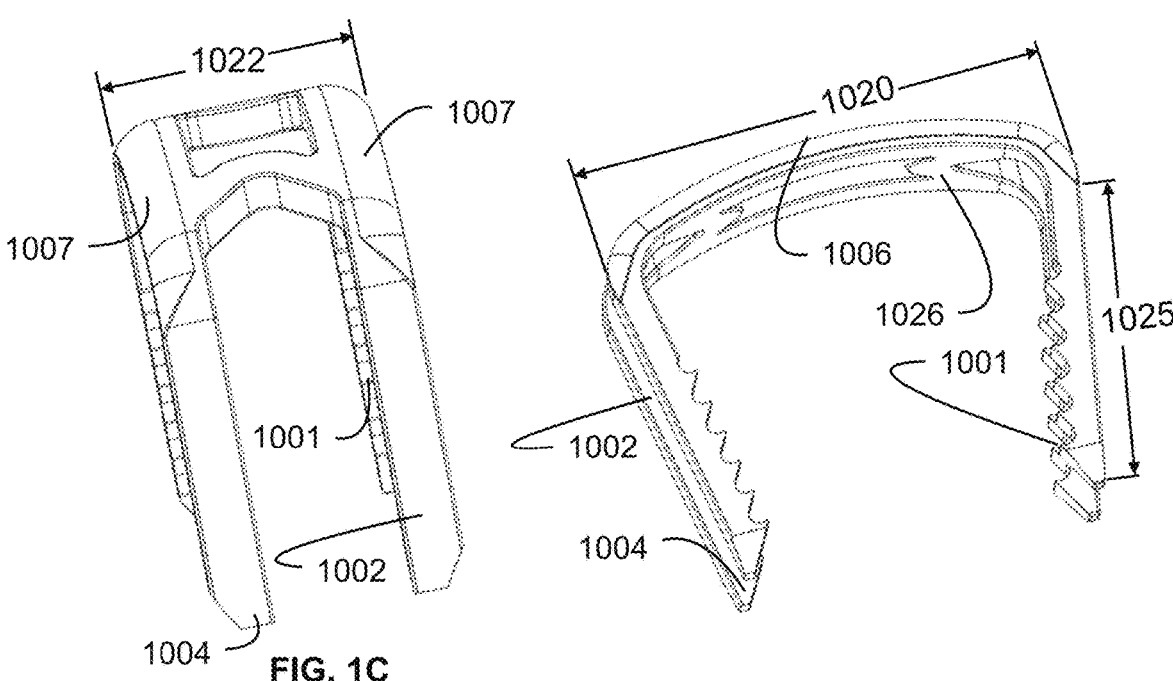
FIG. 1C
FIG. 1D

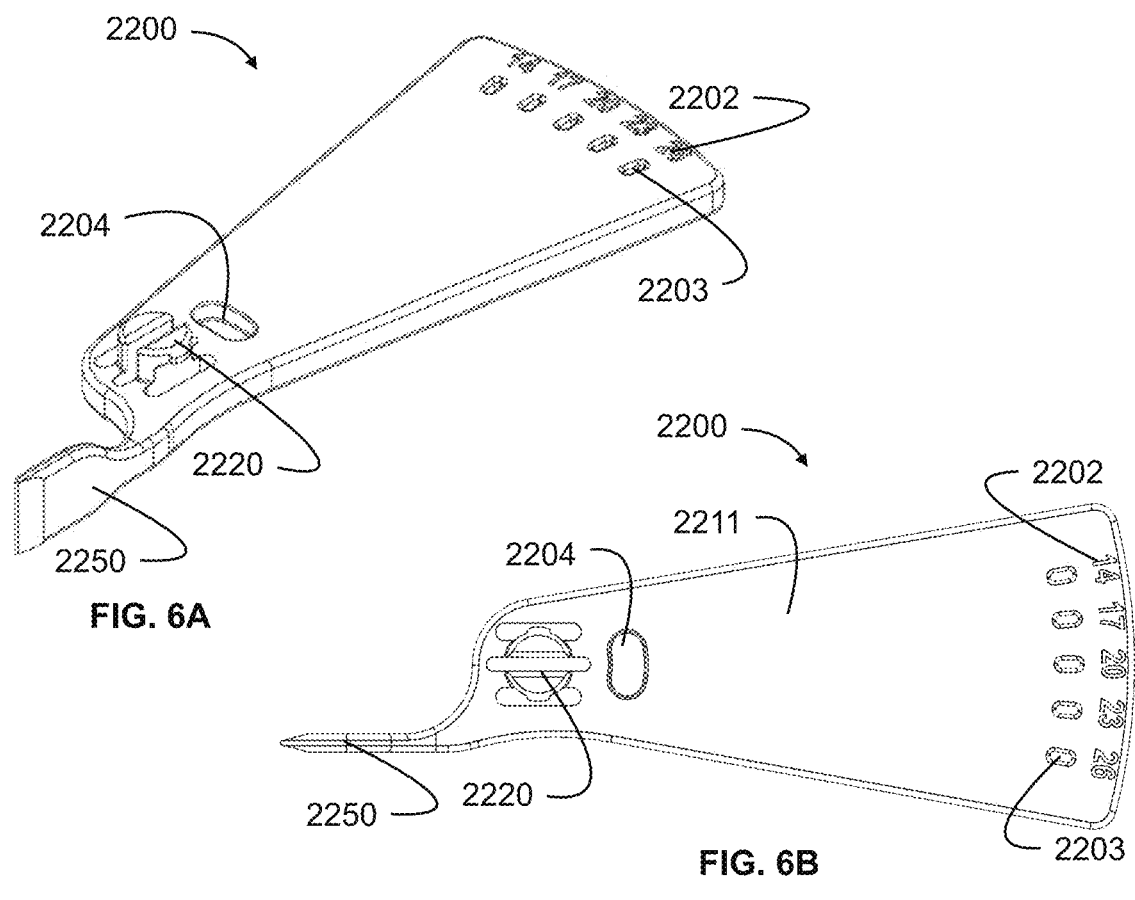
FIG. 6A
FIG. 6B
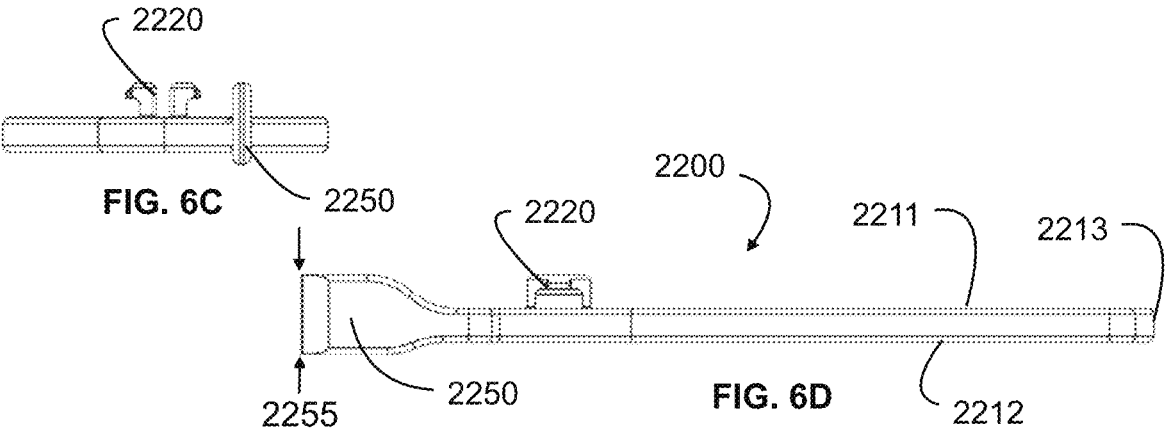
FIG. 6C
FIG. 6D

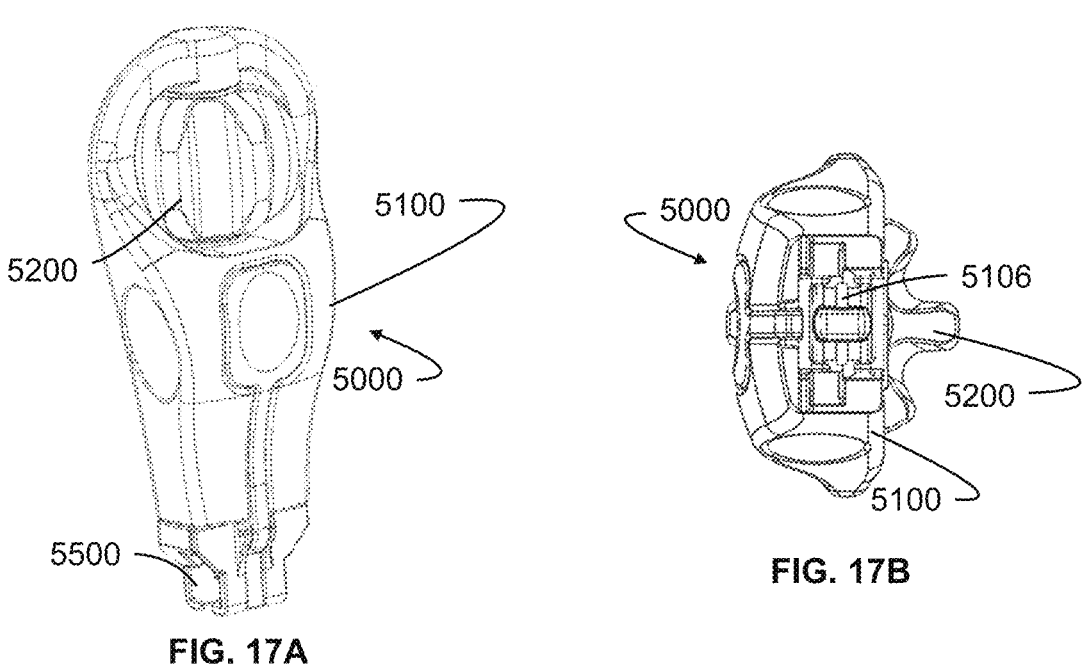
FIG. 17A
FIG. 17B
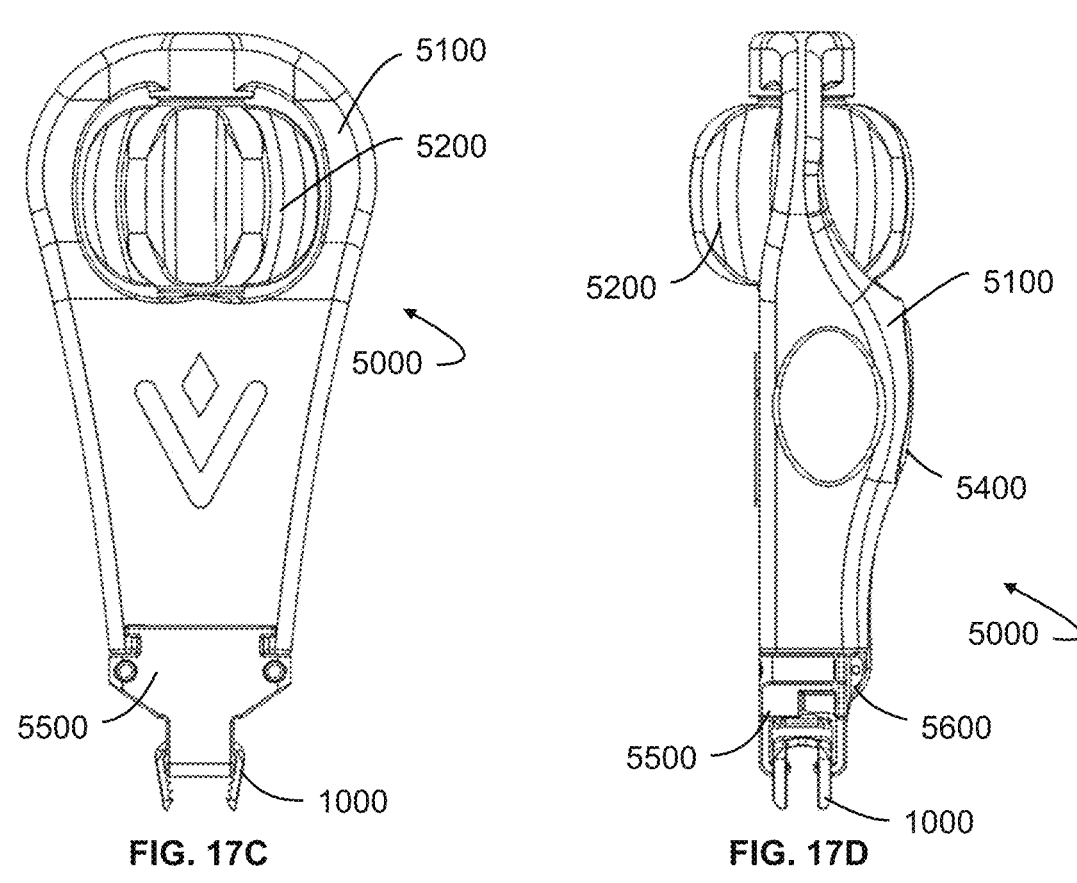
FIG. 17C
FIG. 17D

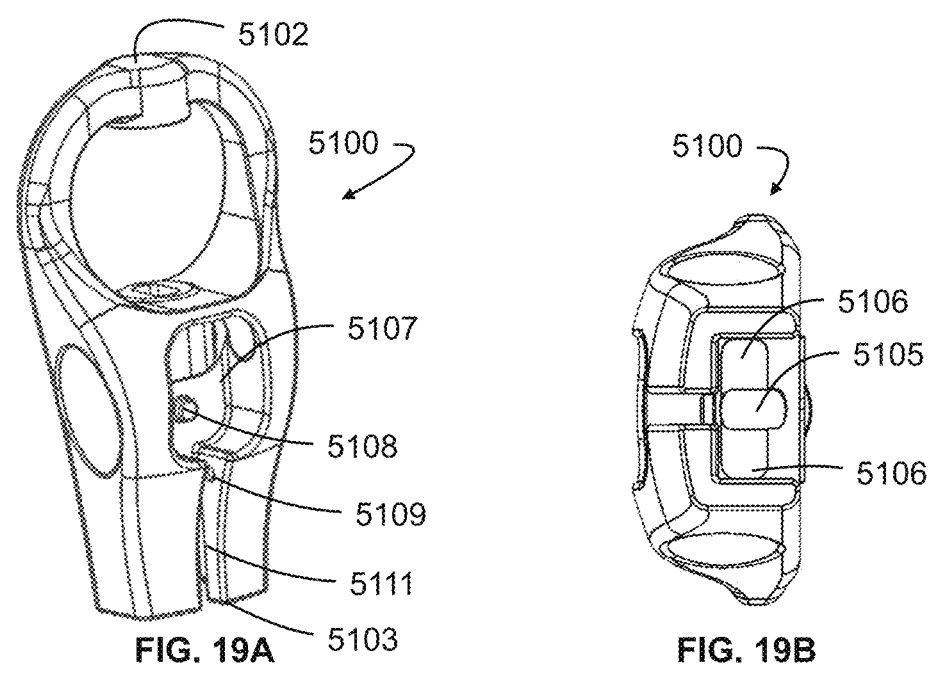
FIG. 19A
FIG. 19B
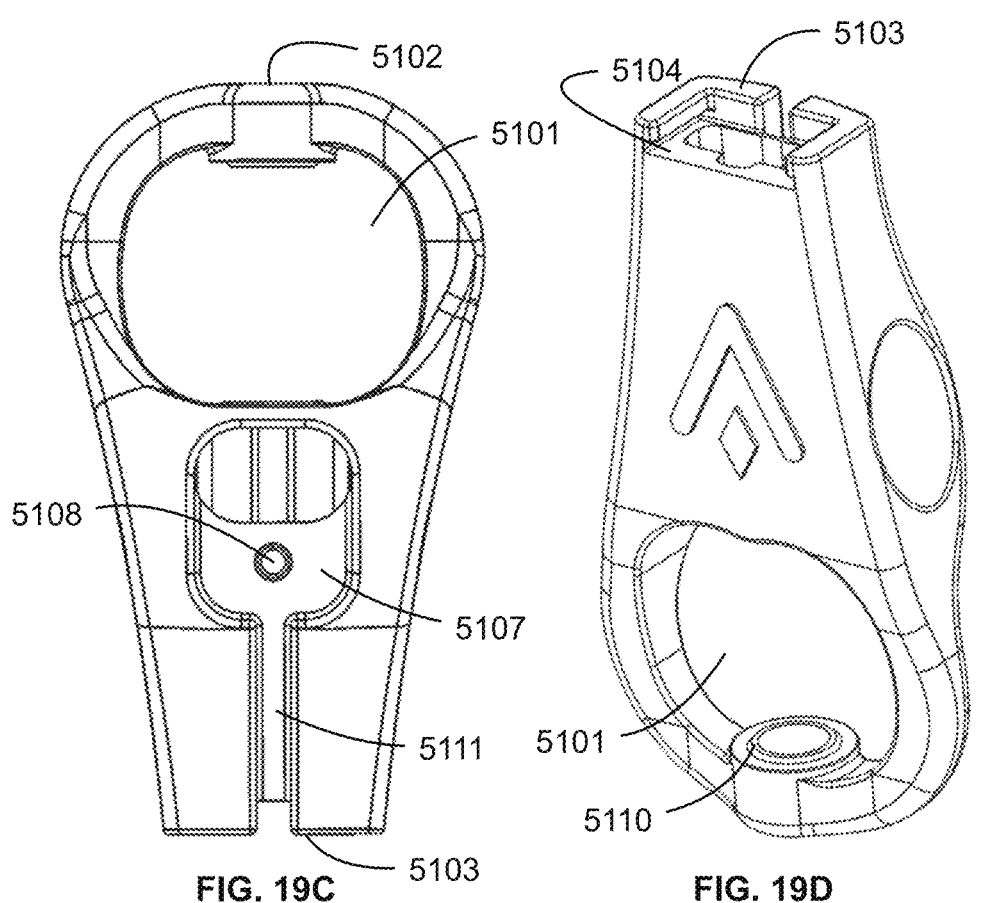
FIG. 19C
FIG. 19D

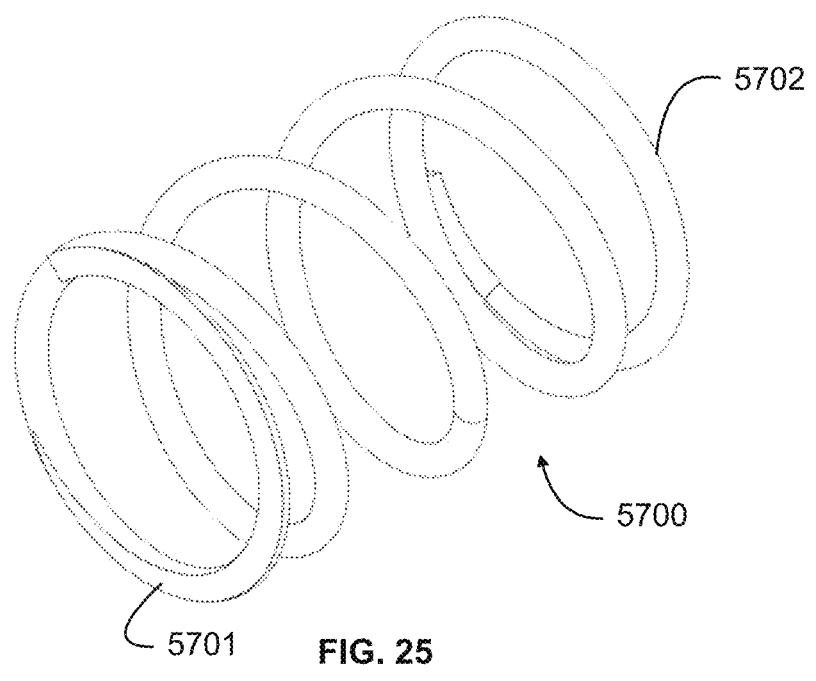
5702
5701 FIG. 25
5700
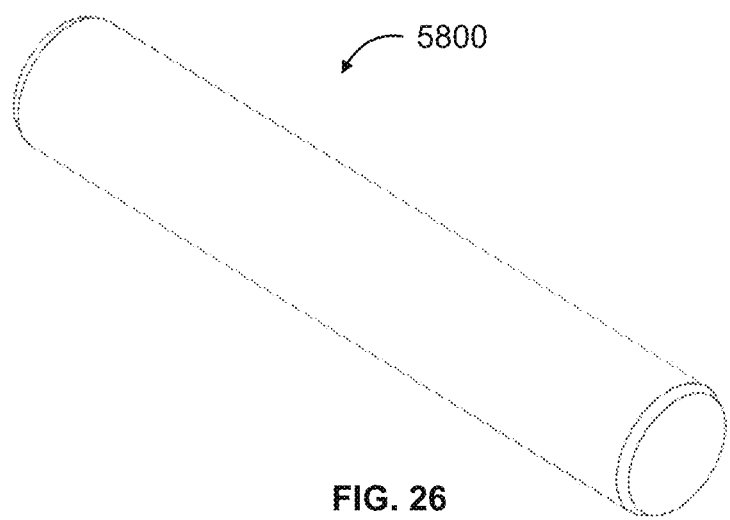
5800
FIG. 26

| Number of Visible Marks | Staple Bridge Width | | | | | |
|---|---|---|---|---|---|---|
| | 14mm | 17mm | 20mm | 23mm | 26mm | |
| 0 | 18 | 21 | 24 | 27 | 30 | Leg Length (mm) |
| 1 | 14 | 17 | 20 | 23 | 26 | |
| 2 | – | 13 | 16 | 19 | 22 | |
| 3 | – | – | – | – | – | |

FIG. 31

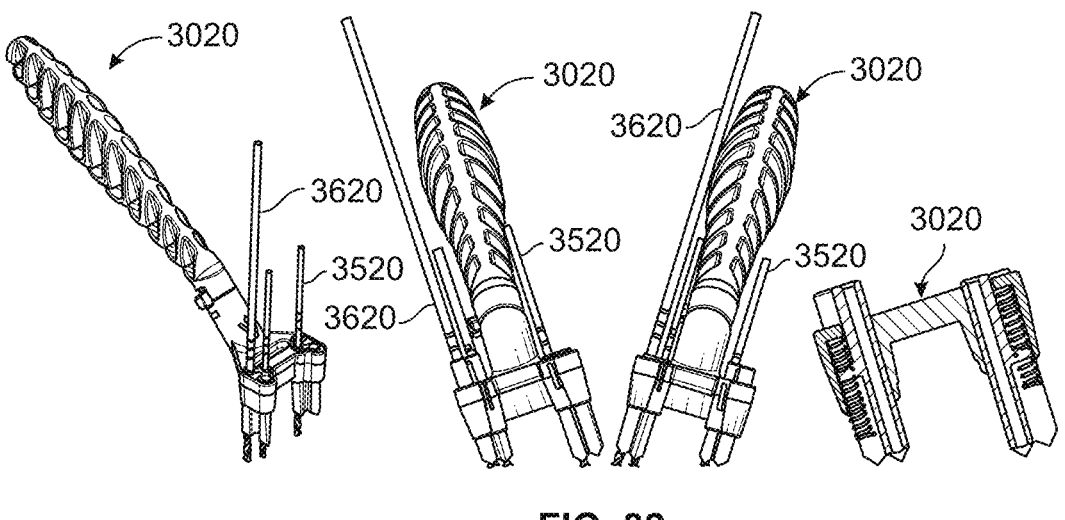
FIG. 32
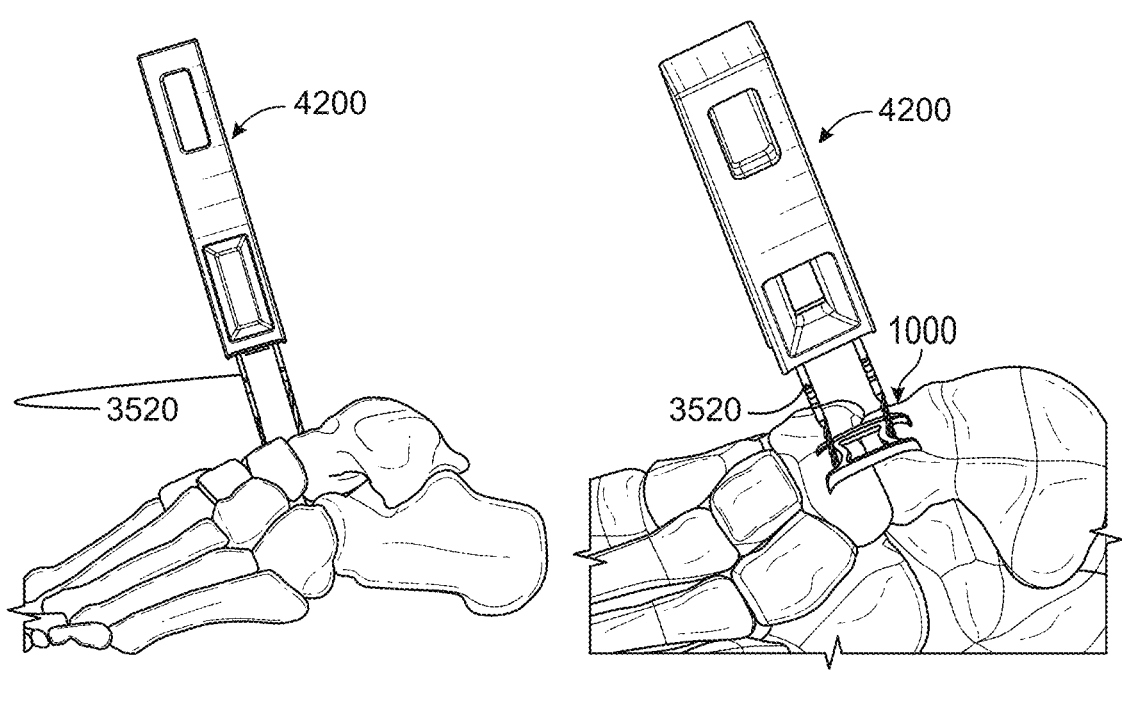
FIG. 33A          FIG. 33B

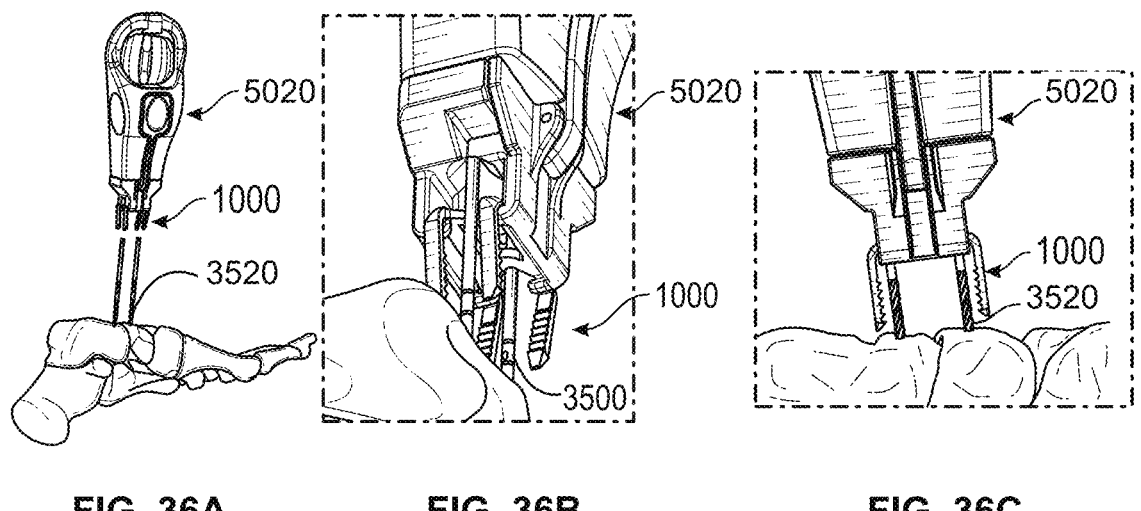
FIG. 36A        FIG. 36B        FIG. 36C
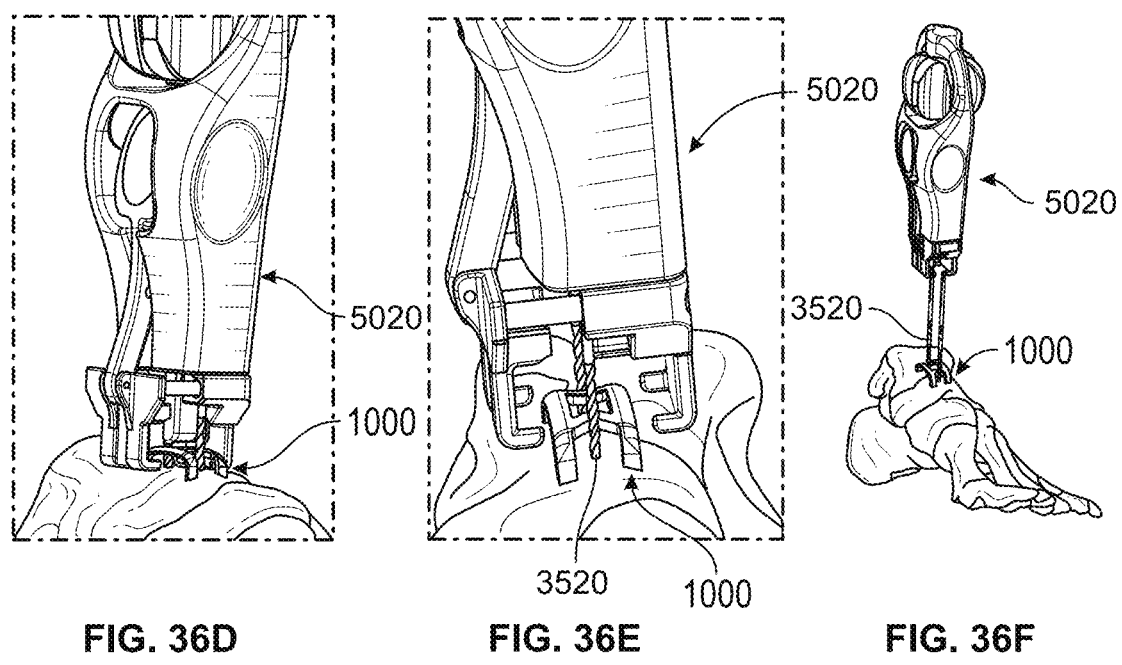
FIG. 36D        FIG. 36E        FIG. 36F

COMPRESSION STAPLE SYSTEMS AND METHODS

TECHNICAL FIELD

The present disclosure relates to systems and methods for use in orthopedic surgery. More specifically, the present disclosure relates to compression staple systems and methods for bone fixation.

BACKGROUND

Bone fractures and osteotomies are common medical conditions that require surgical intervention to ensure proper healing and alignment. Traditionally, compression staples have been used in orthopedic surgeries to provide stabilization and compression across fractures and joints. Despite their widespread use, the placement and effectiveness of traditional compression staples can be hindered by several challenges.

One of the primary challenges is the precise placement of the compression staple to ensure optimal compression and stability. Misalignment or improper insertion of the compression staple can lead to inadequate stabilization, delayed healing, or even resulting in non-union of the bone fragments.

Surgeons often rely on manual techniques and conventional instruments, which can be cumbersome and may not provide the necessary precision. In some locations, the surface of the bone and/or bone portions may be uneven, which in turn may cause difficulties in accurately drilling guide holes for the compression staple. In addition, the optimal joint or osteotomy may not be normal to the local surface. To achieve optimal compression, the staple legs be parallel to the joint, regardless of the surface geometry. Proper guide hole placement can be critical to ensure the desired compression across the fracture or joint, which may be critical to the healing process.

There is a need for a system to aid in the precise and accurate drilling of guide holes for compression staples in the bone. Furthermore, many of the subsequent steps in the surgical implantation of a compression staple require accuracy and stability, and, therefore, there is also a need for a system that is capable of supporting the subsequent steps in the insertion of a compression staple after the drilling of the guide holes.

SUMMARY

The various systems and methods of the present disclosure have been developed in response to the present state of the art, and in particular, in response to the problems and needs in the art that have not yet been fully solved by currently available tibial prosthesis systems used in knee arthroplasty.

In some embodiments, a method for bone fixation using a compression staple system may include loading a compression staple including two legs into an inserter, positioning a drill guide proximate a first bone portion and a second bone portion, using the drill guide and a drill to create a first hole in the first bone portion and a second hole in the second bone portion, wherein the first hole and the second hole may be configured to receive the two legs of the compression staple, using the drill guide and a first drill pin, driving the first drill pin into the first bone portion, using the drill guide and a second drill pin, driving the second drill pin into the second bone portion, withdrawing the drill guide and leaving the first drill pin in the first bone portion and the second drill pin in the second bone portion, guiding the inserter and the compression staple over the first drill pin and the second drill pin, inserting the two legs of the compression staple into the first two holes and the second two holes, actuating the inserter to release the compression staple, withdrawing the inserter, and removing the first drill pin and the second drill pin.

In the method of any preceding paragraph, the method may further include guiding an impactor over the first drill pin and the second drill pin and using the impactor to assess a first surface of the bone portion and a second surface of the second bone portion to determine if the compression staple is insertable to be flush with the first surface and the second surface.

In the method of any preceding paragraph, the method may further include guiding an impactor over the first drill pin and the second drill pin to impact the compression staple flush with a first surface of the first bone portion and a second surface of the second bone portion.

In the method of any preceding paragraph, the drill guide may include a handle, a foot portion coupled to the handle, a first guide sleeve slidably received in the foot portion and including a first aperture configured to guide the drill towards the first bone portion, and a second guide sleeve slidably received in the foot portion and including a second aperture configured to guide the drill towards the second bone portion. The method may further include, with a first resilient member, urging a first bone contacting end of the first guide sleeve against the bone, and, with a second resilient member, urging a second bone contacting end of the second guide sleeve against the bone, independently of urging the first bone contacting end of the first guide sleeve against the bone.

In the method of any preceding paragraph, loading the compression staple may include moving a moveable jaw of the inserter, relative to a stationary jaw of the inserter to an open position in which the moveable jaw may be spaced apart from the stationary jaw a first distance, engaging a first retention mechanism of the stationary jaw with the compression staple, engaging a second retention mechanism of the moveable jaw with the compression staple, and moving the moveable jaw, relative to the stationary jaw, to a closed position in which the moveable jaw may be spaced apart from the stationary jaw a second distance that is less than the first distance. Actuating the inserter to release the compression staple may include, moving the moveable jaw, relative to the stationary jaw, to the open position in which the first retention mechanism may disengage the compression staple, and disengaging the second retention mechanism from the compression staple. The stationary jaw and the moveable jaw may remain parallel between the closed position and the open position.

In the method of any preceding paragraph, the first bone portion and the second bone portion may be separated by a joint or a fracture.

In the method of any preceding paragraph, creating the first hole in the first bone portion may include creating the first hole generally parallel to the joint or the fracture, and creating the second hole in the second bone portion may include creating the second hole generally parallel to the joint or the fracture.

In some embodiments, a method of bone fixation using a compression staple system may include using a sizer to determine a desired compression staple size, loading a compression staple into an inserter, positioning a drill guide proximate a first bone portion and a second bone portion, using the drill guide and a drill to create a first plurality of holes in the first bone portion and a second plurality of holes in the second bone portion, using the drill guide and a first drill pin to drive the first drill pin into the first bone portion, using the drill guide and a second drill pin to drive the second drill pin into the second bone portion, withdrawing the drill guide and leaving the first drill pin in the first bone portion and the second drill pin in the second bone portion, guiding the inserter and the compression staple over the first drill pin and the second drill pin, inserting the compression staple into the first bone portion and the second bone portion, actuating the inserter to release the compression staple, withdrawing the inserter, and removing the first drill pin and the second drill pin.

In the method of any preceding paragraph, the method may further include guiding an impactor over the first drill pin and the second drill pin and using the impactor to assess a first surface of the first bone portion and a second surface of the second bone portion to determine if the compression staple is insertable to be flush with the first surface and the second surface.

In the method of any preceding paragraph, the method may further include guiding an impactor over the first drill pin and the second drill pin to impact the compression staple flush with a first surface of the first bone portion and a second surface of the second bone portion.

In the method of any preceding paragraph, the drill guide may include a handle, a foot portion coupled to the handle, a first sleeve slidably received in the foot portion and including a first aperture configured to guide the drill towards the first bone portion, and a second guide sleeve slidably received in the foot portion and including a second aperture configured to guide the drill towards the second bone portion. The first guide sleeve and the second guide sleeve may be independently spring-loaded relative to the foot portion.

In the method of any preceding paragraph, the inserter may be configured to releasable engage the compression staple. The inserter may include a stationary jaw including a pair of first hooks configured to engage the compression staple, a moveable jaw including a pair of second hooks configured to engage the compression staple, a closed configuration wherein the stationary jaw may be spaced apart from the moveable jaw a first distance, and an open configuration wherein the stationary jaw may be spaced apart from the moveable jaw a second distance greater than the first distance. The compression staple may be captive within the inserter with the inserter in the closed configuration. The compression staple may be releasable from the inserter with the inserter in the open configuration, and the stationary jaw and the moveable jaw remain parallel between the closed configuration and the open configuration.

In the method of any preceding paragraph, the first bone portion and the second bone portion may be separated by a joint or a fracture.

In the method of any preceding paragraph, creating the first plurality of holes in the first bone portion may include creating the first plurality of holes generally parallel to the joint or the fracture, and creating the second plurality of holes in the second bone portion may include creating the second plurality of holes generally parallel to the joint or the fracture.

In some embodiments, a method of bone fixation using a compression staple system may include loading a compression staple into an inserter and using a drill guide and a drill to create a first hole in a first bone portion and a second hole in the first bone portion, a third hole in a second bone portion, and a fourth hole in the second bone portion. The drill guide may include a handle, a foot portion coupled to the handle, and a first guide sleeve captively and slidably received in the foot portion. The first guide sleeve may include a first aperture configured to guide the drill along a first trajectory and a second aperture configured to guide the drill along a second trajectory. The drill guide may further include a second guide sleeve captively and slidably received in the foot portion and spaced apart from the first guide sleeve. The second guide sleeve may include a third aperture configured to guide the drill along a third trajectory and a fourth aperture configured to guide the drill along a fourth trajectory. The first trajectory, the second trajectory, the third trajectory, and the fourth trajectory may be all parallel. The method may further include inserting the compression staple into the first hole, the second hole, the third hole, and the fourth hole, actuating the inserter to release the compression staple, and withdrawing the inserter.

In the method of any preceding paragraph, the method may further include using the drill guide and a second drill to create a fifth hole in the first bone portion using a fifth aperture in the drill guide, the fifth aperture may include a fifth trajectory, and using the drill guide and a third drill to create a sixth hole in the second bone portion using a sixth aperture in the drill guide, the sixth aperture may include a sixth trajectory. The fifth trajectory and the sixth trajectory may be parallel to the first trajectory.

In the method of any preceding paragraph, the method may further include guiding an impactor over a first drill pin inserted into the first bone portion and a second drill pin inserted into a second bone portion and using the impactor to assess a first surface of the first bone portion and a second surface of the second bone portion to determine if the compression staple is insertable to be flush with the first surface and the second surface.

In the method of any preceding paragraph, the method may further include guiding an impactor over a first drill pin inserted into the first bone portion and a second drill pin inserted into the second bone portion to impact the compression staple flush with a first surface of the first bone portion and a second surface of the second bone portion.

In the method of any preceding paragraph, the inserter may be configured to releasably engage the compression staple. The inserter may include a stationary jaw including a pair of first hooks configured to engage the compression staple, a moveable jaw including a pair of second hooks configured to engage the compression staple, a closed configuration wherein the stationary jaw may be spaced apart from the moveable jaw a first distance, and an open configuration wherein the stationary jaw may be spaced apart from the moveable jaw a second distance greater than the first distance. The compression staple may be captive within the inserter with the inserter in the closed configuration. The compression staple may be releasable from the inserter with the inserter in the open configuration and the stationary jaw and the moveable jaw may remain parallel between the closed configuration and the open configuration.

In the method of any preceding paragraph, the method may further include, with the first bone portion and the second bone portion separated by a joint or a fracture, creating the first hole in the first bone portion may include creating the first hole generally parallel to the joint or the fracture, and creating the third hole in the second bone portion may include creating the third hole generally parallel to the joint or the fracture.

These and other features and advantages of the present disclosure will become more fully apparent from the following description and appended claims or may be learned by the practice of the implants, systems, and methods set forth hereinafter.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings.

FIG. 1A is a perspective view of a compression staple according to an embodiment of the present disclosure.

FIG. 1B is a top perspective view of the compression staple of FIG. 1A.

FIG. 1C is a side perspective view of the compression staple of FIG. 1A.

FIG. 1D is a front perspective view of the compression staple of FIG. 1A.

FIG. 6A is a perspective view of a sizer plate according to an embodiment of the present disclosure.

FIG. 6B is a top view of the sizer plate of FIG. 6A.

FIG. 6C is a front view of the sizer plate of FIG. 6A.

FIG. 6D is a side view of the sizer plate of FIG. 6A.

6

Figures 8A, 8B, 8C, 8D, 8E:
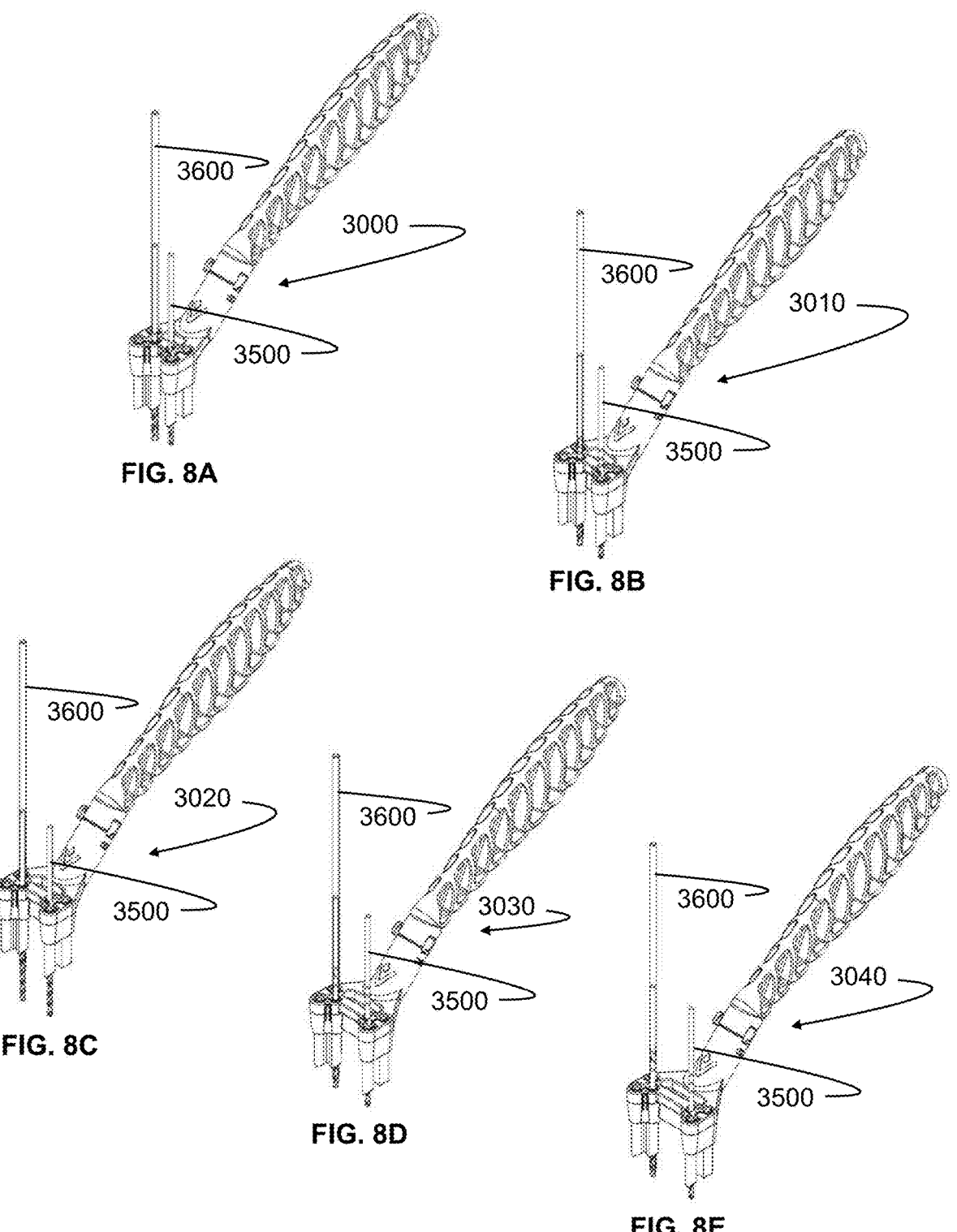
FIG. 8A is a perspective view of the drill guide, the short drill pins, and the long drill of FIG. 7A.
FIG. 8B is a perspective view of a drill guide, short drill pins, and a long drill according to an embodiment of the present disclosure.
FIG. 8C is a perspective view of a drill guide, short drill pins, and a long drill according to an embodiment of the present disclosure.

FIG. 8D is a perspective view of a drill guide, short drill pins, and a long drill according to an embodiment of the present disclosure.

FIG. 8E is a perspective view of a drill guide, short drill pins, and a long drill according to an embodiment of the present disclosure.

Figures 9A, 9B, 9C, 9D:
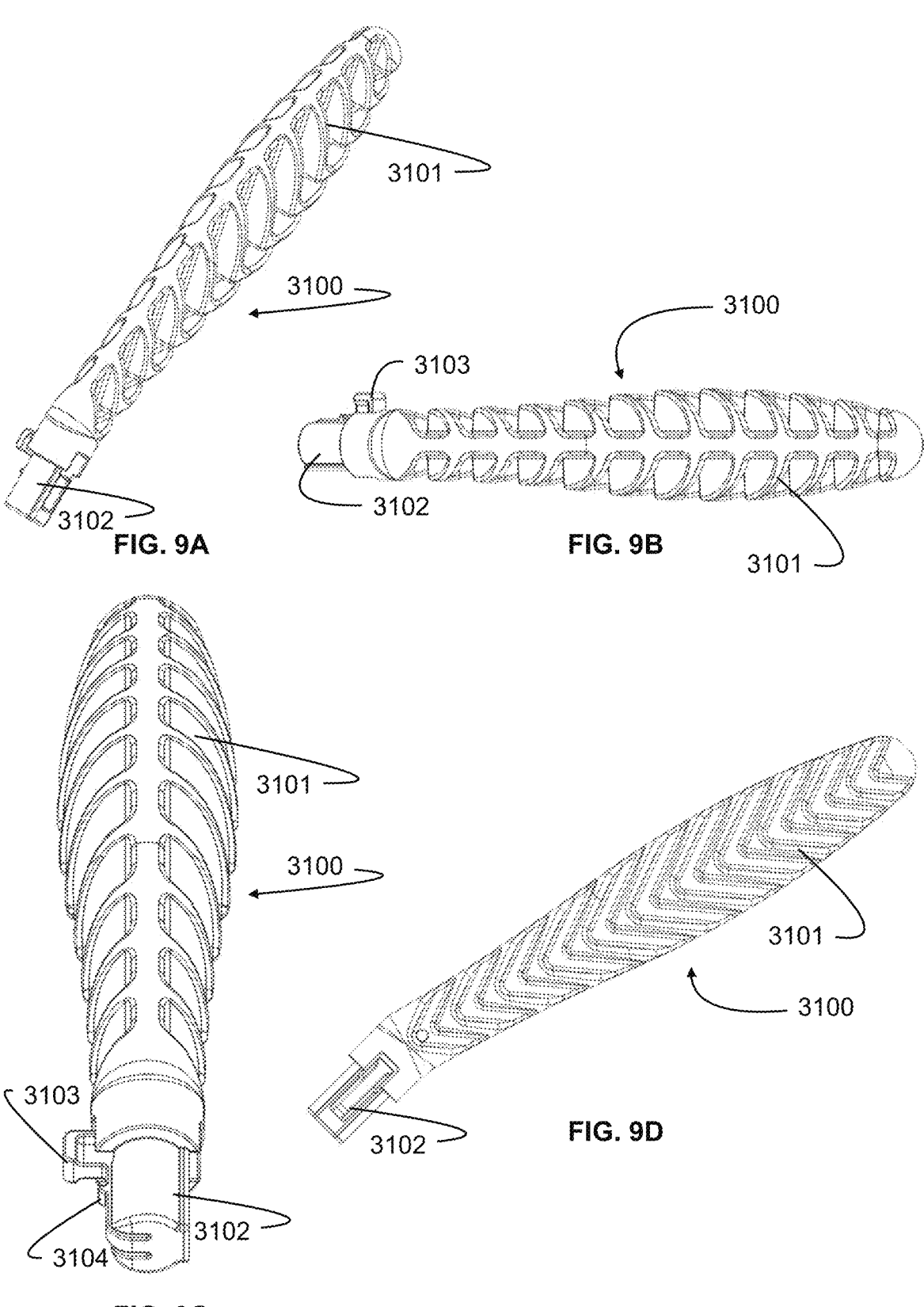

FIG. 9A is a perspective view of a handle according to an embodiment of the present disclosure.

FIG. 9B is a top view of the handle of FIG. 9A.

FIG. 9C is a front view of the handle of FIG. 9A.

FIG. 9D is a side view of the handle of FIG. 9A.

Figures 10A, 10B, 10C, 10D:
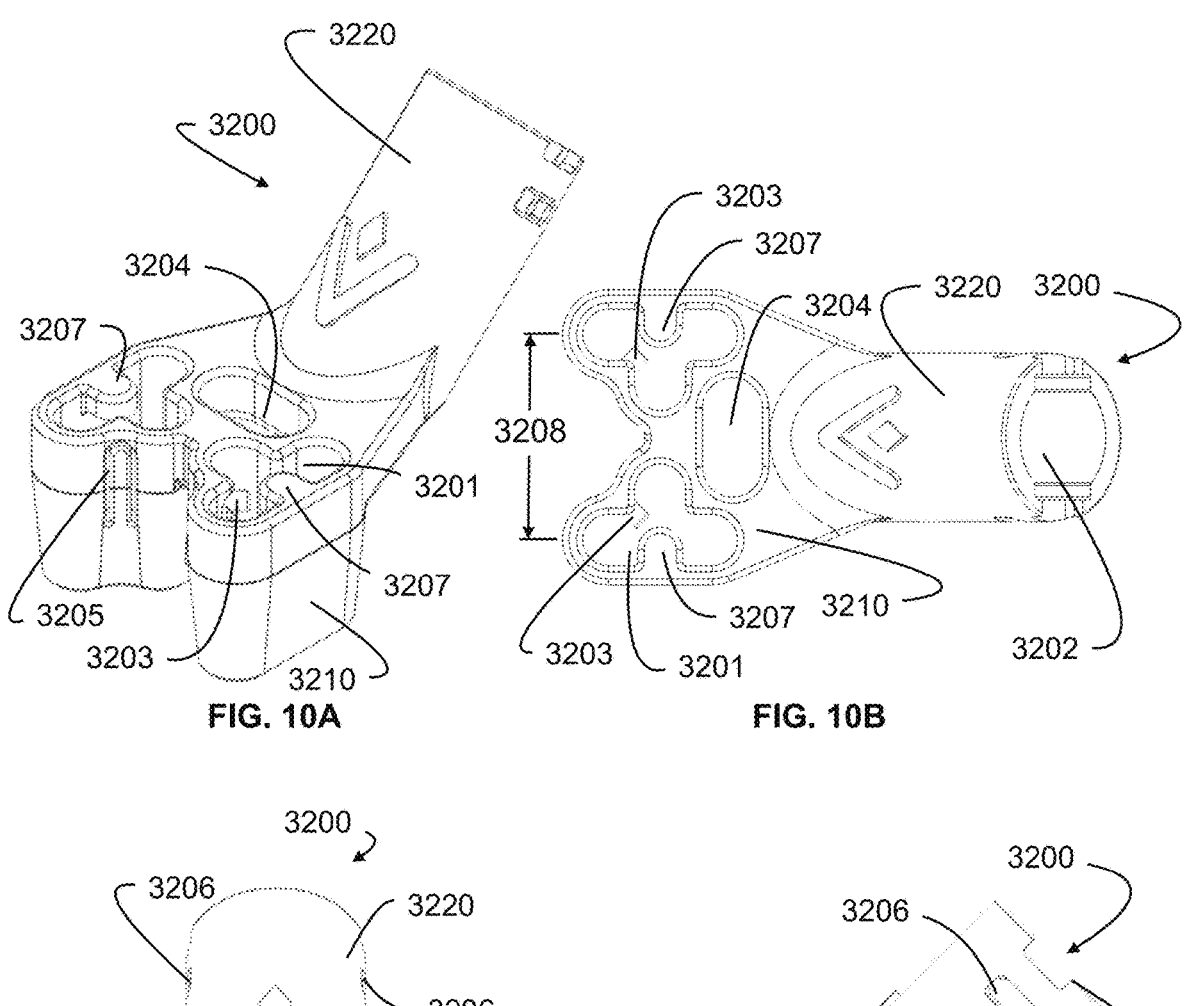

FIG. 10A is a perspective view of a foot portion according to an embodiment of the present disclosure.

FIG. 10B is a top view of the foot portion of FIG. 10A.

FIG. 10C is a front view of the foot portion of FIG. 10A.

FIG. 10D is a side view of the foot portion of FIG. 10A.

Figures 11A, 11B, 11C, 11D:
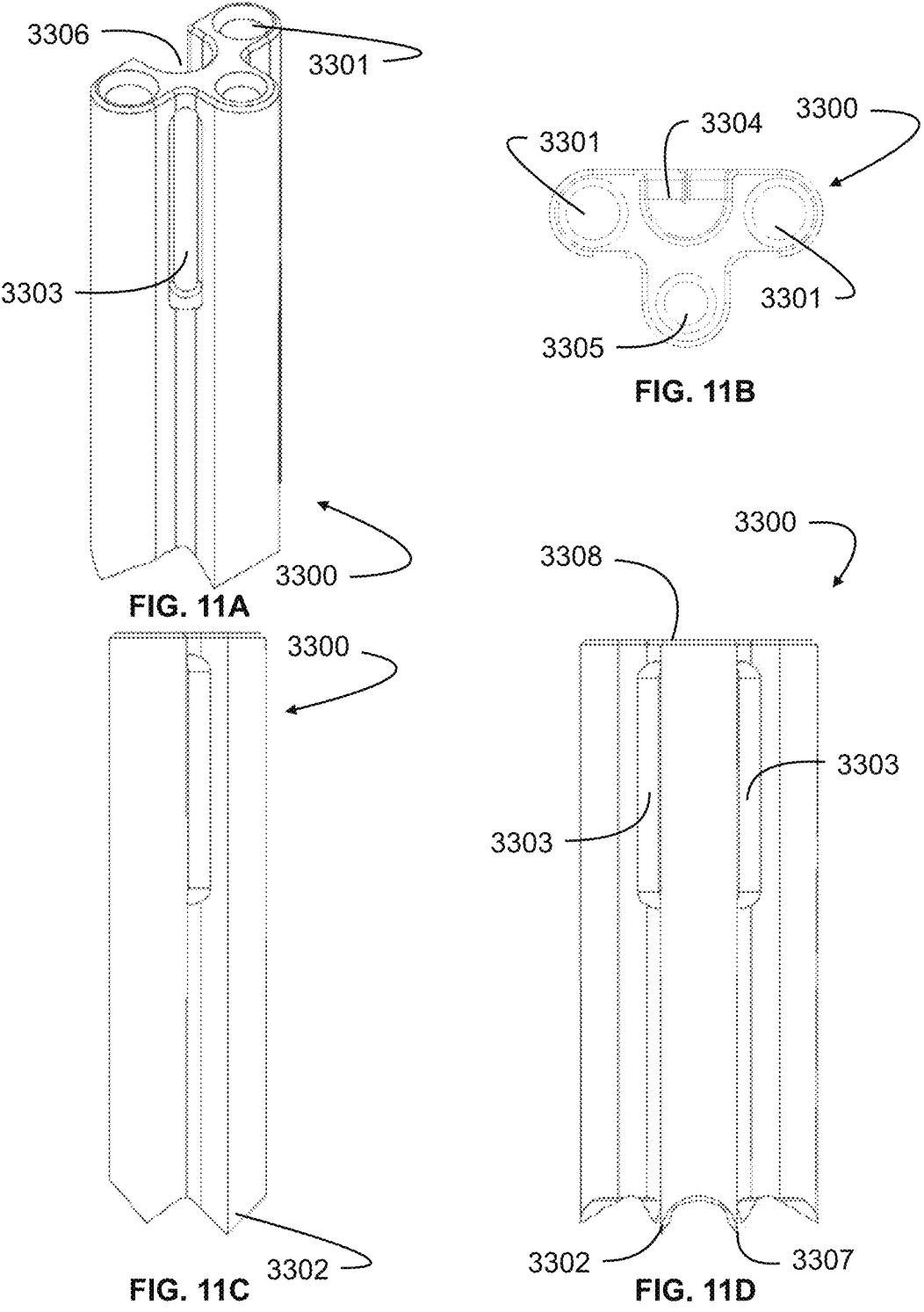

FIG. 11A is a perspective view of a guide sleeve according to an embodiment of the present disclosure.

FIG. 11B is a top view of the guide sleeve of FIG. 11A.

FIG. 11C is a front view of the guide sleeve of FIG. 11A.

FIG. 11D is a side view of the guide sleeve of FIG. 11A.

Figures 12, 13, 14:
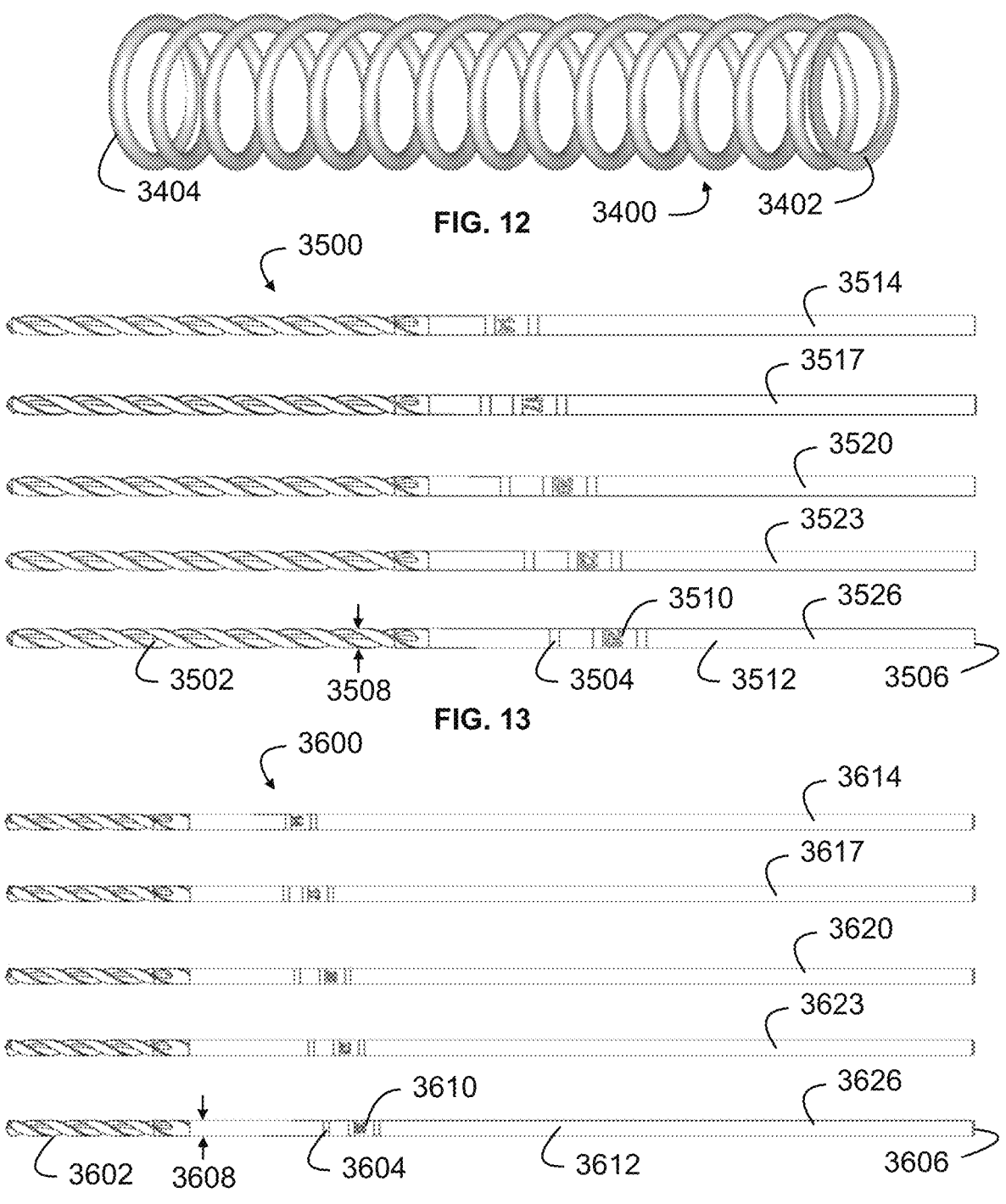

FIG. 12 is a side view of a compression spring according to an embodiment of the present disclosure.

FIG. 13 is a side view of a set of short drill pins according to an embodiment of the present disclosure.

FIG. 14 is a side view of a set of long drills according to an embodiment of the present disclosure.

Figures 15A, 15B, 15C, 15D:
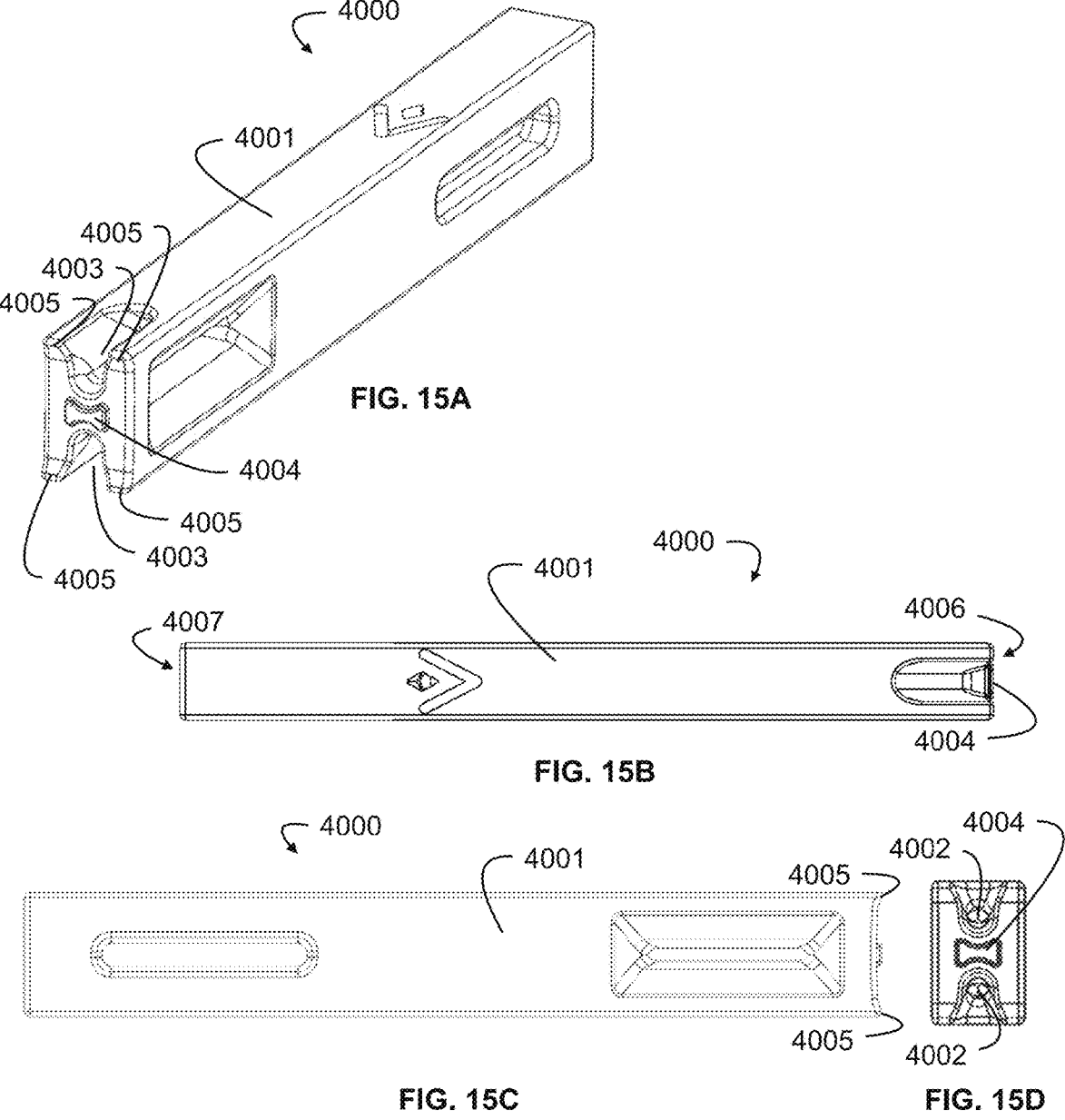

FIG. 15A is a perspective view of an impactor according to an embodiment of the present disclosure.

FIG. 15B is a top view of the impactor of FIG. 15A.

FIG. 15C is a front view of the impactor of FIG. 15A.

FIG. 15D is a side view of the impactor of FIG. 15A.

Figures 16A, 16B, 16C, 16D, 16E:
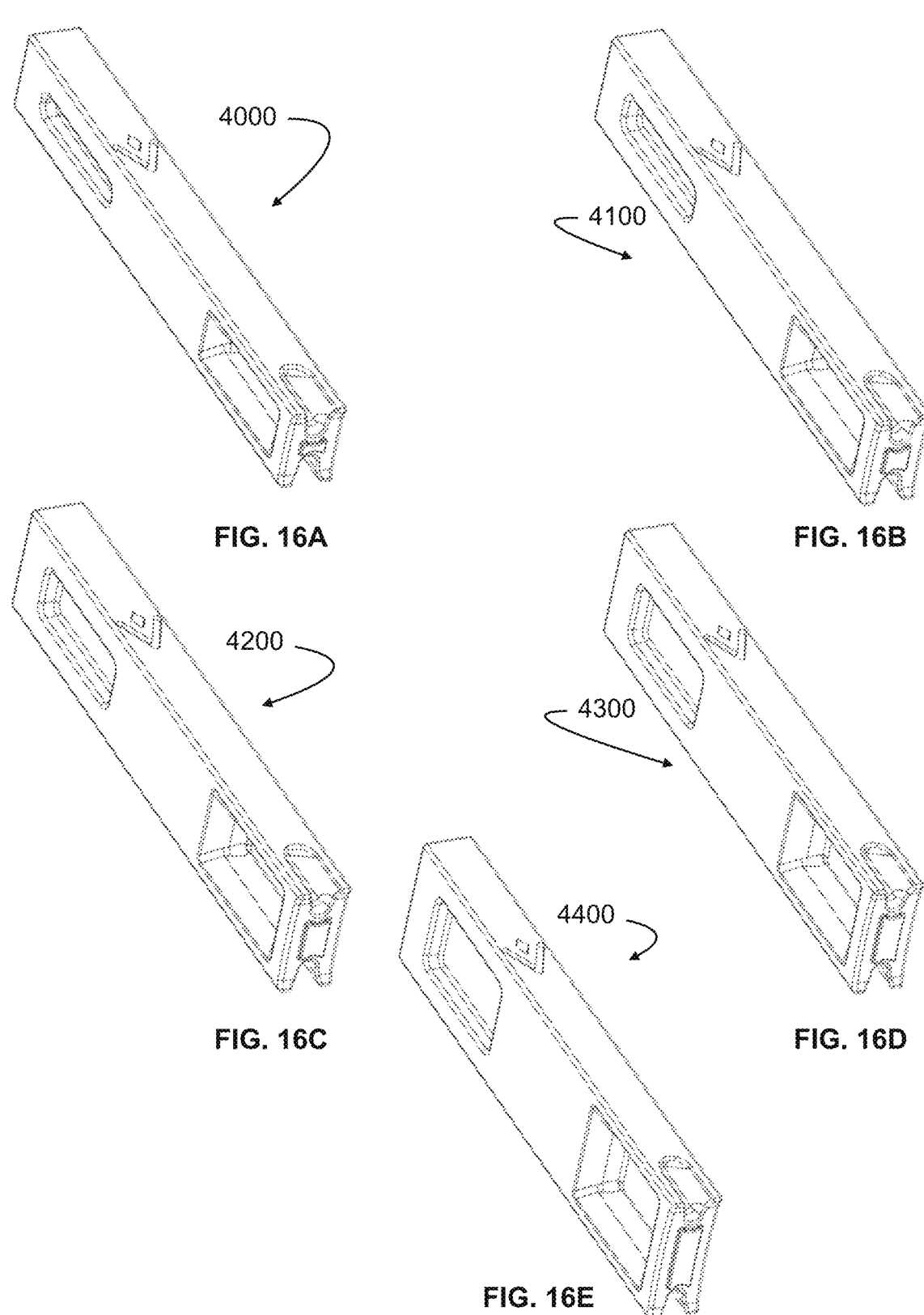

FIG. 16A is a perspective view of the impactor of FIG. 15A.

FIG. 16B is a perspective view of an impactor according to an embodiment of the present disclosure.

FIG. 16C is a perspective view of an impactor according to an embodiment of the present disclosure.

FIG. 16D is a perspective view of an impactor according to an embodiment of the present disclosure.

FIG. 16E is a perspective view of an impactor according to an embodiment of the present disclosure.

FIG. 17A is a perspective view of an inserter according to an embodiment of the present disclosure.

FIG. 17B is a top view of the inserter of FIG. 17A.

FIG. 17C is a front view of the inserter of FIG. 17A.

FIG. 17D is a side view of the inserter of FIG. 17A.

Figures 18A, 18B, 18C, 18D, 18E:
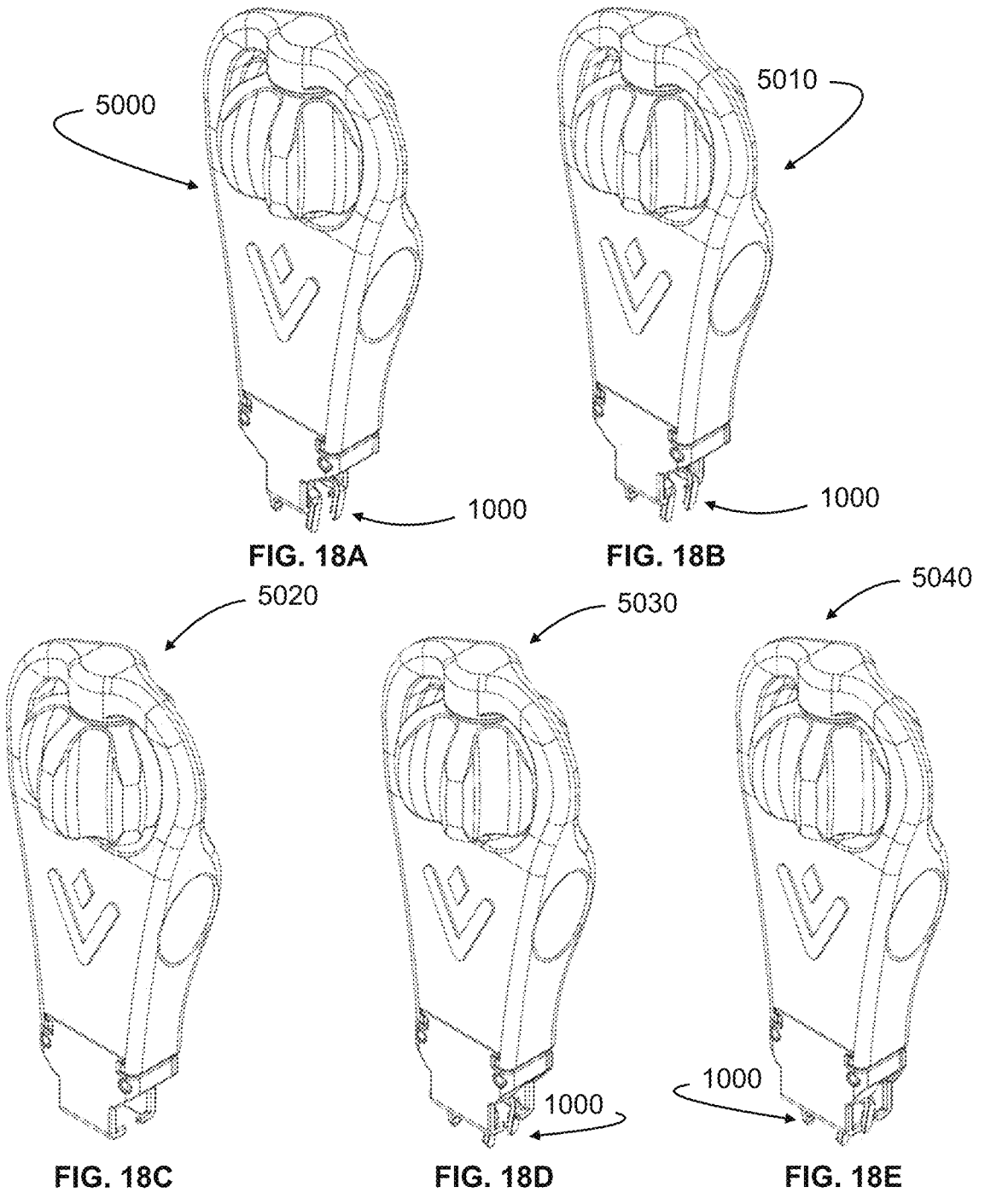

FIG. 18A is a perspective view of the inserter of FIG. 17A.

FIG. 18B is a perspective view of an inserter according to an embodiment of the present disclosure.

FIG. 18C is a perspective view of an inserter according to an embodiment of the present disclosure.

FIG. 18D is a perspective view of an inserter according to an embodiment of the present disclosure.

FIG. 18E is a perspective view of an inserter according to an embodiment of the present disclosure.

FIG. 19A is a perspective view of a body according to an embodiment of the present disclosure.

FIG. 19B is a top view of the body of FIG. 19A.

FIG. 19C is a front view of the body of FIG. 19A.

FIG. 19D is a side view of the body of FIG. 19A.

Figures 20A, 20B, 20C, 20D:
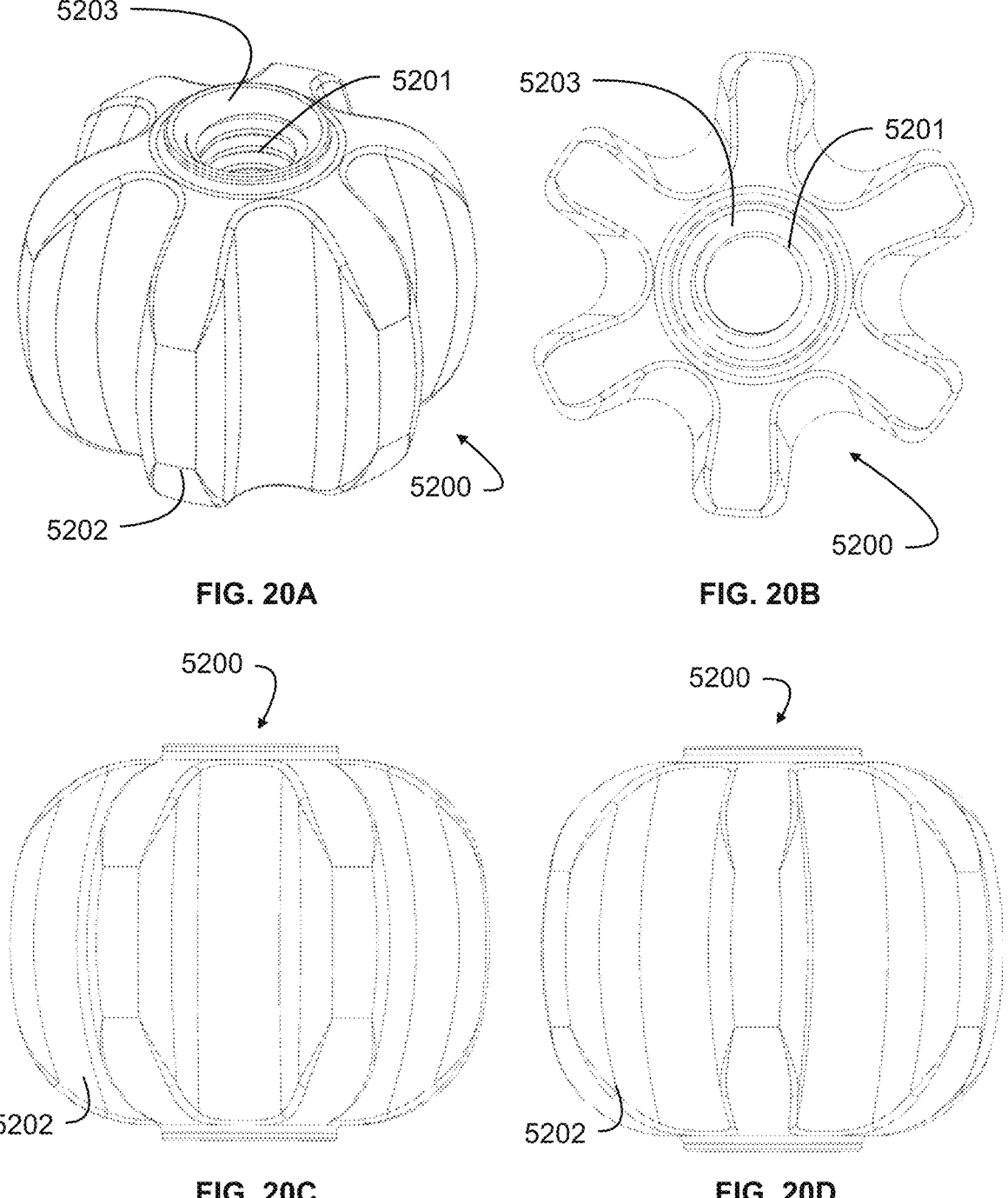

FIG. 20A is a perspective view of a knob according to an embodiment of the present disclosure.

FIG. 20B is a top view of the knob of FIG. 20A.

FIG. 20C is a front view of the knob of FIG. 20A.

FIG. 20D is a side view of the knob of FIG. 20A.

Figures 21A, 21B, 21C, 21D:
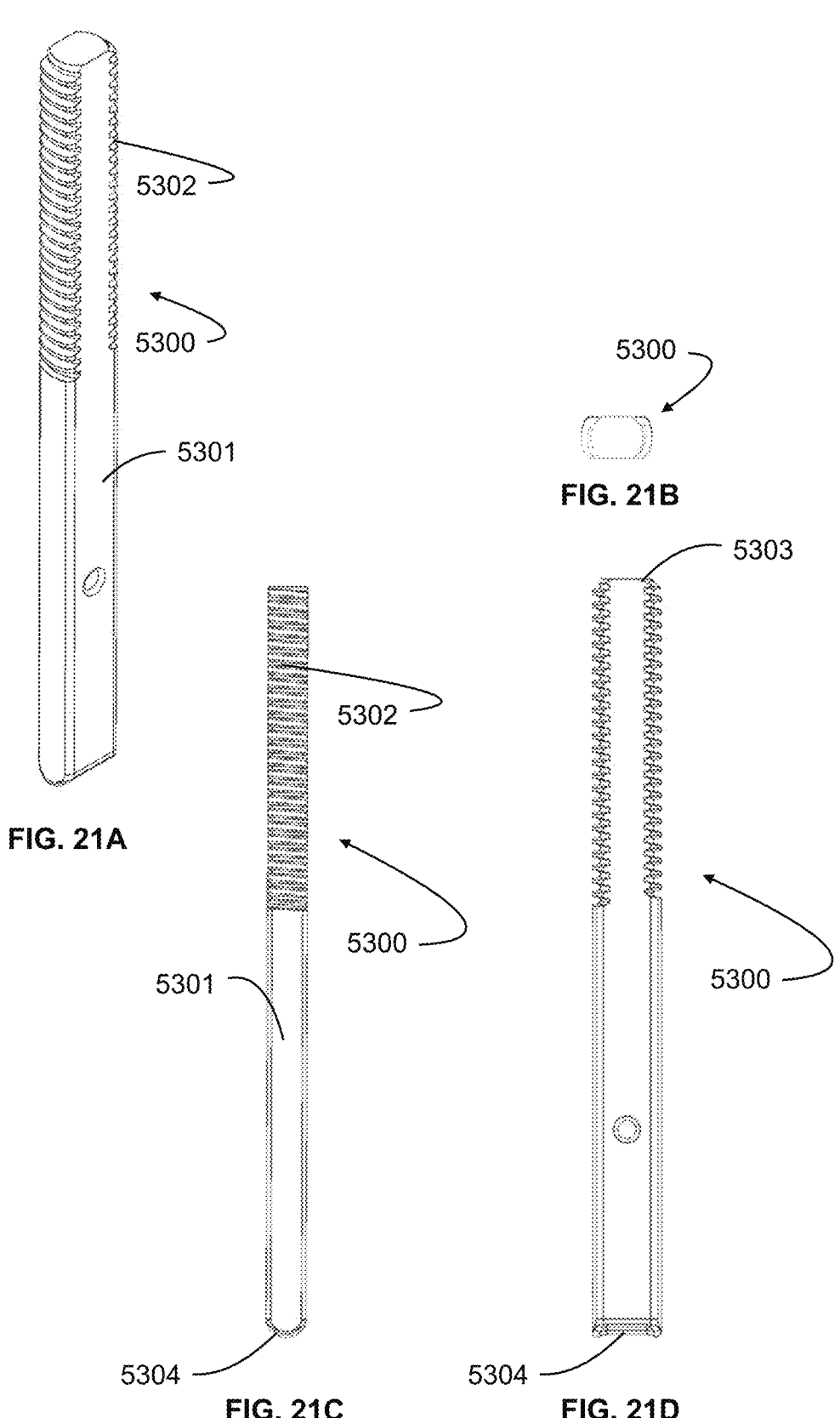

FIG. 21A is a perspective view of a drive shaft according to an embodiment of the present disclosure.

FIG. 21B is a top view of the drive shaft of FIG. 21A.

FIG. 21C is a front view of the drive shaft of FIG. 21A.

FIG. 21D is a side view of the drive shaft of FIG. 21A.

Figures 22A, 22B, 22C, 22D:
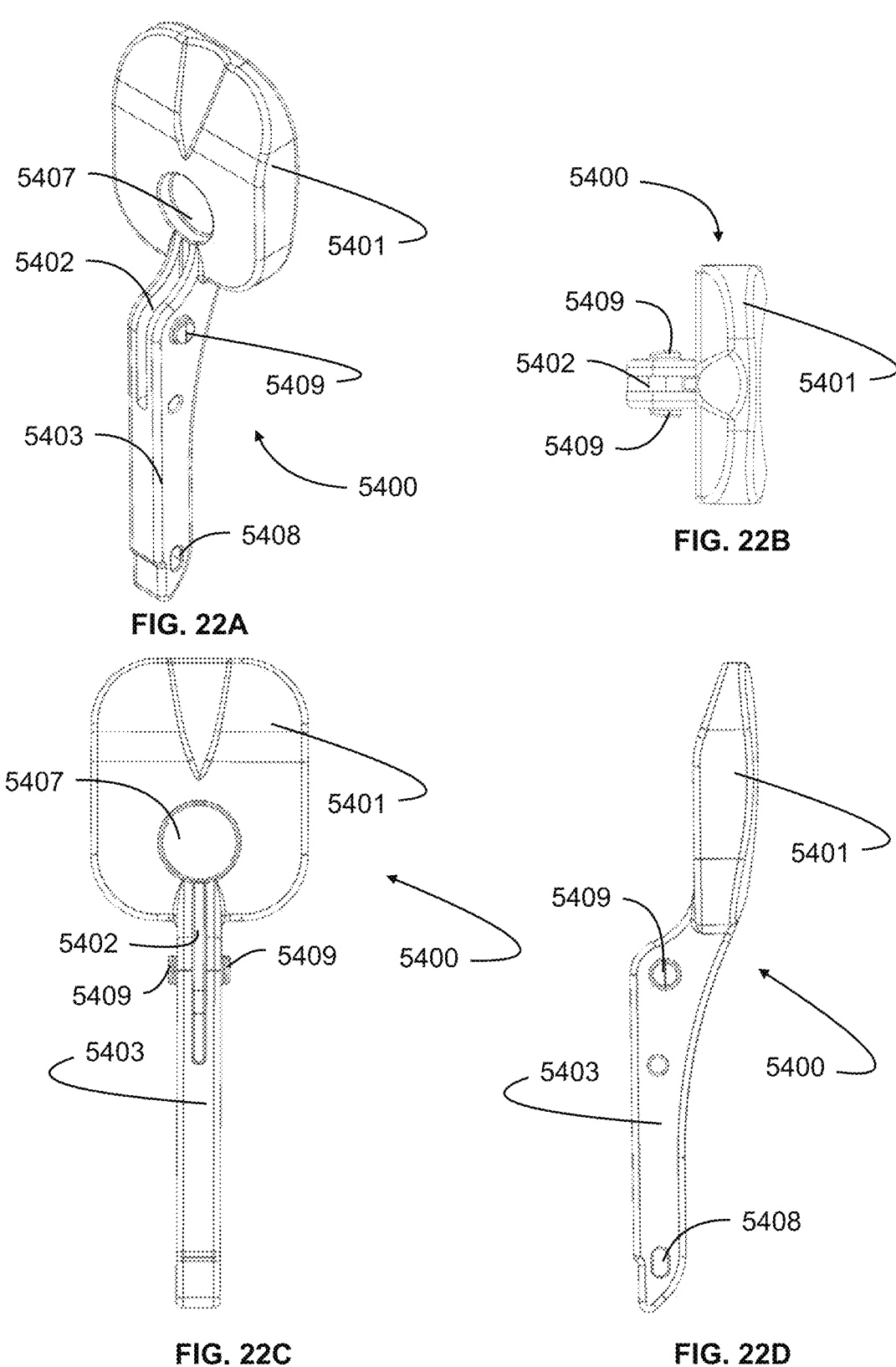

FIG. 22A is perspective view of a button according to an embodiment of the present disclosure.

FIG. 22B is a top view of the button of FIG. 22A.

FIG. 22C is a front view of the button of FIG. 22A.

FIG. 22D is a side view of the button of FIG. 22A.

Figures 23A, 23B, 23C, 23D:
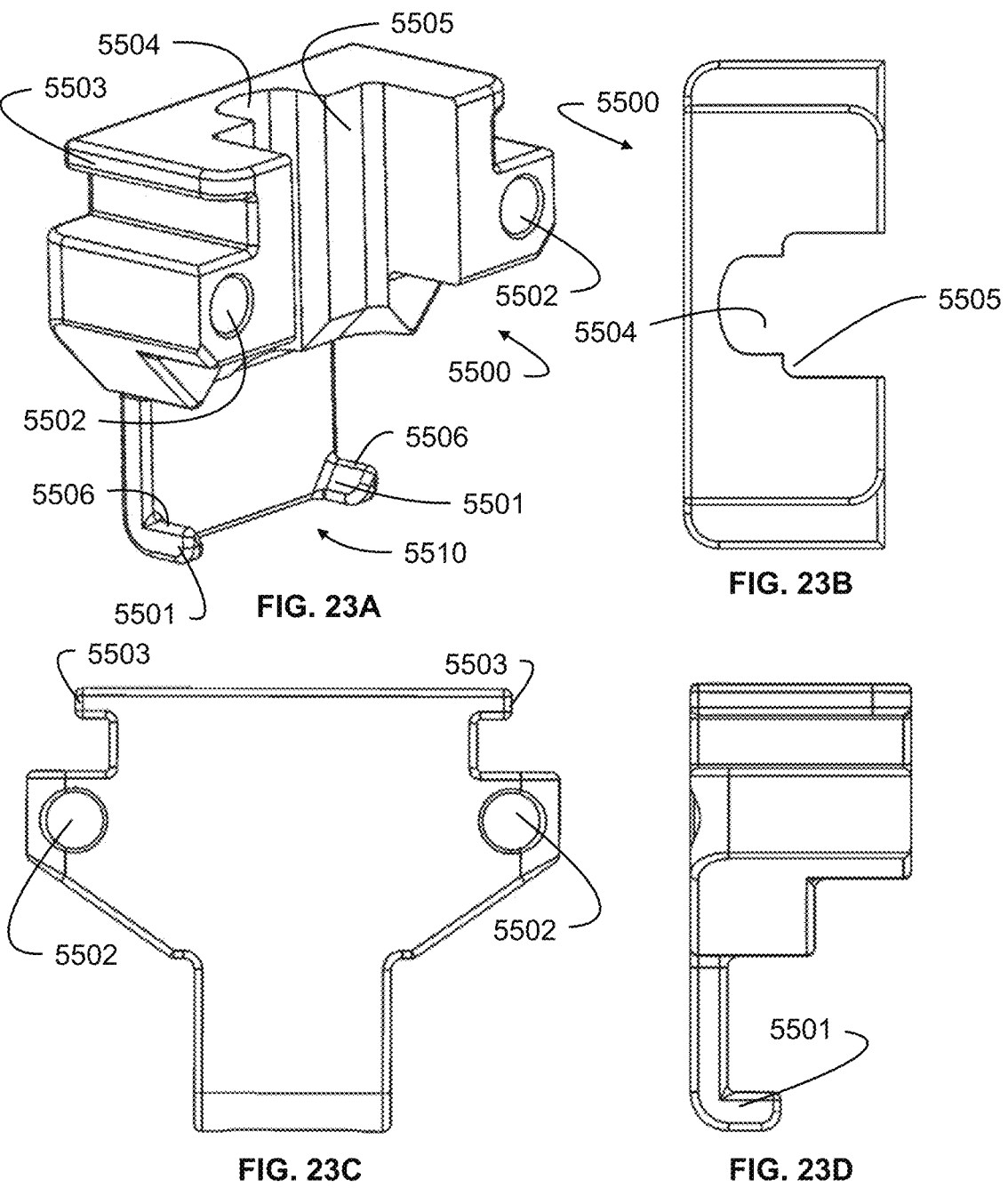

FIG. 23A is a perspective view of a stationary jaw according to an embodiment of the present disclosure.

FIG. 23B is a top view of the stationary jaw of FIG. 23A.

FIG. 23C is a front view of the stationary jaw of FIG. 23A.

FIG. 23D is a side view of the stationary jaw of FIG. 23A.

Figure 24A:
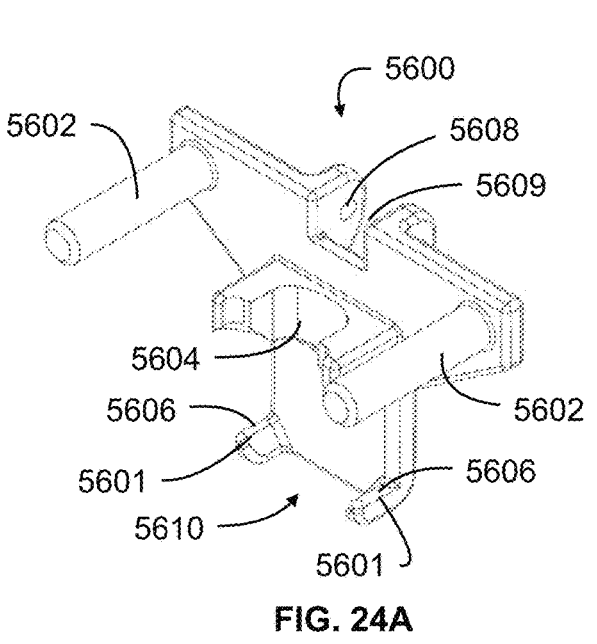

FIG. 24A is a perspective view of a movable jaw according to an embodiment of the present disclosure.

Figure 24B:
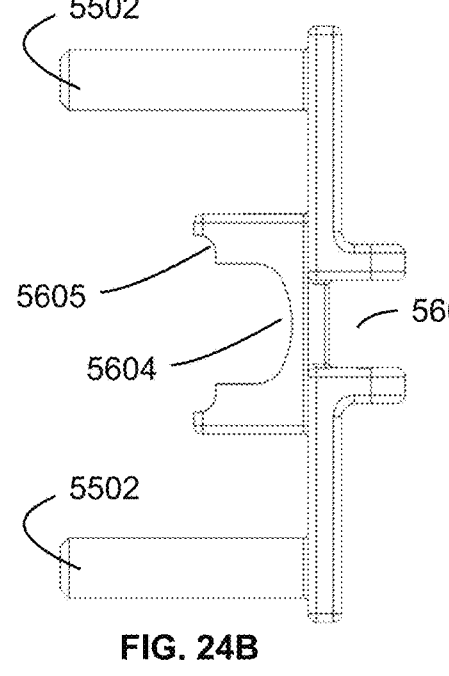

FIG. 24B is a top view of the movable jaw of FIG. 24A.

Figure 24C:
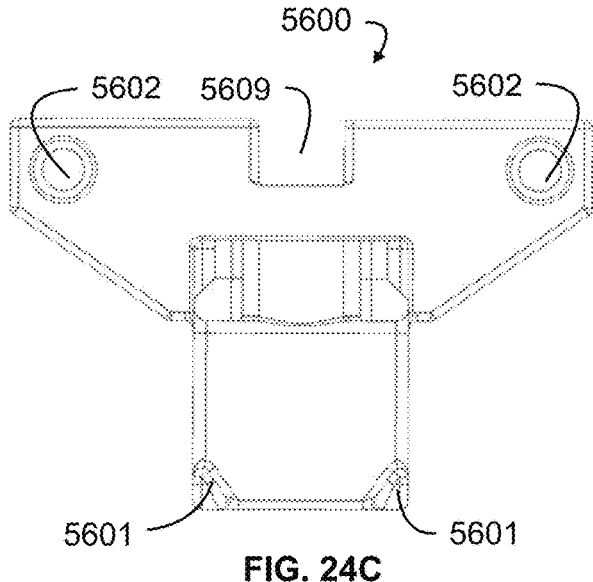

FIG. 24C is a front view of the movable jaw of FIG. 24A.

Figure 24D:
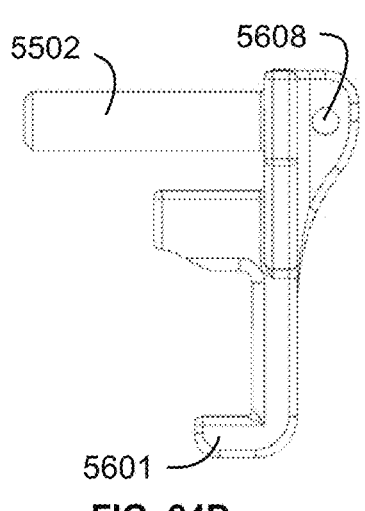

FIG. 24D is a side view of the movable jaw of FIG. 24A.

FIG. 25 is a perspective view of a spring according to an embodiment of the present disclosure.

FIG. 26 is a perspective view of a dowel pin according to an embodiment of the present disclosure.

Figure 27A:
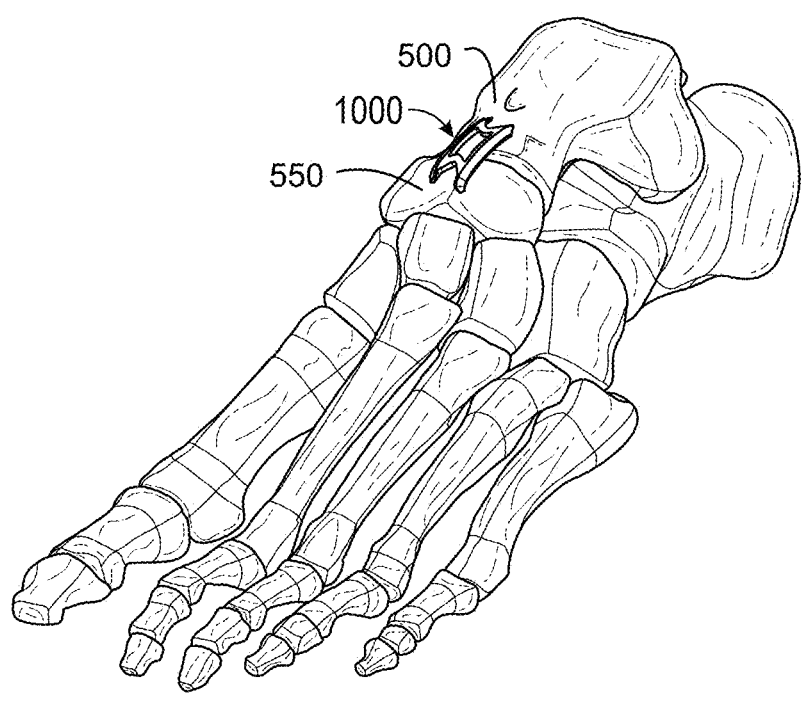

FIG. 27A is a perspective view of a foot and a compression staple according to an embodiment of the present disclosure.

Figure 27B:
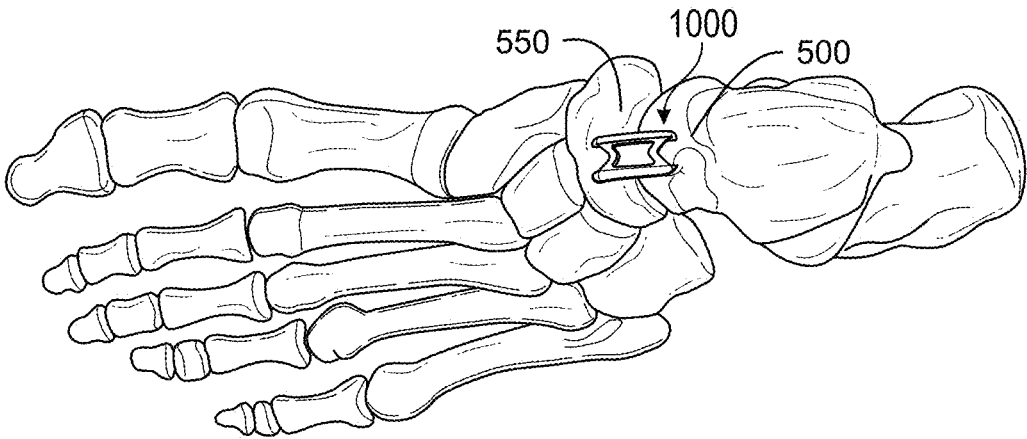

FIG. 27B is a top view of the foot and the compression staple of FIG. 27A.

Figure 28:
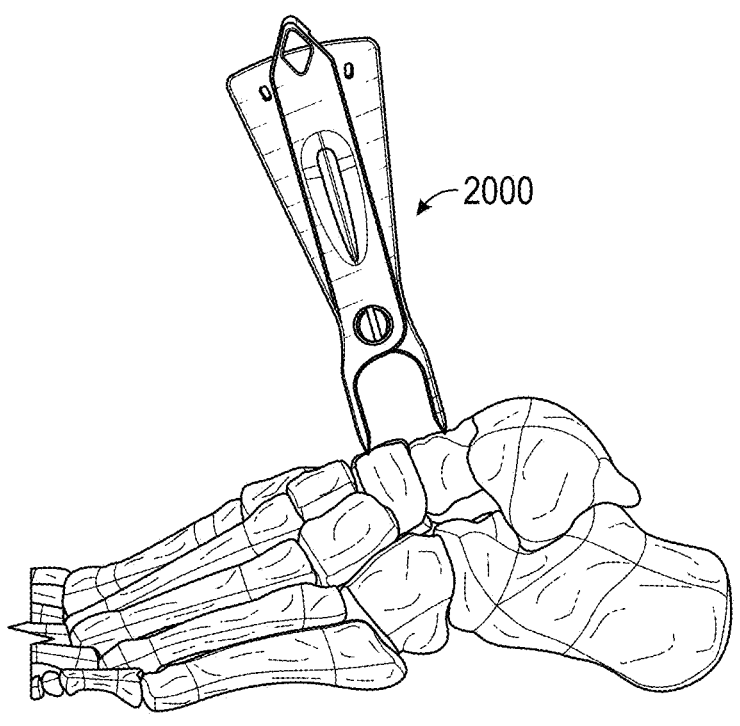

FIG. 28 is a perspective view of a foot and a sizer according to an embodiment of the present disclosure.

Figure 29:
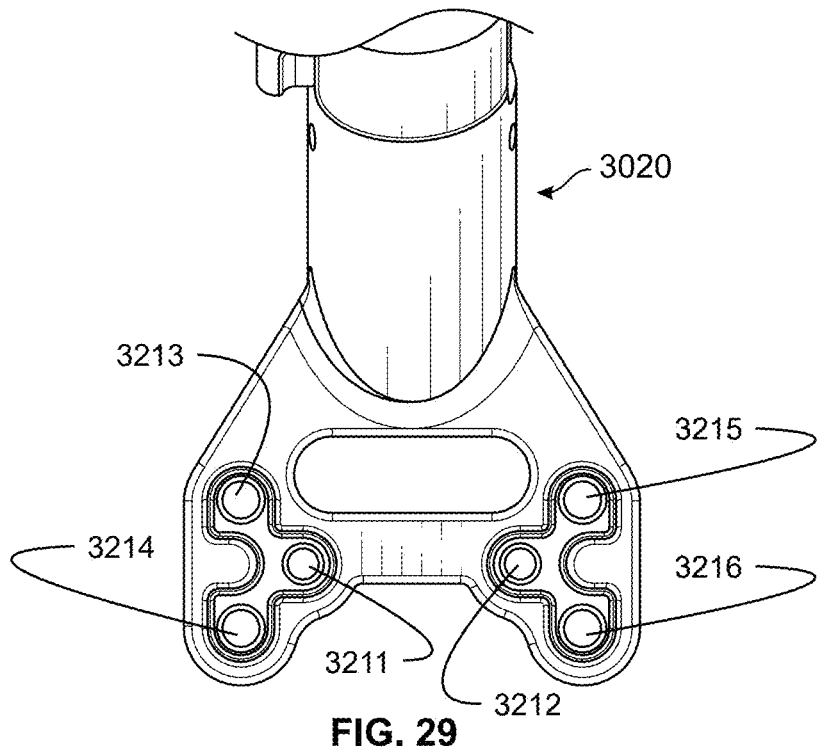

FIG. 29 is a partial top view of a drill guide according to an embodiment of the present disclosure.

Figure 30A:
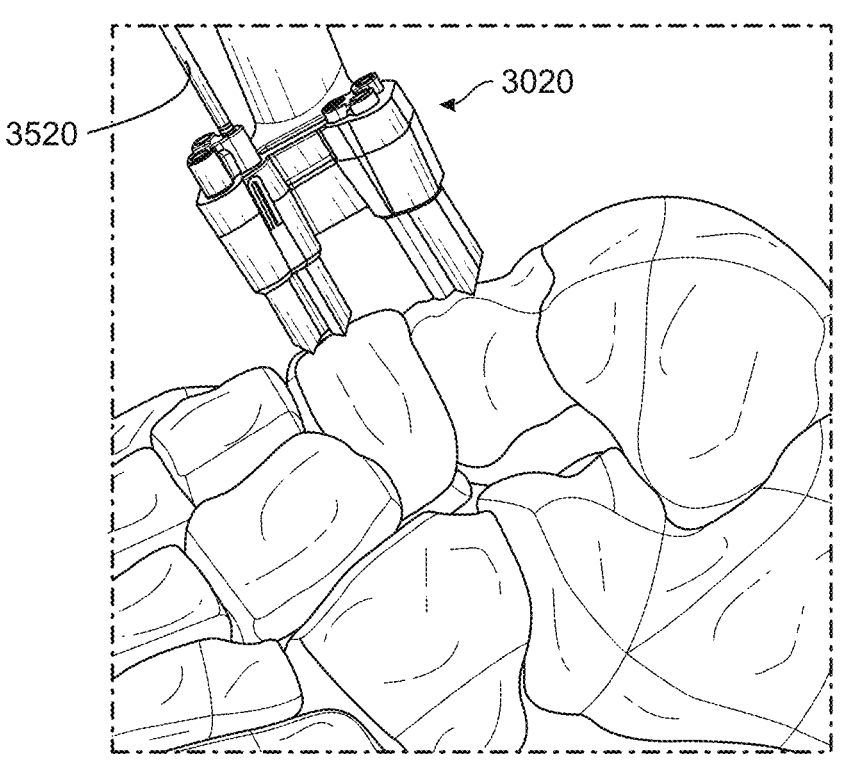

FIG. 30A is a perspective view of a foot, a drill guide, and a short drill pin according to an embodiment of the present disclosure.

Figure 30B:
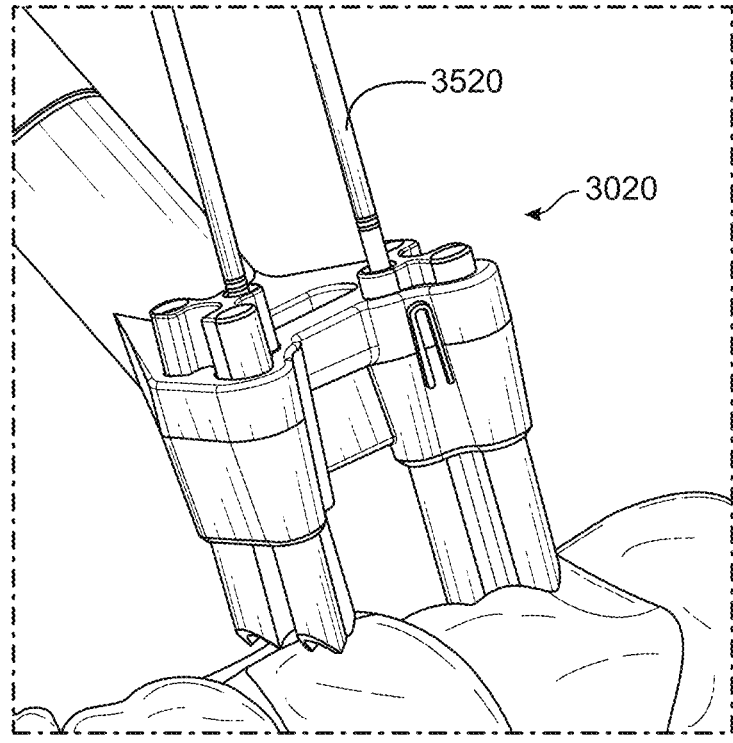

FIG. 30B is a perspective view of the foot, the drill guide, and two short drill pins according to an embodiment of the present disclosure.

FIG. 31 is a table of compression staple leg lengths and compression staple bridge lengths according to an embodiment of the present disclosure.

FIG. 32 is a series of perspective views of a drill guide, short drill pins, and a long drill according to an embodiment of the present disclosure.

FIG. 33A is a perspective view of a foot, two short drill pins, and an impactor according to an embodiment of the present disclosure.

FIG. 33B is a perspective view of the foot, the two short drill pins, the impactor, and a compression staple according to an embodiment of the present disclosure.

Figure 34A:
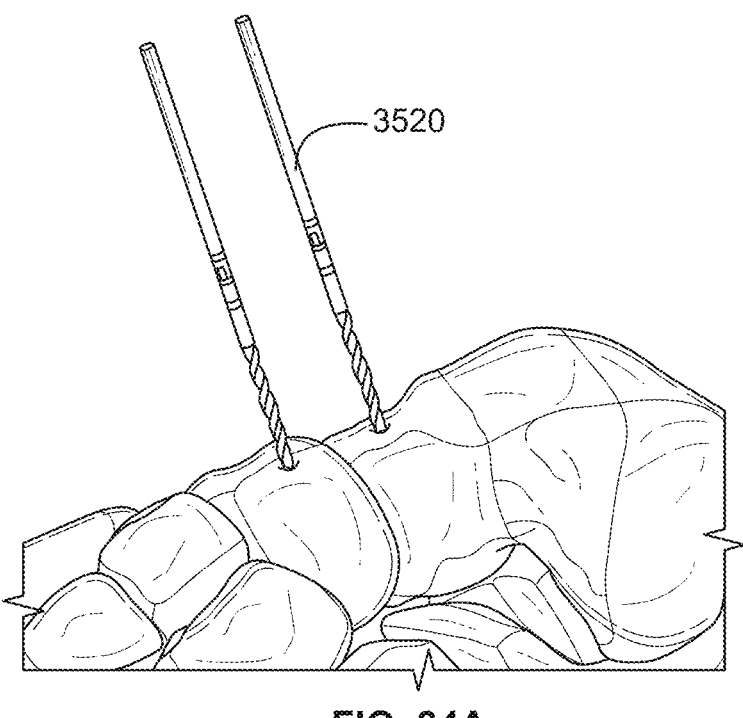

FIG. 34A is a perspective view of a foot and two short drill pins according to an embodiment of the present disclosure.

Figure 34B:
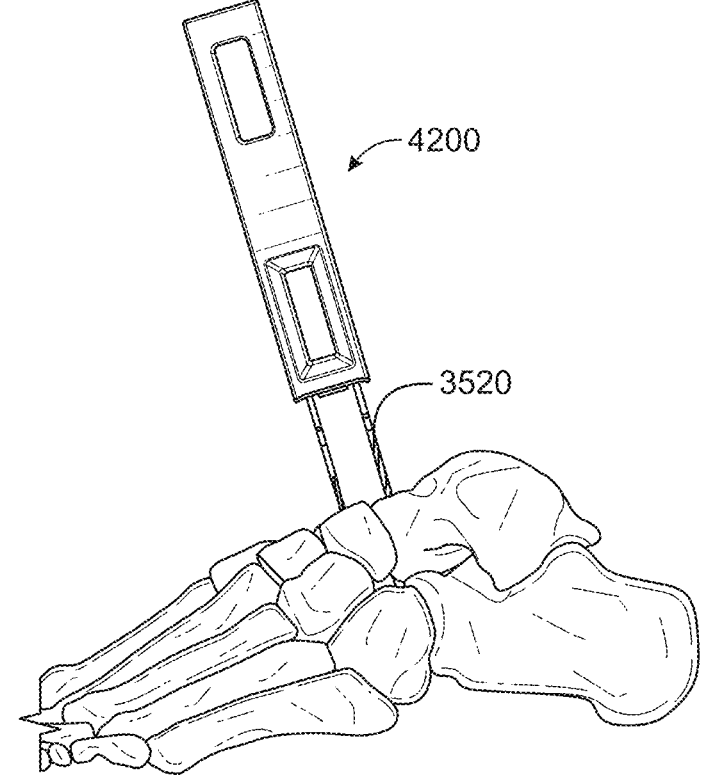

FIG. 34B is a perspective view of the foot, the two short drill pins, and an impactor according to an embodiment of the present disclosure.

Figure 35A:
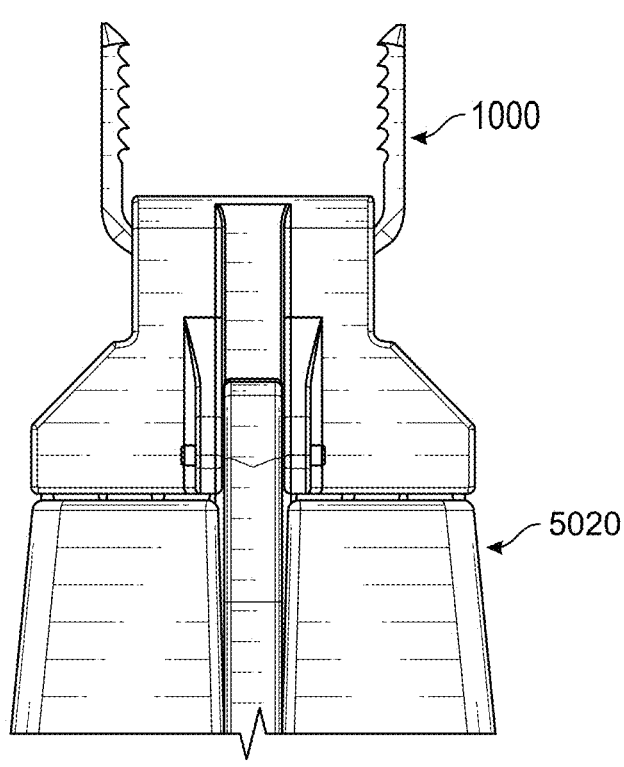

FIG. 35A is a partial front view of an inserter and a compression staple according to an embodiment of the present disclosure.

Figure 35B:
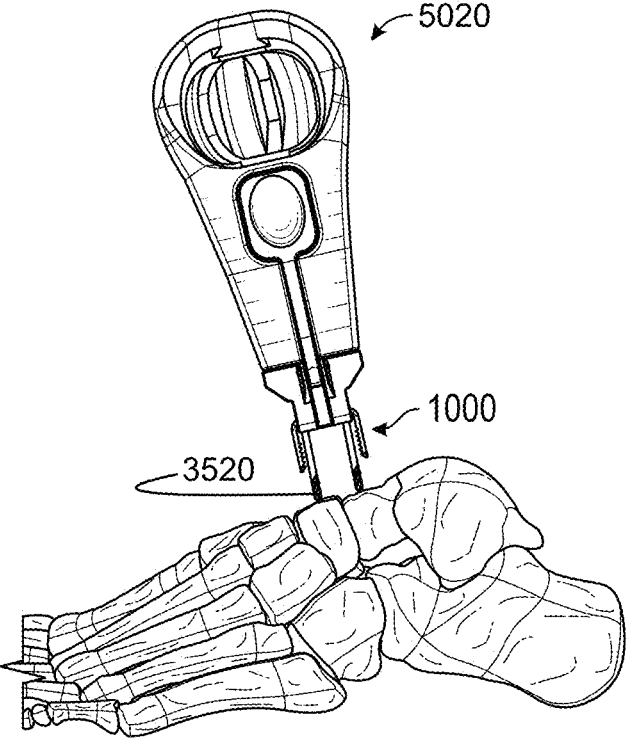

FIG. 35B is a perspective view of the inserter, the compression staple, two short drill pins, and a foot according to an embodiment of the present disclosure.

FIG. 36A is a perspective view of an inserter, two short drill pins, a compression staple, and a foot according to an embodiment of the present disclosure.

FIG. 36B is a perspective view of the inserter, the two short drill pins, the compression staple and the foot of FIG. 36A.

FIG. 36C is a perspective view of the inserter, the two short drill pins, the compression staple and the foot of FIG. 36A.

FIG. 36D is a perspective view of the inserter, the two short drill pins, the compression staple and the foot of FIG. 36A.

FIG. 36E is a perspective view of the inserter, the two short drill pins, the compression staple and the foot of FIG. 36A.

FIG. 36F is a perspective view of the inserter, the two short drill pins, the compression staple and the foot of FIG. 36A.

Figure 37:
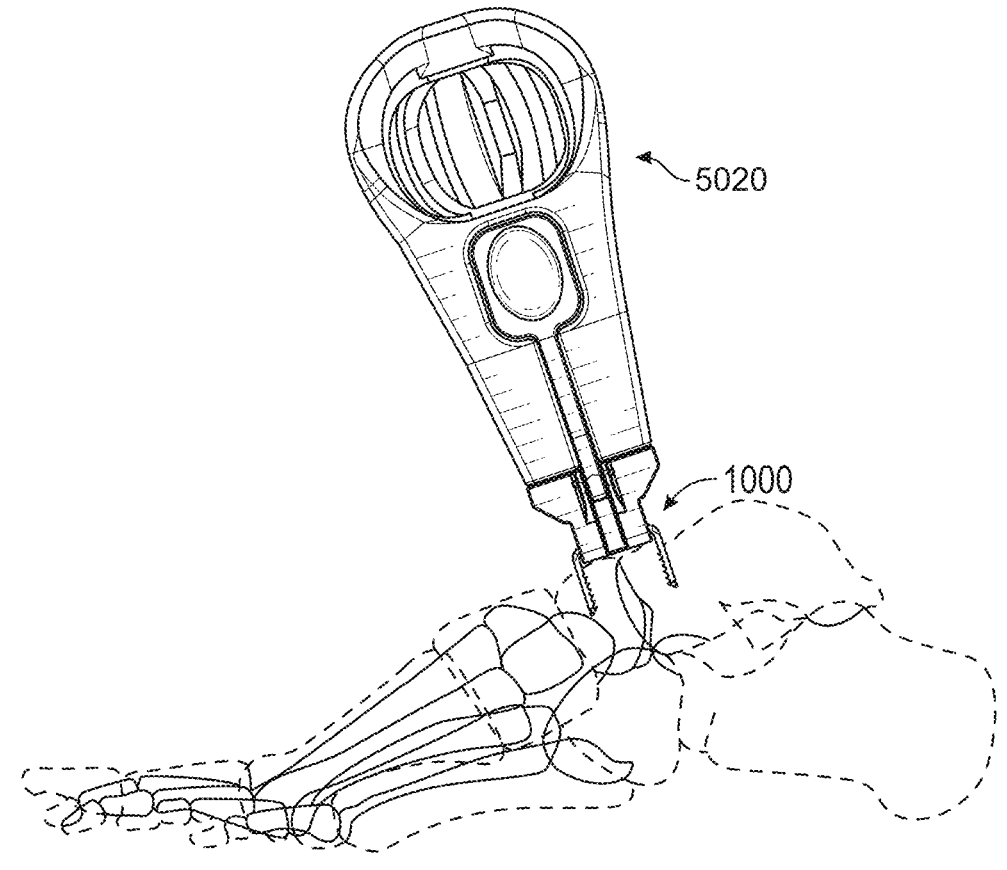

FIG. 37 is a perspective view of an inserter, a compression staple, and a foot according to an embodiment of the present disclosure.

Figures 38A, 38B, 38C:
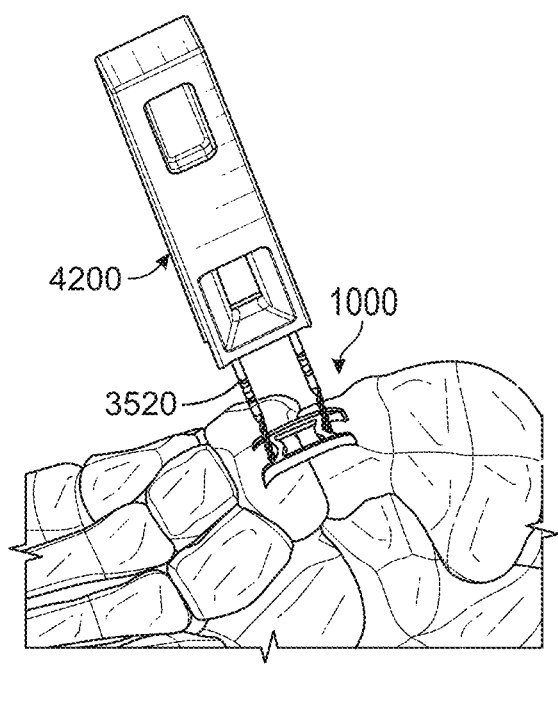

FIG. 38A is a perspective view of an impactor, a compression staple, two short drill pins, and a foot according to an embodiment of the present disclosure.

FIG. 38B is a perspective view of the foot and the compression staple of FIG. 38A.

FIG. 38C is a perspective view of the foot and the compression staple of FIG. 38A.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the devices, systems, and methods, as represented in the drawings, is not intended to limit the scope of the present disclosure but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means towards the front of a body. Posterior means towards the back of a body. Superior or cephalad means towards the head. Inferior or caudal means towards the feet or tail. Medial means towards the midline of a body, particularly towards a plane of bilateral symmetry of the body. Lateral means away from the midline of a body or away from a plane of bilateral symmetry of the body. Axial means towards a central axis of a body. Abaxial means away from a central axis of a body. Ipsilateral means on the same side of the body. Contralateral means on the opposite side of the body. Proximal means towards the trunk of the body. Proximal may also mean towards a user or operator. Distal means away from the trunk. Distal may also mean away from a user or operator. Dorsal means towards the top of the foot. Plantar means towards the sole of the foot. Varus means deviation of the distal part of the leg below the knee inwards, resulting in a bowlegged appearance. Valgus means deviation of the distal part of the leg below the knee outward, resulting in a knock-kneed appearance.

The present disclosure relates to compression staple systems and methods for bone fixation. Those skilled in the art will recognize that the following description is merely illustrative of the principles of the technology, which may be applied in various ways to provide many alternative embodiments. It will be understood that other variations and uses are contemplated, including, but not limited to, hand bone fragment osteotomy fixation, foot bone fragment osteotomy fixation, joint arthrodesis in the hand, joint arthrodesis in the foot, and/or other indications for which two portions of bone are intended to be fixed relative to each other.

FIG. 1A is a perspective view of a compression staple 1000 according to an embodiment of the present disclosure. FIG. 1B is a top perspective view of the compression staple 1000, FIG. 1C is a side perspective view of the compression staple 1000, and FIG. 1D is a front perspective view of the compression staple 1000. The compression staple 1000 may be configured to provide compression between two adjacent bone and/or two adjacent bone fragments. The compression staple 1000 may be configured for hand bone fragment osteotomy fixation, foot bone fragment osteotomy fixation, joint arthrodesis in the hand, and/or joint arthrodesis in the foot. The compression staple 1000 may be configured as a single-use bone fixation appliance and may be configured for permanent implantation.

The compression staple 1000 may include four legs 1002. The four legs 1002 may be arranged in a generally rectangular pattern such that the compression staple 1000 may include two front legs, two back legs, two first side legs, and two second side legs. A first bridge 1007 may extend between the two front legs 1002 and a second bridge 1007 may extend between the two back legs 1002. The first bridge 1007 may include a bone facing side 1026 from which the two front legs 1002 extend. The second bridge 1007 may also include a bone facing side 1026 from which the two back legs 1002 extend. A first crossbar 1003 may extend between the two first side legs 1002 and a second crossbar 1003 may extend between the two second side legs 1002.

Alternatively, the compression staple 1000 may include two legs 1002. The bridge 1007 may extend between the two legs 1002. The bridge 1007 may include a bone facing side 1026 from which the two legs 1002 extend.

The use of the terms front, back, first side, and second side are used herein to describe the position of the four legs relative to each other. The terms are not intended to imply a specific orientation of the compression staple 1000 relative to a patient's body. The compression staple 1000 may have any orientation relative to a patient's body. The orientation of the compression staple 1000 may be based on patient anatomy and/or assessment of clinical indications by a clinician.

Alternatively, the four legs 1002 may be arranged in a generally trapezoidal pattern. Alternatively, the four legs 1002 may be arranged in a generally parallelogrammatic pattern. Alternatively, the four legs 1002 may be arranged in any other quadrilateral pattern.

The bridge 1007 may include an arched portion 1006. The arched portion 1006 may be configured such that the center of the arched portion 1006 may generally align with a central plane of the compression staple 1000. Additionally, the arched portion 1006 may extend superiorly such that the center of the arched portion 1006 may be at a further distance from the legs 1002 than the ends of the arched portion 1006.

Each of the four legs 1002 may include a leading end 1004 and a plurality of teeth 1001. The leading end 1004 may be located at the end of each of the legs 1002 that is opposite the bridge 1007 and crossbar 1003. The leading end 1004 may be tapered and/or rounded to ease insertion of the legs 1002 into an aperture in a bone.

The plurality of teeth 1001 may be oriented generally inwards. The plurality of teeth 1001 may be oriented towards the bridge 1007. Each of the plurality of teeth 1001 may include a ramp portion and a ledge portion. The plurality of teeth 1001 may be configured to inhibit the compression staple 1000 from withdrawing from the bone after being implanted into the bone.

The compression staple 1000 may also include a pin notch 1005 and a central aperture 1008. The central aperture 1008 may be formed by the first bridge 1007, the second bridge 1007, the first crossbar 1003, and the second crossbar 1003. The central aperture 1008 may be generally symmetrical about a plane located equidistant between the first bridge 1007 and the second bridge 1007. The central aperture 1008 may also be generally symmetrical about a plane located equidistant between the first crossbar 1003 and the second crossbar 1003.

Each of the first crossbar 1003 and the second crossbar 1003 may be angled inwards towards the central aperture 1008, thereby defining a first pin notch 1005 and a second pin notch 1005. The pin notch 1005 may be configured to receive a short drill pin between two adjacent legs 1002. The pin notch 1005 may further be configured to receive a short drill pin between the legs 1002 and the central aperture 1008.

The compression staple 1000 may include a bridge length 1020, a bridge width 1022, and a leg length 1025. The bridge length 1020 may be a distance between two adjacent legs 1002 that are connected by a bridge 1007. The bridge width 1022 may be a distance between two adjacent legs 1002 that are connected by a crossbar 1003. The leg length 1025 may be a length along a leg 1002 from the bridge 1007 to the leading end 1004.

The compression staple 1000 may be configured such that the bridge length 1020 is within a range of lengths from 12 mm to 28 mm. The compression staple 1000 may further be configured such that the leg length 1025 is within a range of lengths from 12 mm to 32 mm. In an embodiment, the compression staple 1000 may be one of a set of differently-sized compression staples, each having a different bridge length 1020 and/or a different leg length 1025.

The compression staple 1000 may have a collapsed state in which the second side legs 1002 are angled inwards towards the first side legs 1002 and/or the first side legs 1002 are angled inwards towards the second side legs 1002. The compression staple 1000 may also have a distracted state in which the second side legs 1002 are generally parallel to the first side legs 1002. The compression staple 1000 may be transitionable between the distracted state and the collapsed state.

The compression staple 1000 may be configured so that a force may be applied to the arched portion 1006 to transition the compression staple 1000 from the collapsed state to the distracted state. Additionally, upon removal of the force, the compression staple 1000 will be biased to return to the collapsed state from the distracted state, thereby exerting a compressive force on any matter between the second side legs 1002 and the first side legs 1002.

The compression staple 1000 may be manufactured from a shape memory alloy to facilitate the bias towards the collapsed state from the distracted state. The shape memory alloy may include a nickel titanium alloy.

Figures 2A, 2B, 2C, 2D:
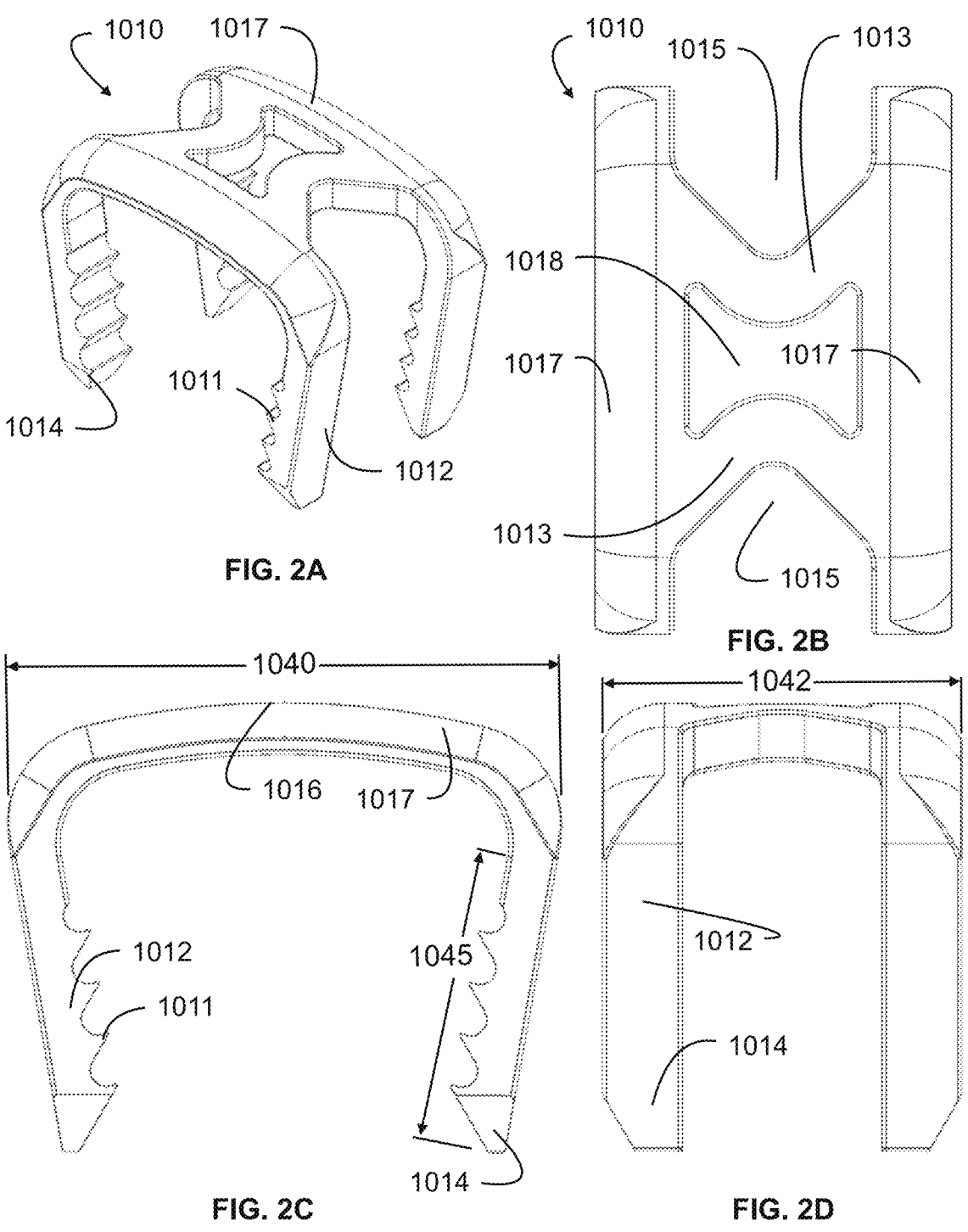
FIG. 2A is a perspective view of a compression staple according to an embodiment of the present disclosure.
FIG. 2B is a top view of the compression staple of FIG. 2A.
FIG. 2C is a front view of the compression staple of FIG. 2A.
FIG. 2D is a side view of the compression staple of FIG. 2A.

FIG. 2A is a perspective view of a compression staple 1010 according to an embodiment of the present disclosure. FIG. 2B is a top view of the compression staple 1010, FIG. 2C is a front view of the compression staple 1010, and FIG. 2D is a side view of the compression staple 1010. Various parts of the compression staple 1010 may be identical or similar to their counterparts on the compression staple 1000 and/or other compression staple embodiments presented herein; these parts may not be described again here. All statements made regarding the compression staple 1000 may apply to the compression staple 1010 unless they would be contradicted by the differences between the two.

The compression staple 1010 may include legs 1012, crossbars 1013, bridges 1017, and a central aperture 1018. The legs 1012 may include a leading end 1014, a plurality of teeth 1011, and a leg length 1045. The bridge 1017 may include an arched portion 1016, a pin notch 1015, a bridge length 1040, and a bridge width 1042. The bridge width 1042 may be generally equal to the bridge width 1022 of compression staple 1000. The bridge length 1040 may be less than the bridge length 1020 of compression staple 1000 and may result in the central aperture 1018 being smaller than the central aperture 1008. The leg length 1045 may be less than the leg length 1025 and may result in fewer teeth in the plurality of teeth 1011 compared to the plurality of teeth 1001.

Figures 3A, 3B, 3C, 3D:
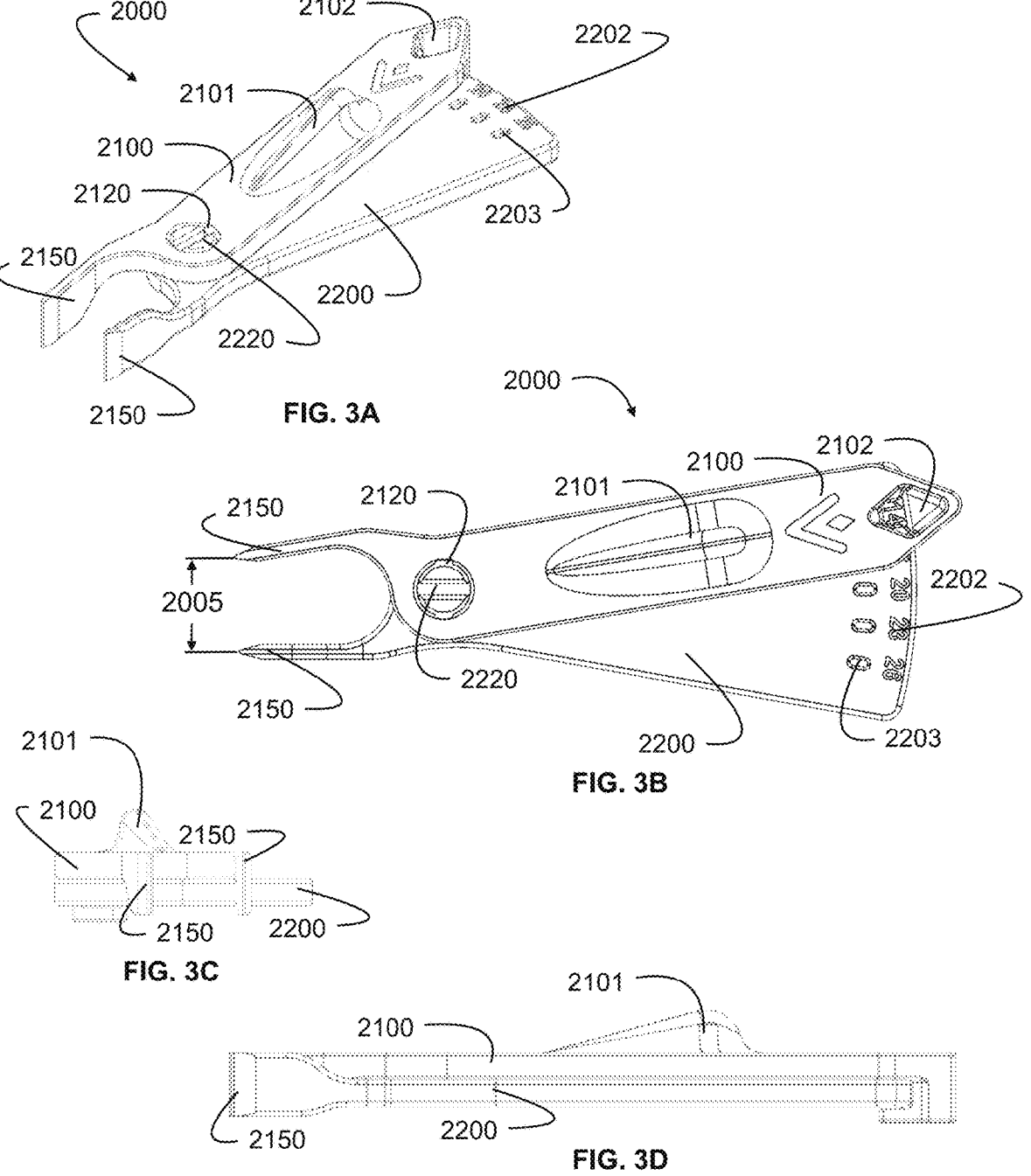
FIG. 3A is a perspective view of a sizer according to an embodiment of the present disclosure.
FIG. 3B is a top view of the sizer of FIG. 3A.
FIG. 3C is a front view of the sizer of FIG. 3A.
FIG. 3D is a side view of the sizer of FIG. 3A.

FIG. 3A is a perspective view of a sizer 2000 according to an embodiment of the present disclosure. FIG. 3B is a top view of the sizer 2000, FIG. 3C is a front view of the sizer 2000, and FIG. 3D is a side view of the sizer 2000. The sizer 2000 may be configured to define the bridge length 1020 and the bridge width 1022 for each compression staple 1000 of a set of differently-sized compression staples.

In an embodiment, the set of differently sized compression staples may include a compression staple 1000 with a bridge length 1020 of approximately 14 mm, a compression staple 1000 with a bridge length 1020 of approximately 17 mm, a compression staple 1000 with a bridge length 1020 of approximately 20 mm, a compression staple 1000 with a bridge length 1020 of approximately 23 mm, and a compression staple 1000 with a bridge length 1020 of approximately 26 mm.

FIGS. 4A-4E are perspective views of the sizer 2000. The sizer 2000 may include a setting for each bridge length 1020 included in the set of differently sized compression staples

1000. The sizer 2000 may include tactile user feedback and an audible click when moving between size settings.

Figures 4A, 4B, 4C, 4D, 4E:
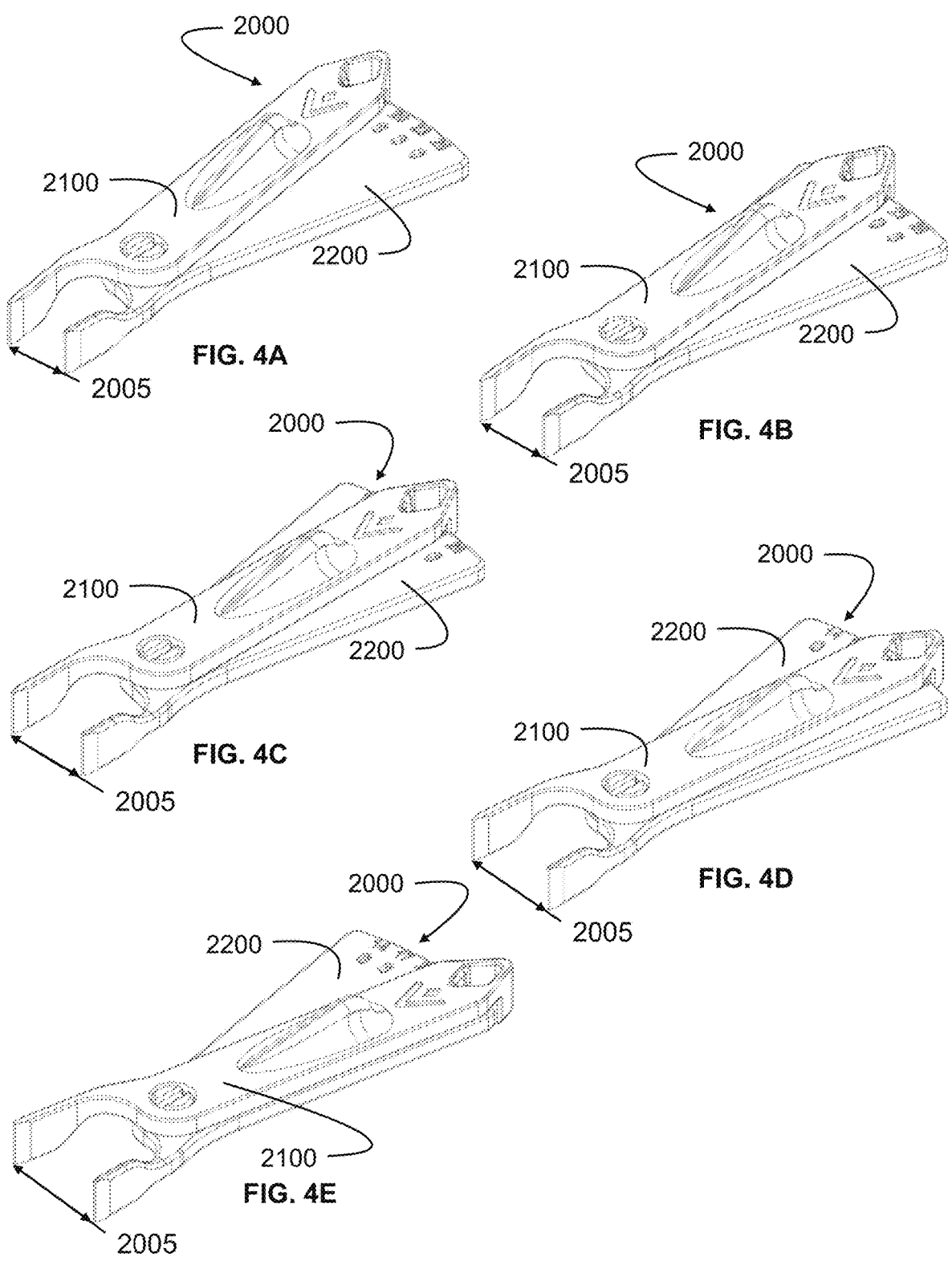
FIGS. 4A-4E are perspective views of the sizer of FIG. 3A

The sizer 2000 may include a jaw spacing 2005 that may correspond to a specific size settings and the associated indicator. For example, with the sizer 2000 adjusted to a setting indicated by "14", the jaw spacing 2005 may be approximately 14 mm (as shown in FIG. 4A) or with the sizer 2000 adjusted to a setting indicated by "20", the jaw spacing 2005 may be approximately 20 mm (as shown in FIG. 4C).

The sizer 2000 may include a sizer dial 2100 and a sizer plate 2200. The sizer dial 2100 may be rotatably coupled to the sizer plate 2200. The sizer dial 2100 may rotate relative to the sizer plate 2200 to align with each of the size settings. The sizer dial 2100 may include a top surface 2111 and a bottom surface 2112. The sizer plate 2200 may include a top surface 2211 and a bottom surface 2212. When the sizer is assembled, the bottom surface 2112 of the sizer dial 2100 may be proximate the top surface 2211 of the sizer plate 2200.

Figures 5A, 5B, 5C, 5D:
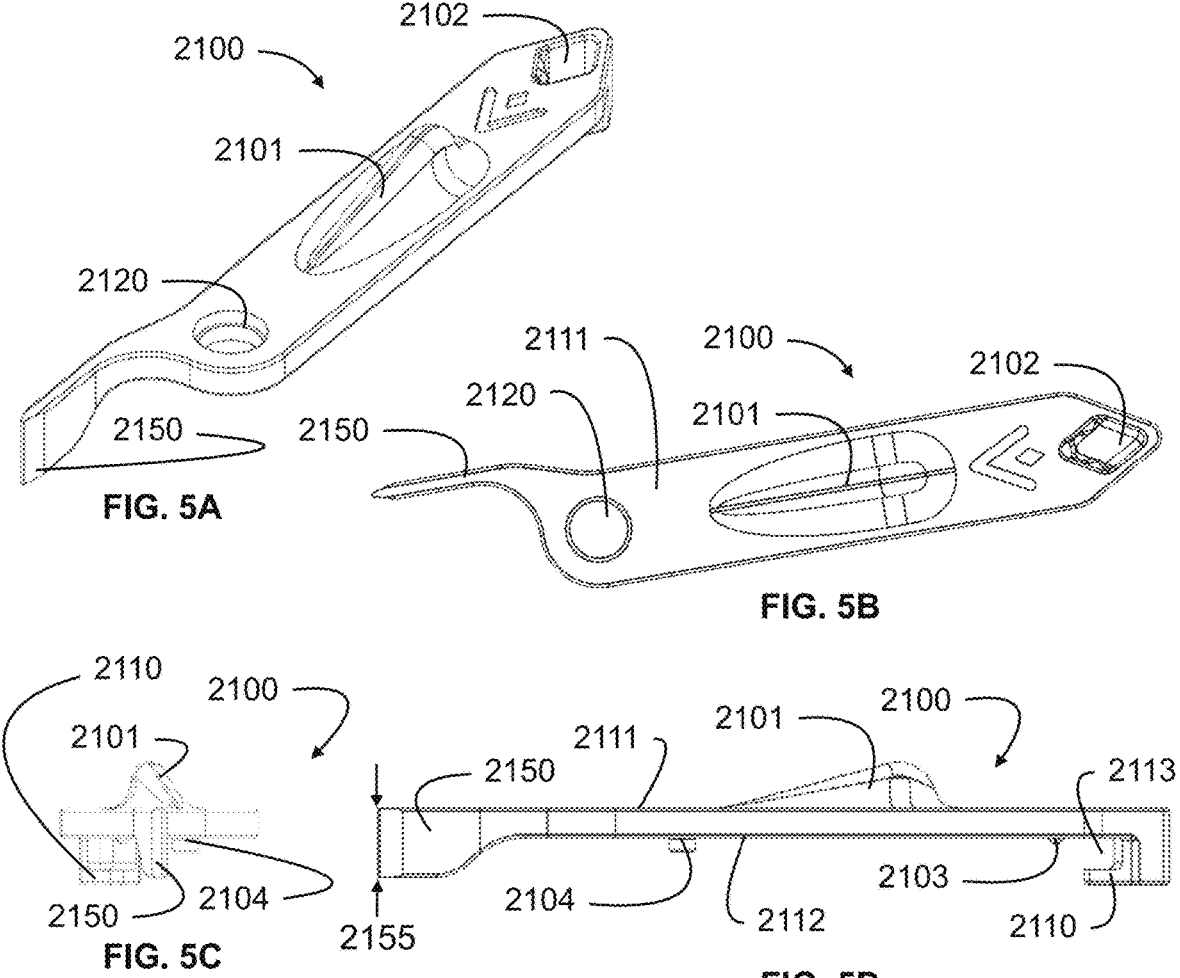
FIG. 5A is a perspective view of a sizer dial according to an embodiment of the present disclosure.
FIG. 5B is a top view of the sizer dial of FIG. 5A.
FIG. 5C is a front view of the sizer dial of FIG. 5A.
FIG. 5D is a side view of the sizer dial of FIG. 5A.

FIG. 5A is a perspective view of the sizer dial 2100 according to an embodiment of the present disclosure. FIG. 5B is a top view of the sizer dial 2100, FIG. 5C is a front view of the sizer dial 2100, and FIG. 5D is a side view of the sizer dial 2100. The sizer dial 2100 may include an adjustment handle 2101, a size indicator aperture 2102, a sizing boss 2103, a travel limit boss 2104, an interlocking feature 2110, a female rotation feature 2120, and a first sizing tip 2150.

The adjustment handle 2101 may extend from the top surface 2111 of the sizer dial 2100. The adjustment handle 2101 may be engaged by a user to rotate the sizer dial 2100 relative to the sizer plate 2200 in both a clockwise and a counter-clockwise direction.

The size indicator aperture 2102 may provide visibility through the sizer dial 2100 so that a staple size indicator 2202 of the sizer plate 2200 may be seen by the user. The size indicator aperture 2102 may be sized so that only a single staple size indicator 2202 may be visible at each specific size setting of the sizer 2000. With the sizer 2000 adjusted to a specific size setting, the staple size indicator 2202 that may be visible through the size indicator aperture 2102 may correspond to the jaw spacing 2005 associated with the specific size setting.

The sizing boss 2103 may be configured to be received by a sizing aperture 2203 of the sizer plate 2200. The sizing boss 2103 may extend from the bottom surface 2112 of the sizer dial 2100. Alternatively, a sizing boss may extend from the top surface 2211 of the sizer plate 2200 and a sizing aperture may extend from a bottom surface 2112 of the sizer dial 2100.

When received in a sizing aperture 2203, the sizing boss 2103 may inhibit rotation of the sizer dial 2100 relative to the sizer plate 2200. However, with sufficient torque applied to the adjustment handle 2101, the sizing boss 2103 may disengage from a first sizing aperture 2203, thereby allowing the sizer dial 2100 to rotate relative to the sizer plate 2200 and subsequently may allow the sizing boss 2103 to be received in a second sizing aperture 2203.

The sizing boss 2103 and the sizing aperture 2203 may be configured so that, with the sizing boss 2103 received in the sizing aperture 2203, a single staple size indicator 2202 may be visible through the size indicator aperture 2102. The sizing boss 2103 and the sizing aperture 2203 may be configured so that as the sizing boss 2103 is received in the sizing aperture, tactile user feedback and an audible click may be generated.

The travel limit boss 2104 may extend from the bottom surface 2112. The travel limit boss 2104 may be configured to be received by a travel limit recess 2204 of the sizer plate 2200. When received in the travel limit recess 2204, the travel limit boss 2104 may restrict rotation of the sizer dial 2100 relative to the sizer plate 2200. The travel limit boss 2104 and the travel limit recess 2204 may be configured so that a permitted range of travel may include all of the size settings of the sizer 2000. Alternatively, a travel limit boss may extend from the top surface 2211 of the sizer plate 2200 and a travel limit recess may extend from a bottom surface 2112 of the sizer dial 2100.

The interlocking feature 2110 may extend from the bottom surface 2112 and may form a channel 2113 configured to receive a proximal end 2213 of the sizer plate 2200. The interlocking feature 2110 may inhibit the sizer dial 2100 from deflecting away from the sizer plate 2200, thereby inhibiting disengagement of the sizing boss 2103 from the sizing aperture 2203. The interlocking feature 2110 may be further configured so that, with sufficient torque applied to the adjustment handle 2101, the interlocking feature 2110 may allow the sizing boss 2103 to disengage from a first sizing aperture 2203, thereby allowing the sizer dial 2100 to rotate relative to the sizer plate 2200 and subsequently may allow the sizing boss 2103 to be received in a second sizing aperture 2203.

The female rotation feature 2120 may be configured to receive a male rotation feature 2220 to form a hinge between the sizer dial 2100 and the sizer plate 2200 to facilitate rotation of the sizer dial 2100 relative to the sizer plate 2200. The female rotation feature 2120 and the male rotation feature 2220 may be configured with a snap fit feature so that the sizer dial 2100 may snap onto the sizer plate 2200. The sizer dial 2100 may be captive on the sizer plate 2200 after assembly.

The first sizing tip 2150 may include a first tip height 2155. With the sizer 2000 assembled, the distance between the first sizing tip 2150 and a second sizing tip 2250 of the sizer plate 2200 may be defined as the jaw spacing 2005. The first tip height 2155 may be generally equal to the bridge width 1022 of the compression staple 1000 and/or the bridge width 1042 of the compression staple 1010.

FIG. 6A is a perspective view of a sizer plate 2200 according to an embodiment of the present disclosure. FIG. 6B is a top view of the sizer plate 2200, FIG. 6C is a front view of the sizer plate 2200, and FIG. 6D is a side view of the sizer plate 2200. The sizer plate 2200 may include a staple size indicator 2202, a plurality of sizing aperture 2203, a travel limit recess 2204, a proximal end 2213, a male rotation feature 2220, and a second sizing tip 2250.

The staple size indicator 2202 may be visible through the size indicator aperture 2102. The staple size indicator 2202 may be sized so that only a single staple size indicator 2202 may be visible through the size indicator aperture 2102 at each specific size setting of the sizer 2000. With the sizer 2000 adjusted to a specific size setting, the staple size indicator 2202 that may be visible through the size indicator aperture 2102 may correspond to the jaw spacing 2005 associated with the specific size setting.

The sizing aperture 2203 may be configured to receive the sizing boss 2103. The sizing aperture 2203 may extend from the top surface 2211 towards the bottom surface 2212. The sizer plate 2200 may include a plurality of sizing apertures 2203 corresponding to a plurality of staple size indicators 2202. In an embodiment, the sizer plate 2200 may include five sizing apertures 2203 and five staple size indicators 2202.

The travel limit recess 2204 may extend from the top surface 2211 towards the bottom surface 2212. The travel limit recess 2204 may be configured to receive the travel limit boss 2104. When received in the travel limit recess 2204, the travel limit boss 2104 may restrict rotation of the sizer dial 2100 relative to the sizer plate 2200. The travel limit boss 2104 and the travel limit recess 2204 may be configured so that a permitted range of travel may include all of the size settings of the sizer 2000.

The proximal end 2213 may be configured to be received in the interlocking feature 2110 to prevent deflection of the sizer dial 2100 away from proximal end 2213. The proximal end 2213 may include the staple size indicators 2202 and the sizing apertures 2203.

The male rotation feature 2220 may be configured to be received in the female rotation feature 2120 to form a hinge between the sizer dial 2100 and the sizer plate 2200 to facilitate rotation of the sizer dial 2100 relative to the sizer plate 2200. The female rotation feature 2120 and the male rotation feature 2220 may be configured with a snap fit feature so that the sizer dial 2100 may snap onto the sizer plate 2200. The sizer dial 2100 may be captive on the sizer plate 2200 after assembly.

The second sizing tip 2250 may include a second tip height 2255. With the sizer 2000 assembled, the distance between the first sizing tip 2150 and the second sizing tip 2250 may be defined as the jaw spacing 2005. The second tip height 2255 may be generally equal to the bridge width 1022 of the compression staple 1000 and/or the bridge width 1042 of the compression staple 1010.

Figures 7A, 7B, 7C, 7D:
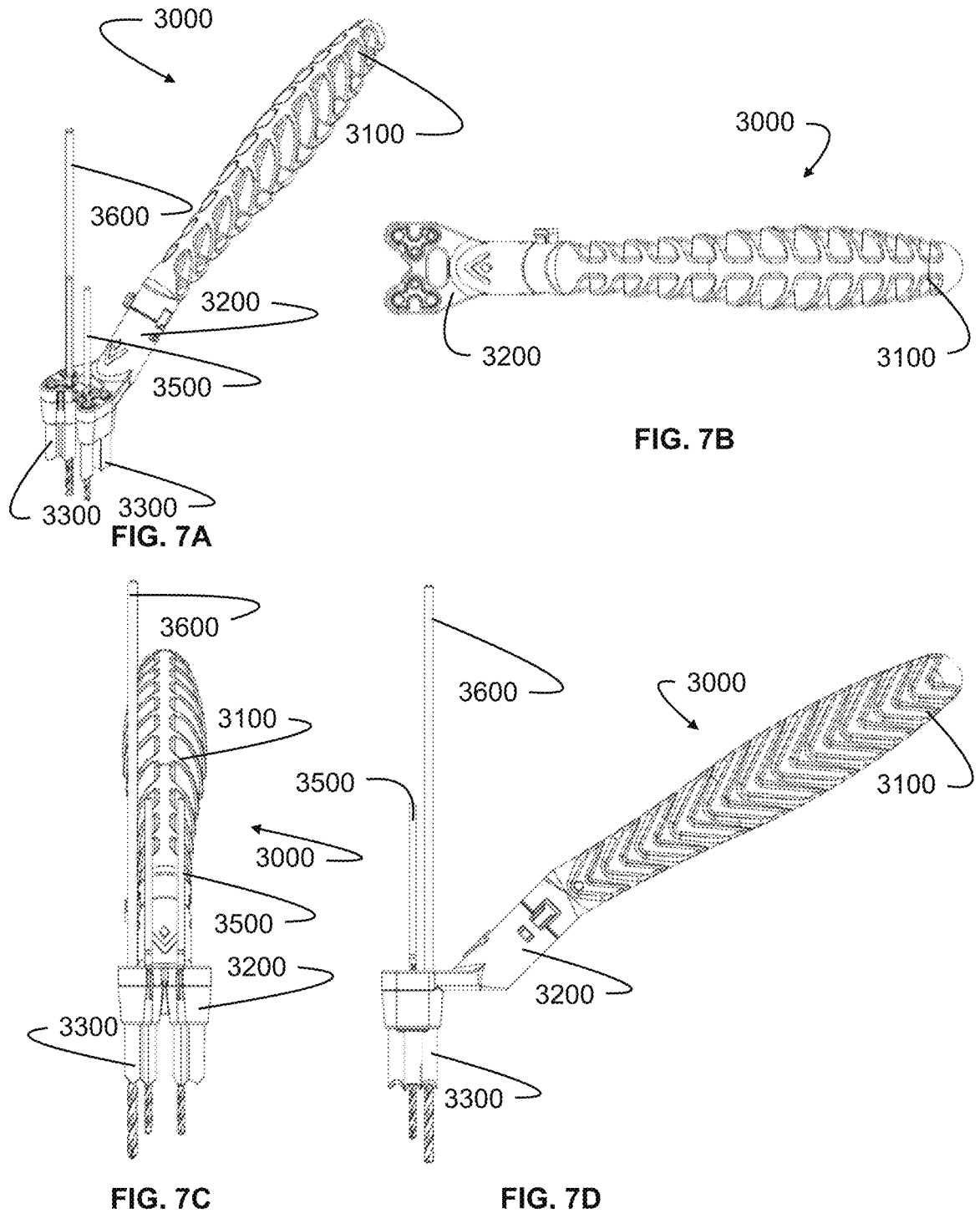
FIG. 7A is a perspective view of a drill guide, short drill pins, and a long drill according to an embodiment of the present disclosure.
FIG. 7B is a top view of the drill guide, the short drill pins, and the long drill of FIG. 7A.
FIG. 7C is a front view of the drill guide, the short drill pins, and the long drill of FIG. 7A.
FIG. 7D is a side view of the drill guide, the short drill pins, and the long drill of FIG. 7A.

FIG. 7A is a perspective view of a drill guide 3000, short drill pins 3514, and a long drill 3614 according to an embodiment of the present disclosure. FIG. 7B is a top view of the drill guide 3000, the short drill pins 3514, and the long drill 3614, FIG. 7C is a front view of the drill guide 3000, the short drill pins 3514, and the long drill 3614, and FIG. 7D is a side view of the drill guide 3000, the short drill pins 3514, and the long drill 3614.

The drill guide 3000 may be configured to guide placement of the short drill pin 3514 and the long drill 3614. The drill guide 3000 may include spring-loaded guide sleeves having independent action. The drill guide 3000 may be configured such that a plurality of drill trajectories may be held parallel relative to each other while independently allowing the guide sleeves to slide within the drill guide 3000. The drill guide 3000 may be configured to allow the plurality of drill trajectories to be parallel to a joint line. The drill trajectories may not necessarily be perpendicular to a local bone surface.

The drill guide 3000 may be configured so that a first longitudinal axis of a first guide sleeve and a second longitudinal axis of a second guide sleeve are parallel regardless of an angle between the first longitudinal axis of the first guide sleeve and/or the second longitudinal axis of the second guide sleeve and the bone surface. The drill guide 3000 may be configured to facilitate creation of a local (immediately under where the staple bridge 1007 will reside) bone surface that may be perpendicular to the trajectory of the long drills 3600 (and subsequently the staple legs 1002), such that the staple bridge 1007 may sit flush against the local bone surface.

The drill guide 3000 may include a handle 3100 and foot portion 3200. The foot portion 3200 may be configured to be coupled to the handle 3100. The foot portion 3200 may be one of a set of differently-sized foot portions 3200, each corresponding to one of a set of differently-sized compression staples 1000, each having a different bridge length 1020. The drill guide 3000 may be delivered to a user with the foot portion 3200 assembled with the handle 3100. Alternatively, the drill guide 3000 may be delivered to the user disassembled in a kit with a handle 3100 and a set of differently-sized foot portions 3200, each corresponding to one of a set of differently-sized compression staples 1000 each having a different bridge length 1020.

FIG. 8A is a perspective view of the drill guide 3000, the short drill pins 3514, and the long drill 3614. The drill guide 3000 of FIG. 8A may include a foot portion 3200 sized to correspond to a compression staple 1000 with a bridge length 1020 of approximately 14 mm.

FIG. 8B is a perspective view of a drill guide 3010, the short drill pins 3517, and the long drill 3617. The drill guide 3010 of FIG. 8B may include a foot portion 3200 sized to correspond to a compression staple 1000 with a bridge length 1020 of approximately 17 mm.

FIG. 8C is a perspective view of a drill guide 3020, the short drill pins 3520, and the long drill 3620. The drill guide 3020 of FIG. 8C may include a foot portion 3200 sized to correspond to a compression staple 1000 with a bridge length 1020 of approximately 20 mm.

FIG. 8D is a perspective view of a drill guide 3030, the short drill pins 3523, and the long drill 3623. The drill guide 3030 of FIG. 8D may include a foot portion 3200 sized to correspond to a compression staple 1000 with a bridge length 1020 of approximately 23 mm.

FIG. 8E is a perspective view of a drill guide 3040, the short drill pins 3526, and the long drill 3626. The drill guide 3040 of FIG. 8E may include a foot portion 3200 sized to correspond to a compression staple 1000 with a bridge length 1020 of approximately 26 mm.

Various parts of the drill guide 3000 may be identical or similar to their counterparts on the drill guide 3010, the drill guide 3020, the drill guide 3030, the drill guide 3040, and/or other drill guide embodiments presented herein; these parts may not be described again here. All statements made regarding the drill guide 3000 may apply to all drill guides described herein, unless they would be contradicted by the differences between the two FIG. 9A is a perspective view of a handle 3100 according to an embodiment of the present disclosure. FIG. 9B is a top view of the handle 3100, FIG. 9C is a front view of the handle 3100, and FIG. 9D is a side view of the handle 3100. The handle 3100 may include a grip 3101 and an attachment feature 3102.

The grip 3101 may be used to hold the foot portion 3200 securely in a desired location on a surface of a bone to help ensure accurate drill hole locations based on patient anatomy and clinical indications. The grip 3101 may include an ergonomic profile. The grip 3101 may include features that may be conducive to additive manufacturing and/or injection molding.

The attachment feature 3102 may be configured to be received in an attachment feature 3202 of the foot portion 3200. The attachment feature 3102 and the attachment feature 3202 may be configured so that the attachment feature 3202 may receive the attachment feature 3102 in a single orientation. Alternatively, the attachment feature 3102 and the attachment feature 3202 may be configured so that the attachment feature 3202 may receive the attachment feature 3102 in two distinct orientations that are spaced approximately 180 degrees apart from each other. The attachment feature 3102 and the attachment feature 3202 may be configured with a snap fit mechanism so that the handle 3100 may snap into the foot portion 3200.

The attachment feature 3102 may include an engagement feature 3104 and a button 3103. During insertion of the attachment feature 3102 into attachment feature 3202, the engagement feature 3104 may be deflected, by the attachment feature 3202, inwards from an initial position to a deflected position, until the attachment feature 3102 is fully received within the attachment feature 3202. Alternatively, the button 3103 may be depressed, thereby moving the engagement feature 3104 from the initial position to the deflected position. The button 3103 may be released when the attachment feature 3102 is fully received within the attachment feature 3202, thereby returning the engagement feature 3104 to the initial position.

With the attachment feature fully received within the attachment feature 3202, the engagement feature 3104 may return to the initial position, thereby engaging a snap fit mechanism securing the handle 3100 to the foot portion 3200. Depression of the button 3103 may move the engagement feature 3104 from the initial position to the deflected position, and thereby disengage the snap fit mechanism of the attachment feature 3102 and allow the handle 3100 to disengage from the foot portion 3200.

FIG. 10A is a perspective view of a foot portion 3200 according to an embodiment of the present disclosure. FIG. 10B is a top view of the foot portion 3200, FIG. 10C is a front view of the foot portion 3200, and FIG. 10D is a side view of the foot portion 3200. The foot portion 3200 may be configured to receive the handle 3100. The foot portion may further be configured to receive one or more guide sleeves 3300. The foot portion 3200 may include a base portion 3220, an aperture 3204, and a stem 3210.

The base portion may include an attachment feature 3202 and an engagement aperture 3206. The attachment feature 3202 may be configured to receive the attachment feature 3102. The attachment feature 3102 and the attachment feature 3202 may be configured so that the attachment feature 3202 may receive the attachment feature 3102 in a single orientation. Alternatively, the attachment feature 3102 and the attachment feature 3202 may be configured so that the attachment feature 3202 may receive the attachment feature 3102 in two distinct orientations that are spaced approximately 180 degrees apart from each other. The attachment feature 3102 and the attachment feature 3202 may be configured with a snap fit mechanism so that the handle 3100 may snap into the foot portion 3200.

The engagement aperture 3206 may be configured to receive the engagement feature 3104 as part of the snap fit mechanism configured to secure the handle 3100 to the foot portion 3200. The aperture 3204 may be configured to provide visibility through the foot portion 3200 to a surgical site. The aperture 3204 may aid in accurate placement of the drill guide 3000 on a surface of a bone.

The stem 3210 may include one or more guide sleeve apertures 3201. The one or more guide sleeve apertures 3201 may be configured to receive one or more guide sleeves 3300. In an embodiment, the foot portion 3200 may include two guide sleeve apertures 3201 configured to receive two guide sleeves 3300. The two guide sleeve apertures 3201 may be separated by an aperture spacing 3208. The aperture spacing 3208 may correspond to a bridge length 1020 of the compression staple 1000.

The foot portion 3200 may be one of a set of differently-sized foot portions 3200, each having a different aperture spacing 3208, wherein the aperture spacing 3208 may correspond to one of a set of differently-sized compression staples 1000 each having a different bridge length 1020.

Each guide sleeve aperture 3201 may include a post 3203, a slot 3205, and a tab 3207. The post 3203 may be partially encircled by the slot 3205, thereby allowing the post 3203 to deflect outward from an initial position to a deflected position and return to the initial position. The post may be configured to be received within a groove of the guide sleeve 3300. The post 3203 may be moved to a deflected position to facilitate insertion of the guide sleeve 3300 into the guide sleeve aperture 3201. When the post 3203 aligns with the groove 3303, the post 3203 may return to the initial position thereby making the guide sleeve 3300 slidably captive within the guide sleeve aperture 3201.

The tab 3207 may extend into the guide sleeve aperture 3201. The tab 3207 may be configured so that, with a guide sleeve 3300 slidably captive within the guide sleeve aperture 3201, a first end 3402 of a compression spring 3400 may abut the tab 3207 and a second end 3404 of the compression spring 3400 may abut a ledge 3304 of the guide sleeve 3300, thereby biasing a bone contacting end of the guide sleeve 3300 distally away from the foot portion 3200.

FIG. 11A is a perspective view of a guide sleeve 3300 according to an embodiment of the present disclosure. FIG. 11B is a top view of the guide sleeve 3300, FIG. 11C is a front view of the guide sleeve 3300, and FIG. 11D is a side view of the guide sleeve 3300. The guide sleeve 3300 may be configured to be slidably received within the foot portion 3200 of the drill guide 3000. The guide sleeve 3300 may further be configured to guide a plurality of drills into a plurality of locations on a bone without changing a position of the drill guide 3000 along the bone. The guide sleeve 3300 may be biased towards an extended state, distally away from the foot portion 3200 as a result of a compression spring 3400 that may be located between the guide sleeve 3300 and the foot portion 3200.

The guide sleeve 3300 may include a drill receiving end 3308, a bone contacting end 3307, and one or more grooves 3303. The drill receiving end 3308 may include two long drill apertures 3301, a short drill pin aperture 3305, a channel 3306. The bone contacting end 3307 may include a plurality of spikes 3302.

Each of the two long drill apertures 3301 may extend along a first longitudinal axis of the guide sleeve 3300 and may be sized to slidably receive a long drill 3614. The long drill 3614 may have a diameter between 2 mm and 2.5 mm. The long drill aperture 3301 may have a diameter slightly larger than the diameter of the long drill 3614.

The short drill pin aperture 3305 may extend along a second longitudinal axis of the guide sleeve 3300 and may be sized to slidably receive a short drill pin 3514. The short drill pin 3514 may have a diameter between 1.5 mm and 2 mm. The short drill pin aperture 3305 may have a diameter slightly larger than the diameter of the short drill pin 3514. The diameter of the short drill pin 3514 may be less than the diameter of the long drill 3614. The first longitudinal axis may be parallel to the second longitudinal axis.

The channel 3306 may extend along a longitudinal axis of the guide sleeve 3300 generally parallel to the long drill aperture 3301 and the short drill pin aperture 3305. The channel 3306 may not extend an entire length of the guide sleeve 3300. The channel 3306 may include a ledge 3304 at a distal most end of the channel 3306. The channel 3306 may be configured to receive the compression spring 3400.

The one or more grooves 3303 may extend along a longitudinal axis of the guide sleeve 3300 generally parallel to the long drill aperture 3301 and the short drill pin aperture 3305. The one or more grooves 3303 may not extend an entire length of the guide sleeve 3300. The one or more grooves 3303 may be configured to receive the posts 3203 of the foot portion 3200 so that the guide sleeve 3300 may be slidably captive within the foot portion 3200. The one or more grooves 3303 and the posts 3203 may limit the travel of the guide sleeve 3300 between the extended state and a contracted state.

The one or more grooves 3303 and the posts 3203 may be configured so that the guide sleeve 3300 is captive within the foot portion. More specifically, the one or more grooves 3303 and the posts 3203 may allow the guide sleeve 3300 to be slidably received within the guide sleeve aperture 3201, however, the guide sleeve 3300 may not be removeable from the guide sleeve aperture 3201 with the posts 3203 received in the one or more grooves 3303.

The plurality of spikes 3302 may be located at a distal end of the guide sleeve 3300. The plurality of spikes 3302 may be located at a bone contacting end of the guide sleeve 3300 and may be configured to engage a surface of the bone. The plurality of spikes 3302 may prevent the guide sleeve 3300 from sliding along the surface of the bone as the guide sleeve 3300 slides within the foot portion 3200. The plurality of spikes 3302 may prevent the guide sleeve 3300 from sliding along the surface of the bone when pressure is applied from the handle 3100 which may result in the guide sleeves 3300 sliding within the foot portion 3200 from the extended state towards the contracted state. The plurality of spikes 3302 may be particularly advantageous in preventing the guide sleeve 3300 from sliding along the surface of the bone when the guide sleeve 3300 engages the surface of the bone at a non-perpendicular angle.

The drill guide 3000 may be configured so that the spring-loaded guide sleeves 3300 remain parallel to each other while being incident on the surface of the bone, regardless of the contours of the surface of the bone.

FIG. 12 is a side view of a compression spring 3400 according to an embodiment of the present disclosure. The compression spring 3400 may include a first end 3402 and a second end 3404. The first end 3402 may be received within the channel 3306 and may abut the ledge 3304. The second end 3404 may abut the tab 3207 of the foot portion 3200. With the guide sleeve 3300 received within the foot portion 3200, the compression spring 3400 may bias the guide sleeve 3300 towards the extended state. The compression spring 3400 may be compressed as the guide sleeve 3300 slides within the foot portion 3200 from the extended state towards the contracted state. The compression spring may bias the guide sleeve 3300 towards the extended state. Alternatively, the compression spring 3400 may be configured as a resilient member configured to urge a bone contacting end 3307 of the guide sleeve 3300 against a bone portion.

FIG. 13 is a side view of a set of short drill pins 3500 according to an embodiment of the present disclosure. The set of short drill pins 3500 may include a 14 mm short drill pin 3514, a 17 mm short drill pin 3517, a 20 mm short drill pin 3526, a 23 mm short drill pin 3523, and a 26 mm short drill pin 3526. Each of the short drill pins included in the set of short drill pins 3500 may include identical or similar features. These features will be described for the 26 mm short drill pin 3526 and may apply to all short drill pins included in the set of short drill pins 3500.

The 26 mm short drill pin 3526 may be configured to be received within the short drill pin aperture 3305 of the drill guide 3040. The 26 mm short drill pin 3526 may be configured to create a hole into a bone. The 26 mm short drill pin 3526 may further be configured to remain in the bone after the drill guide 3040 is withdrawn from the bone and act as a guide pin for subsequent instruments used in a surgical procedure. The 26 mm short drill pin 3526 may guide the inserter to the pre-drilled holes in the bone configured to receive the legs 1002 of the compression staple 1000. The 26 mm short drill pin 3526 may be configured to be removeable from the bone after insertion of the compression staple 1000 into the bone.

The 26 mm short drill pin 3526 may include a fluted portion 3502, leg length indicators 3504, a proximal end 3506, a cutting diameter 3508, a bridge length indicator 3510, and a shaft portion 3512. The fluted portion 3502 may be located at a distal end of the 26 mm short drill pin 3526. The fluted portion 3502 may be configured to create a generally circular hole into the bone as a result of rotation of the 26 mm short drill pin 3526 and a force directed towards the bone. The proximal end 3506 may be located opposite the fluted portion 3502. The shaft portion 3512 may extend between the fluted portion 3502 and the proximal end 3506. The fluted portion 3502 and the shaft portion 3512 may have a generally the same cutting diameter 3508. The cutting diameter 3508 may be between 1.5 mm and 2 mm.

The bridge length indicator 3510 may be configured as a numerical indicator on the shaft portion 3512 of the 26 mm short drill pin 3526. The bridge length indicator 3510 may correspond to a bridge length 1020 of the compression staple 1000. A short drill pin corresponding to the bridge length 1020 of a chosen compression staple 1000 may be chosen from the set of short drill pins 3500.

The leg length indicators 3504 may be configured as circumferential markings on the shaft portion 3512. The leg length indicators 3504 may indicate to a user an optimal leg length 1025 of a compression staple 1000 based on the depth the 26 mm short drill pin 3526 may have been advanced into the bone. With the 26 mm short drill pin 3526 advanced into the bone a desired depth, the number of leg length indicators 3504 visible past the proximal end of the guide sleeve 3300 may indicate an appropriate leg length 1025 to be chosen.

For example, no visible leg length indicators 3504 may indicate that the longest leg length 1025 for the chosen bridge length 1020 may be chosen from the set of differently-sized compression staples 1000. As a second example, two visible leg length indicators 3504 may indicate that the shortest leg length 1025 for the chosen bridge length 1020 may be chosen from the set of differently-sized compression staples 1000. As yet a further example, three visible leg length indicators 3504 may indicate that the shortest leg length 1025, for the chosen bridge length 1020 from the set of differently-sized compression staples 1000, may protrude past the depth the 26 mm short drill pin 3526 has been advanced into the bone and the legs 1002 may protrude beyond a distal cortex of the bone when the compression staple 1000 is inserted into the bone.

FIG. 14 is a side view of a set of long drills 3600 according to an embodiment of the present disclosure. The set of long drills 3600 may include a 14 mm long drill 3614, a 17 mm long drill 3617, a 20 mm long drill 3620, a 23 mm long drill 3623, and a 26 mm long drill 3626. Each of the long drills included in the set of long drills 3600 may include identical or similar features. These features will be described for the 26 mm long drill 3626 and may apply to all long drills included in the set of long drills 3600.

The 26 mm long drill 3626 may be configured to be received within the long drill aperture 3301 of the drill guide 3040. The 26 mm long drill 3626 may be configured to create a hole into a bone.

The 26 mm long drill 3626 may include a fluted portion 3602, leg length indicators 3604, a proximal end 3606, a cutting diameter 3608, a bridge length indicator 3610, and a shaft portion 3612. The fluted portion 3602 may be located at a distal end of the 26 mm long drill 3626. The fluted portion 3602 may be configured to create a generally circular hole into the bone as a result of rotation of the 26 mm long drill 3626 and a force directed towards the bone. The proximal end 3606 may be located opposite the fluted portion 3602. The shaft portion 3612 may extend between the fluted portion 3602 and the proximal end 3606. The fluted portion 3602 and the shaft portion 3612 may have a generally the same cutting diameter 3608. The cutting diameter 3608 may be between 2 mm and 2.5 mm. The cutting diameter 3608 may be sized so that the drill hole created in the bone may be sized to receive the legs 1002 of the compression staple 1000.

The bridge length indicator 3610 may be configured as a numerical indicator on the shaft portion 3612 of the 26 mm long drill 3626. The bridge length indicator 3610 may correspond to a bridge length 1020 of the compression staple 1000. A long drill corresponding to the bridge length 1020 of a chosen compression staple 1000 may be chosen from the set of long drills 3600.

The leg length indicators 3604 may be configured as circumferential markings on the shaft portion 3612. The leg length indicators 3604 may indicate to a user an optimal leg length 1025 of a compression staple 1000 based on the depth the 26 mm long drill 3626 may have been advanced into the bone. With the 26 mm long drill 3626 advanced into the bone a desired depth, the number of leg length indicators 3604 visible past the proximal end of the guide sleeve 3300 may indicate an appropriate leg length 1025 to be chosen.

For example, no visible leg length indicators 3604 may indicate that the longest leg length 1025 for the chosen bridge length 1020 may be chosen from the set of differently-sized compression staples 1000. As a second example, two visible leg length indicators 3604 may indicate that the shortest leg length 1025 for the chosen bridge length 1020 may be chosen from the set of differently-sized compression staples 1000. As yet a further example, three visible leg length indicators 3604 may indicate that the shortest leg length 1025, for the chosen bridge length 1020 from the set of differently-sized compression staples 1000, may protrude past the depth the 26 mm long drill 3626 has been advanced into the bone and the legs 1002 may protrude beyond a distal cortex of the bone when the compression staple 1000 is inserted into the bone.

FIG. 15A is a perspective view of an impactor 4000 according to an embodiment of the present disclosure. FIG. 15B is a top view of the impactor 4000, FIG. 15C is a front view of the impactor, and FIG. 15D is a side view of the impactor 4000. The impactor 4000 may be configured to slide over the short drill pin 3526 and may act as a leveling indicator when determining how perpendicular the compression staple 1000 may be to the surface of the bone. This may facilitate bone preparation with a rongeur and/or other bone removal device and may ensure the compression staple 1000 sits flush with the surface of the bone. After initial insertion of the compression staple 1000 into the bone, the impactor 4000 may further be configured to impact the compression staple 1000 flush with the surface of the bone. The impactor 4000 may be configured to be guided to the insertion site by the short drill pins.

The impactor 4000 may include a body 4001, guide channels 4002, cut outs 4003, a locating boss 4004, and staple profile indicators 4005. The body 4001 may extend from a distal end 4006 to a proximal end 4007. The body 4001 may include ergonomic features such as grooves, recesses, surface textures, and/or apertures to provide better usability and/or weight reduction.

The distal end 4006 may include the guide channels 4002, the cut outs 4003, the locating boss 4004, and the staple profile indicators 4005. The guide channels 4002 may be configured to receive the short drill pins. The guide channels 4002 may extend proximally from the distal end 4006 along a longitudinal axis of the body 4001. The guide channels 4002 may extend proximally from the distal end 4006 a distance that may be greater than a length of a short drill pin, chosen from the set of short drill pins 3500, minus a shortest leg length 1025 of the compression staple 1000 chosen from the set of compression staples 1000 having a selected bridge length 1020. The guide channels 4002 may be spaced apart a distance that may be generally equal to a distance between a first short drill pin aperture 3305 and a second short drill pin aperture 3305.

The cut outs 4003 may facilitate visualization of the bone surface when the impactor 4000 is advanced along the short drill pins towards the surface of the bone. The locating boss 4004 may be configured to be received in the central aperture 1008 of the compression staple 1000. The locating boss 4004 may provide proper alignment of the impactor 4000 relative to the compression staple 1000 prior to impaction of the compression staple 1000 thereby ensuring generally equal impaction force between the four legs 1002 of the compression staple 1000.

In an embodiment, the body 4001 may include one or more side apertures positioned along an axis parallel to a longitudinal axis of the guide channels 4002. The side apertures may improve manufacturability. Additionally, or alternatively, the side apertures may facilitate visualization of the short drill pins 3500 within the guide channels 4002 through the side apertures.

In an embodiment, the body 4001 may include a size indicator to assist a user in selecting an impactor 4000 that corresponds to a specific size of staple 1000. The size indicator may include laser marking, engraving, embossing, debossing, pad printing, and/or other process known in the art to apply text to a medical instrument.

The staple profile indicators 4005 may be used to assess how flush a corresponding compression staple 1000 may seat against the surface of the bone. The staple profile indicators 4005 may have a profile that may generally correspond to a first bridge 1007 and a second bridge 1007 of a compression staple 1000 selected from a set of compression staples 1000. The impactor may be one of a set of differently-sized impactors, each corresponding to one of a set of differently-sized compression staples 1000, each having a different bridge length 1020.

FIG. 16A is a perspective view of the impactor 4000. The impactor 4000 of FIG. 16A may include guide channels 4002, a locating boss 4004, and staple profile indicators 4005 configured to correspond to a compression staple 1000 with a bridge length 1020 of approximately 14 mm.

FIG. 16B is a perspective view of an impactor 4100 according to an embodiment of the present disclosure. The impactor 4100 of FIG. 16B may include guide channels 4002, a locating boss 4004, and staple profile indicators 4005 configured to correspond to a compression staple 1000 with a bridge length 1020 of approximately 17 mm.

FIG. 16C is a perspective view of an impactor 4200 according to an embodiment of the present disclosure. The impactor 4200 of FIG. 16C may include guide channels 4002, a locating boss 4004, and staple profile indicators 4005 configured to correspond to a compression staple 1000 with a bridge length 1020 of approximately 20 mm.

FIG. 16D is a perspective view of an impactor 4300 according to an embodiment of the present disclosure. The impactor 4300 of FIG. 16D may include guide channels 4002, a locating boss 4004, and staple profile indicators 4005 configured to correspond to a compression staple 1000 with a bridge length 1020 of approximately 23 mm.

FIG. 16E is a perspective view of an impactor 4400 according to an embodiment of the present disclosure. The impactor 4400 of FIG. 16E may include guide channels 4002, a locating boss 4004, and staple profile indicators 4005 configured to correspond to a compression staple 1000 with a bridge length 1020 of approximately 26 mm.

Various parts of the impactor 4000 may be identical or similar to their counterparts on the impactor 4100, the impactor 4200, the impactor 4300, the impactor 4400, and/or other impactor embodiments presented herein; these parts may not be described again here. All statements made regarding the impactor 4000 may apply to all impactors described herein, unless they would be contradicted by the differences between the two.

FIG. 17A is a perspective view of an inserter 5000 according to an embodiment of the present disclosure. FIG. 17B is a top view of the inserter 5000, FIG. 17C is a front view of the inserter 5000, and FIG. 17D is a side view of the inserter 5000. The inserter 5000 may include a body 5100, a knob 5200, a drive shaft 5300, an actuation mechanism 5400, a stationary jaw 5500, a moveable jaw 5600, a compression spring 5700, and a dowel pin 5800.

The inserter 5000 may be configured to releasably engage the compression staple 1000. The inserter 5000 may be further configured to be guided by the short drill pins to improve ease of staple placement. The inserter 5000 may also be configured so that with the compression staple 1000 inserted into the bone, the inserter 5000 may be actuated to release the compression staple 1000.

The inserter 5000 may be configured so that a first compression staple 1000 may be reloaded into the jaws, or a second compression staple 1000 may be loaded in the jaws, of the inserter 5000 after the first compression staple 1000 is released from the jaws. The inserter 5000 may be configured so that, with the compression staple 1000 adjacent to the surface of the bone, the inserter 5000 may be impacted to drive the compression staple 1000 into the bone. The inserter 5000 may be configured to apply a force to the compression staple 1000 engaged in the jaws to transition the compression staple 1000 from the collapsed state to the distracted state.

The inserter 5000 may be ergonomically shaped which may facilitate single-handed insertion of the compression staple into the bone and actuation of the actuation mechanism 5400 to disengage the compression staple 1000 from the inserter 5000.

The inserter 5000 may be held between two fingers and/or one or more fingers and/or a palm of a hand to guide insertion of the compression staple 1000 into the bone. Additionally, or alternatively, the inserter 5000 may be held between a thumb, a first finger, and/or a palm of a hand to guide insertion of the compression staple 1000 into the bone.

The inserter 5000 may be held between two fingers and/or one or more fingers and/or a palm of a hand and the actuation mechanism may be actuated by a thumb of the same hand. Additionally, or alternatively, the inserter 5000 may be held between a thumb, a first finger, and/or a palm of a hand and the actuation mechanism may be actuated by a second finger of the same hand.

The inserter 5000 may include a closed configuration in which the stationary jaw is spaced apart from the moveable jaw a first distance and an open configuration in which the stationary jaw is spaced apart from the moveable jaw a second distance greater than the first distance. The compression staple 1000 may be captive within the inserter 5000 when the inserter 5000 is in the closed configuration. With the inserter 5000 in the open configuration, the compression staple 1000 may be released from the inserter 5000. The inserter 5000 may also be configured to facilitate single-handed actuation of the actuation mechanism 5400 to transition between the closed configuration and the open configuration.

The stationary jaw 5500 and the moveable jaw 5600 may be configured to securely engage the compression staple 1000. The inserter 5000 may be one of a set of differently-sized inserters, each corresponding to one of a set of differently-sized compression staples 1000, each inserter having a differently sized stationary jaw 5500 and/or a differently sized moveable jaw 5600.

FIG. 18A is a perspective view of the inserter 5000. The inserter 5000 of FIG. 18A may include a stationary jaw 5500 and/or a moveable jaw 5600 sized to correspond to a compression staple 1000 with a bridge length 1020 of approximately 14 mm.

FIG. 18B is a perspective view of an inserter 5010 according to an embodiment of the present disclosure. The inserter 5010 of FIG. 18B may include a stationary jaw 5500 and/or a moveable jaw 5600 sized to correspond to a compression staple 1000 with a bridge length 1020 of approximately 17 mm.

FIG. 18C is a perspective view of an inserter 5020 according to an embodiment of the present disclosure. The inserter 5020 of FIG. 18C may include a stationary jaw 5500 and/or a moveable jaw 5600 sized to correspond to a compression staple 1000 with a bridge length 1020 of approximately 20 mm.

FIG. 18D is a perspective view of an inserter 5030 according to an embodiment of the present disclosure. The inserter 5030 of FIG. 18D may include a stationary jaw 5500 and/or a moveable jaw 5600 sized to correspond to a compression staple 1000 with a bridge length 1020 of approximately 23 mm.

FIG. 18E is a perspective view of an inserter 5040 according to an embodiment of the present disclosure. The inserter 5040 of FIG. 18E may include a stationary jaw 5500 and/or a moveable jaw 5600 sized to correspond to a compression staple 1000 with a bridge length 1020 of approximately 26 mm.

Various parts of the inserter 5000 may be identical or similar to their counterparts on the inserter 5010, the inserter 5020, the inserter 5030, the inserter 5040, and/or other inserter embodiments presented herein; these parts may not be described again here. All statements made regarding the inserter 5000 may apply to all inserters described herein, unless they would be contradicted by the differences between the two.

FIG. 19A is a perspective view of a body 5100 according to an embodiment of the present disclosure. FIG. 19B is a top view of the body 5100, FIG. 19C is a front view of the body 5100, and FIG. 19D is a side view of the body 5100. The body 5100 may include an aperture 5101, a proximal end 5102, and a distal end 5103.

The aperture 5101 may include a knob boss 5110. The aperture 5101 may be configured to receive the knob 5200. The aperture 5101 may further be configured so that the knob 5200 may rotate within the aperture 5101 about a longitudinal axis of the knob 5200. The knob boss 5110 may be configured to be received within a locating recess 5203 of the knob 5200. The knob boss 5110 and the locating recess 5203 may facilitate generally consistent alignment of the knob 5200 relative to the body 5100. The knob boss 5110 and the locating recess 5203 may further allow rotation of the knob 5200 relative to the body 5100.

The proximal end 5102 may be configured so that a mallet, or similar instrument, may be used to impact the proximal end 5102 to insert a compression staple 1000, that may be engaged in the jaws of the inserter 5000, into the bone. The distal end 5103 may include a jaw recess 5104 configured to captively receive the stationary jaw 5500. The jaw recess 5104 may be sized to provide a press fit with the stationary jaw 5500. Alternatively, the jaw recess 5104 may include a tab, an undercut, or another feature configured to prevent the stationary jaw 5500 from disengaging from the body 5100.

The body 5100 may further include a drive shaft aperture 5105 extending from the distal end 5103 to the aperture 5101. The drive shaft aperture 5105 may be configured to receive the drive shaft 5300. The drive shaft aperture 5105 may have a non-circular profile generally corresponding to the profile of the drive shaft 5300. The drive shaft aperture 5105 may be configured to inhibit rotation of the drive shaft 5300 relative to the body 5100 as the knob 5200 is rotated and the drive shaft 5300 travels along a longitudinal axis of the drive shaft 5300.

The body 5100 may include a guide channel 5106 extending proximally from the distal end 5103. The guide channel 5106 may be configured to receive the short drill pins. The guide channel 5106 may extend proximally from the distal end 5103 a distance that may be greater than a length of a short drill pin, chosen from the set of short drill pins 3500, minus a shortest leg length 1025 of the compression staple 1000 chosen from the set of compression staples 1000 having a selected bridge length 1020. The guide channel 5106 may extend medially and laterally from a plane of bilateral symmetry of the body 5100 a total distance that may be generally equal to a distance between a first short drill pin aperture 3305 and a second short drill pin aperture 3305. Additionally, the guide channel 5106 may extend anteriorly and posteriorly a total distance that may be greater than half of the bridge width 1022 to allow the inserter 5000 to be removed. The drive shaft aperture 5105 may be smaller than the bridge width 1022 of the smallest staple 1000.

The body 5100 may also include a button recess 5107 configured to receive a paddle 5401 of the actuation mechanism 5400. The button recess 5107 may include a spring locating boss 5108, a pivot aperture 5109, and a button arm slot 5111. The button arm slot 5111 may be configured to receive an arm portion 5403 of the actuation mechanism 5400.

The pivot aperture 5109 may extend medially and laterally from a plane of bilateral symmetry of the body 5100 a total distance that may be greater than a width of the button arm slot 5111. The pivot aperture 5109 may be configured to receive one or more pivot bosses 5409 of the actuation mechanism 5400 so that the actuation mechanism 5400 may be rotatably captive in the body 5100.

The spring locating boss 5108 may be configured to be received in a first end 5701 of a compression spring 5700. The spring locating boss 5108 may retain a location of the compression spring 5700 relative to the button recess 5107.

FIG. 20A is a perspective view of a knob 5200 according to an embodiment of the present disclosure. FIG. 20B is a top view of the knob 5200, FIG. 20C is a front view of the knob 5200, and FIG. 20D is a side view of the knob 5200. The knob 5200 may include a threaded aperture 5201, one or more grips 5202, and a locating recess 5203.

The threaded aperture 5201 may be configured to thread-ably receive the drive shaft 5300. The threaded aperture 5201 may be configured as an acme thread profile. Alternatively, the threaded aperture 5201 may be configured as a buttress thread profile, a square thread profile, or a v-thread profile.

Rotation of the knob 5200 may be converted into linear movement of the drive shaft 5300. The locating recess 5203 may be configured to receive the knob boss 5110 and may facilitate generally consistent alignment of the knob 5200 relative to the body 5100.

The grip 5202 may be used to rotate the knob 5200. The grip 5202 may include features to improve the grip of a user during rotation of the knob 5200. The grip 5202 may include a radial pattern of axial grooves and/or protrusions. Alternatively, the grip 5202 may include a knurled pattern on an outside diameter. Alternatively, the grip 5202 may include a roughened surface treatment. Alternatively, the grip 5202 may include a radial pattern of flat surfaces. Alternatively, the knob 5200 may have a non-circular cross-sectional profile.

FIG. 21A is a perspective view of a drive shaft 5300 according to an embodiment of the present disclosure. FIG. 21B is a top view of the drive shaft 5300, FIG. 21C is a front view of the drive shaft 5300, and FIG. 21D is a side view of the drive shaft 5300. The drive shaft 5300 may include a shaft 5301, a proximal end 5303, and a distal end 5304. The drive shaft 5300 may have a non-circular profile configured to be receive in the drive shaft aperture 5105. The drive shaft aperture 5105 may be configured to inhibit rotation of the drive shaft 5300 relative to the body 5100 as the knob 5200 is rotated and the drive shaft 5300 travels along a longitudinal axis of the drive shaft 5300.

The proximal end 5303 may include a threaded portion 5302 configured to threadably engage the knob 5200 so that rotation of the knob 5200 may be converted into linear movement of the drive shaft 5300. The threaded portion 5302 may be configured as an acme thread profile. Alternatively, the threaded portion 5302 may be configured as a buttress thread profile, a square thread profile, or a v-thread profile.

The distal end 5304 may be configured to abut the bridge 1007 of the compression staple 1000. With the compression staple 1000 retained in the stationary jaw 5500 and the moveable jaw 5600, as the knob 5200 is rotated causing the drive shaft 5300 to travel distally, the distal end 5304 may press against the bridge 1007 of the compression staple 1000 which may result in the legs 1002 spreading apart causing the compression staple 1000 to move from a collapsed state towards a distracted state.

Conversely, rotation of the knob 5200 in an opposite direction may cause the drive shaft 5300 to travel proximally, which may result in the legs 1002 moving inwards causing the compression staple 1000 to move from a distracted state towards a collapsed state.

The distal end 5304 may include a rounded profile so that a point of contact between the distal end 5304 and the bridge 1007 may remain generally constant during expansion and/or compression of the compression staple 1000. Additionally, or alternatively, the distal end 5304 may include a cap or other material that may reduce the risk of denting and/or notching of the bridge 1007 during expansion of the compression staple 1000.

FIG. 22A is perspective view of an actuation mechanism 5400 according to an embodiment of the present disclosure. FIG. 22B is a top view of the actuation mechanism 5400, FIG. 22C is a front view of the actuation mechanism 5400, and FIG. 22D is a side view of the actuation mechanism 5400. The actuation mechanism 5400 may be configured to be rotatably received in the body 5100. The actuation mechanism 5400 may be configured to rotate relative to the body 5100 which may result in linear translation of the moveable jaw 5600.

The actuation mechanism 5400 may include a paddle 5401 and an arm portion 5403. The paddle 5401 may be configured to be received in the button recess 5107. The paddle 5401 may include a spring recess 5407. The spring recess 5407 may be configured to receive a second end 5702 of the compression spring 5700. The spring recess 5407 may retain a location of the compression spring 5700 relative to the actuation mechanism 5400. The compression spring 5700 may bias the actuation mechanism 5400 away from a center plane of the body 5100 so that the paddle 5401 may generally align with an outer surface of the body 5100.

The arm portion 5403 may include a slot 5402, a jaw aperture 5408, and one or more pivot bosses 5409. The one or more pivot boss 5409 may be configured to be received in the pivot aperture 5109 thereby allowing the actuation mechanism 5400 to rotate relative to the body 5100. The slot 5402 may extend medially and laterally from a plane of bilateral symmetry of the actuation mechanism 5400 a total distance that may be less than a width of the arm portion 5403.

The slot 5402 may be configured so that the one or more pivot bosses 5409 may be collapsed inwardly so that the one or more pivot bosses 5409 may be received within the button arm slot 5111. With the one or more pivot bosses 5409 aligned with the pivot apertures 5109, the one or more pivot bosses 5409 may expand into the pivot apertures 5109 thereby captively and rotatable coupling the actuation mechanism 5400 with the body 5100. The one or more pivot bosses 5409 may each include a lead-in chamfer that may help guide the one or more pivot bosses 5409 into the button arm slot 5111.

The jaw aperture 5408 may be configured to receive a dowel pin 5800. The jaw aperture 5408 may be shaped as a rectangle with a full radius on each end. The jaw aperture 5408 may allow rotation and translation of the dowel pin 5800. Alternatively, the jaw aperture 5408 may be shaped as an oval, an ellipse, a rectangle with or without radiused corners, or other geometric shape that may allow rotation and translation of the dowel pin 5800.

FIG. 23A is a perspective view of a stationary jaw 5500 according to an embodiment of the present disclosure. FIG. 23B is a top view of the stationary jaw 5500, FIG. 23C is a front view of the stationary jaw 5500, and FIG. 23D is a side view of the stationary jaw 5500. The stationary jaw 5500 may be configured to be securely coupled to the distal end 5103 of the body 5100. The stationary jaw 5500 may include a first retention mechanism 5510, alignment apertures 5502, locating channels 5503, a drive shaft groove 5504, and a guide channel 5505.

In an embodiment, the first retention mechanism 5510 may include two hooks 5501. Each hook 5501 may include a bridge engaging surface 5506 configured to engage an inside surface of a first bridge 1007 of the compression staple 1000.

The hooks 5501 may be spaced apart from each other a distance so that the hooks 5501 may be received between a pair of legs 1002. The hooks 5501 and the distal end 5304 of the drive shaft may form a three-point bend configuration acting on the first bridge 1007. Each bridge engaging surface 5506 may be shaped to have a single point of contact with the inside surface of the first bridge 1007 as the arched portion 1016 may be flexed and the compression staple 1000 may be transitioned between the distracted state and the collapsed state.

The locating channels 5503 may be configured to be captively received in the jaw recess 5104 of the body 5100. The locating channels 5503 may be sized to provide a press fit with the jaw recess 5104. Alternatively, the locating channels 5503 may include a tab, an undercut, or another feature configured to prevent the stationary jaw 5500 from disengaging from the body 5100.

The alignment apertures 5502 may be configured to slidably receive alignment posts 5602 of the moveable jaw 5600. The alignment apertures 5502 may facilitate linear translation of the moveable jaw 5600 relative to the stationary jaw 5500. In an embodiment, the stationary jaw 5500 may have two alignment apertures 5502. The two alignment apertures 5502 may be equally spaced medially and laterally from a plane of bilateral symmetry of the stationary jaw 5500. Additionally, the alignment apertures 5502 and the alignment posts 5602 may transfer the force required to transition the staple 1000 between the distracted state and the collapsed state from the movable jaw 5600 to the stationary 5500 jaw and into the inserter 5000. The drive shaft groove 5504 may be configured to receive the drive shaft 5300. The drive shaft groove 5504 may have a non-circular profile generally corresponding to at least a portion of a profile of the drive shaft 5300. The drive shaft groove 5504 may be configured to inhibit rotation of the drive shaft 5300 relative to the stationary jaw 5500 as the knob 5200 is rotated and the drive shaft 5300 travels along a longitudinal axis of the drive shaft 5300. The drive shaft groove 5504 may allow the drive shaft 5300 to abut the compression staple 1000 when the stationary jaw 5500 is captively received in the body 5100 and the compression staple 1000 is engaged with the hooks 5501.

The guide channel 5505 may be configured to receive the short drill pins. The guide channel 5505 may extend medially and laterally from a plane of bilateral symmetry of the stationary jaw 5500 a total distance that may be generally equal to a distance between a first short drill pin aperture 3305 and a second short drill pin aperture 3305. The guide channel 5505 may allow the short drill pins to pass through the stationary jaw 5500 and into the guide channel 5106 of the body 5100.

FIG. 24A is a perspective view of a movable jaw 5600 according to an embodiment of the present disclosure. FIG. 24B is a top view of the movable jaw 5600, FIG. 24C is a front view of the movable jaw 5600, and FIG. 24D is a side view of the movable jaw 5600. The moveable jaw 5600 may be configured to be slidably received in the stationary jaw 5500. The moveable jaw 5600 may include a second retention mechanism 5610, alignment posts 5602, a drive shaft groove 5604, a guide channel 5605, a button aperture 5608, and a button channel 5609.

In an embodiment, the second retention mechanism 5610 may include two hooks 5601. Each hook 5601 may include a bridge engaging surface 5606 configured to engage an inside surface of a second bridge 1007 of the compression staple 1000.

The hooks 5601 may be spaced apart from each other a distance so that the hooks 5601 may be received between a pair of legs 1002. The hooks 5601 and the distal end 5304 of the drive shaft may form a three-point bend configuration acting on the second bridge 1007. Each bridge engaging surface 5606 may be shaped to have a single point of contact with the inside surface of the second bridge 1007 as the arched portion 1016 may be flexed and the compression staple 1000 may be transitioned between the distracted state and the collapsed state.

The alignment posts 5602 may be configured to be slidably received in the alignment apertures 5502. The alignment posts 5602 may facilitate linear translation of the moveable jaw 5600 relative to the stationary jaw 5500. In an embodiment, the moveable jaw 5600 may have two alignment posts 5602. The two alignment posts 5602 may be equally spaced medially and laterally from a plane of bilateral symmetry of the moveable jaw 5600.

In an alternate embodiment, the stationary jaw 5500 may include alignment posts 5602 and the moveable jaw 5600 may include alignment apertures 5502.

The drive shaft groove 5604 may be configured to receive the drive shaft 5300. The drive shaft groove 5604 may have a non-circular profile generally corresponding to at least a portion of a profile of the drive shaft 5300. The drive shaft groove 5604 may be configured to inhibit rotation of the drive shaft 5300 relative to the moveable jaw 5600 as the knob 5200 is rotated and the drive shaft 5300 travels along a longitudinal axis of the drive shaft 5300. The drive shaft groove 5604 may allow the drive shaft 5300 to abut the compression staple 1000 when the moveable jaw 5600 is slidably received in the stationary jaw 5500 and the compression staple 1000 is engaged with the hooks 5601.

The guide channel 5605 may be configured to receive the short drill pins. The guide channel 5605 may extend medially and laterally from a plane of bilateral symmetry of the moveable jaw 5600 a total distance that may be generally equal to a distance between a first short drill pin aperture 3305 and a second short drill pin aperture 3305. The guide channel 5605 may allow the short drill pins to pass through the moveable jaw 5600 and into the guide channel 5106 of the body 5100.

The button channel 5609 may be configured to receive the arm portion 5403 of the actuation mechanism 5400. With the arm portion 5403 received within the button channel 5609 the button aperture 5608 may align with the jaw aperture 5408. A dowel pin 5800 may be received in the button aperture 5608 and the jaw aperture 5408 thereby rotatably coupling the actuation mechanism 5400 and the moveable jaw 5600.

The hooks 5501 may be spaced apart a distance generally equal to a distance the hooks 5601 may be spaced apart. The hooks 5501 may extend from the stationary jaw 5500 a distance that may be less than half the bridge width 1022. The hooks 5601 may extend from the moveable jaw 5600 a distance that may be less than half the bridge width 1022.

The inserter 5000 may be configured so that, with the actuation mechanism 5400 fully depressed, the alignment posts 5602 of the moveable jaw 5600 may remain within the alignment apertures 5502 of the stationary jaw 5500. The inserter 5000 may be configured so that when the actuation mechanism 5400 is actuated, or depressed, the jaws may open. The actuation of the jaws may be parallel and the jaws may remain parallel while opening in response to actuation of the button, and while closing in response to release of the button. The inserter 5000 may further be configured to enable single hand actuation of the button to disengage the compression staple from the inserter.

FIG. 25 is a perspective view of a compression spring 5700 according to an embodiment of the present disclosure. FIG. 26 is a perspective view of a dowel pin 5800 according to an embodiment of the present disclosure. The spring may include a first end 5701 and a second end 5702. The first end 5701 may be configured to be received on the spring locating boss 5108 of the body 5100. The second end 5702 may be configured to be received in the spring recess 5407 of the actuation mechanism 5400. The compression spring 5700 may bias the actuation mechanism 5400 away from a center plane of the body 5100 thereby actuating the moveable jaw 5600 to closed position in which moveable jaw 5600 may be spaced apart from the stationary jaw 5500 a distance that may be less than a bridge width 1022 of the compression staple 1000. With a compression staple 1000 engaged in the jaws, the moveable jaw 5600 may exert a force (via the compression spring and the button) on the compression staple 1000 to firmly retain the compression staple within the jaws.

With the paddle 5401 depress towards the center plane of the body 5100, the moveable jaw 5600 may translate away from the stationary jaw 5500 to an open position. In the open position the distance between the hooks 5501 of the stationary jaw 5500 and the hooks 5601 of the moveable jaw 5600 may be greater than the bridge width 1022, thereby allowing the inserter 5000 to disengage the compression staple 1000.

The inserter 5000 may be configured so that the stationary jaw 5500 and the moveable jaw 5600 may remain parallel while the moveable jaw 5600 moves between the closed position and the open position. Additionally, or alternatively, the inserter 5000 may be configured so that the bridge engaging surface 5506 and the bridge engaging surface 5606 may remain aligned while the moveable jaw 5600 moves between the closed position and the open position.

The actuation mechanism 5400 may pivot about the pivot bosses 5409 such that the arm portion may move in a direction opposite that of the paddle 5401, thereby causing the moveable jaw 5600 to move towards the open position when the paddle 5401 is depressed.

With a compression staple 1000 engaged with the jaws, clockwise rotation of the knob 5200 may result in the drive shaft 5300 advancing distally, thereby applying a force to the arched portion 1006 causing the compression staple 1000 to transition towards a distracted state. Conversely, counterclockwise rotation of the knob 5200 may result in the drive shaft retracting proximally, thereby decreasing the force to the arched portion 1006 allowing the compression staple 1000 to transition towards a collapsed state.

The actuation mechanism 5400 may be pressed to facilitate loading of the compression staple 1000 into the inserter 5000. The actuation mechanism 5400 may be released to retain the compression staple 1000 within the jaws. With the compression staple inserted into the bone, the actuation mechanism 5400 may be depressed to release the staple from the jaws of the inserter 5000.

All the instruments described herein may be manufactured using machining, injection molding, additive manufacturing, stamping, forging, casting, and/or any combination of the above. All of the instruments, and their components, described herein may be manufactured from stainless steel (for example: 316, 316L, 17-4ph, 303, 304, 420, 440c or other stainless steel), and/or polymers (for example: polyamide, Radel, Ultem, Delrin, ABS, polycarbonate or other polymers).

FIG. 27A is a perspective view of a foot and a compression staple 1000 according to an embodiment of the present disclosure. FIG. 27B is a top view of the foot and the compression staple 1000. The compression staple 1000 may be configured to span a first bone portion 500 and a second bone portion 550. The first bone portion 500 and the second bone portion 550 may be separated by a fracture. Additionally, or alternatively, the first bone portion 500 and the second bone portion 550 may be separated by a joint. The compression staple 1000 may apply compression between the first bone portion 500 and the second bone portion 550. The compression staple 1000 may be configured to support fusion of the first bone portion 500 and the second bone portion 550.

An exemplary method of bone fixation using a compression staple may include the following steps:

FIG. 28 is a perspective view of a foot and a sizer 2000 according to an embodiment of the present disclosure. The first sizing tip 2150 may engage the first bone portion 500 and the second sizing tip 2250 may engage the second bone portion 550 to determine the desired compression staple 1000 bridge length 1020.

FIG. 29 is a partial top view of a drill guide 3000 according to an embodiment of the present disclosure. The drill guide 3000 may include a first guide hole 3211, a second guide hole 3212, a third guide hole 3213, a fourth guide hole 3214, a fifth guide hole 3215, and a sixth guide hole 3216.

Compression Staple Bridge Sizing

1. Determine the appropriate compression staple bridge length as desired using the sizer.
2. Select a surgical kit corresponding to the determined compression staple size.
3. The surgical kit may include:
    a. One or more compression staples of the determined size
    b. A sizer
    c. A drill guide (configured to correspond to the determined compression staple size)
    d. Two or more short drill pins (configured to correspond to the determined compression staple size)
    e. One or more long drills (configured to correspond to the determined compression staple size)
    f. An impactor (configured to correspond to the determined compression staple size)
    g. An Inserter (configured to correspond to the determined compression staple size)
4. The compression staple may be pre-loaded into the inserter. The compression staple may be in a state between a collapsed state and a distracted state in the inserter.
5. The contents of the surgical kit may be divided between multiple surgical sub-kits.
6. Each surgical kit (or surgical sub-kit if applicable) may be provided to a user sterile packaged.
7. The sizer may be provided in a separate kit so that it may be used to determine the desired compression staple size prior to opening a surgical kit containing a compression staple.

FIG. 30A is a perspective view of a foot, a drill guide 3020, and a short drill pin 3520 according to an embodiment of the present disclosure. FIG. 30B is a perspective view of the foot, the drill guide 3020, and two short drill pins 3520 according to an embodiment of the present disclosure. FIG. 31 is a table of compression staple 1000 leg lengths 1025 and compression staple 1000 bridge lengths 1020 according to an embodiment of the present disclosure. FIG. 32 is a series of perspective views of a drill guide 3020, short drill pins 3520, and a long drill 3620 according to an embodiment of the present disclosure.

Compression Staple Leg Length Sizing

8. Place the drill guide through an incision centered over the fracture and/or joint between the first bone portion and the second bone portion.

9. Tilt the drill guide to match the preferred compression staple leg trajectory relative to the bone surface.

10. Place a first short drill pin onto a driver.

11. Place a first short drill pin through a first guide hole of the drill guide into the first bone portion. Drill the short drill pin into the bone to the maximum desired depth.

a. Note: in hard bone, pulling the short drill pin back 3-4mm after initially reaching the correct depth, and then readvancing the short drill pin to the full depth may help evacuate bone, making short drill pin removal easier.

b. Note: do no begin drilling until the short drill pin has contacted the bone surface through the drill guide.

12. Remove the first short drill pin from the driver and leave the first short drill pin in the first bone portion.

13. Place a second short drill pin onto the driver.

14. Place a second short drill pin through a second guide hole of the drill guide and drill into the second bone portion to the same depth as the first short drill pin was drilled into the first bone portion.

15. Remove the second short drill pin from the driver and leave the second short drill pin in the second bone portion.

16. Note the short drill pin with the highest count of visible leg length indicators above the top surface of the drill guide. Refer to the table of FIG. 31 to select a compression staple leg length.

17. Leg lengths denoted with a "–" indicate the smallest leg length may protrude past the current drill depth and the legs may protrude beyond a distal cortex of the bone when inserted. A user may consider using a compression staple with a smaller bridge length and may repeat steps 8-16 above.

18. Place a long drill onto the driver and use the drill to create first two holes in a first bone portion:

a. place the long drill into the third guide hole of the drill guide and drill into the first bone portion to the marked depth defined by the table of FIG. 31.

b. place the long drill into the fourth guide hole of the drill guide and drill into the first bone portion to the marked depth defined by the table of FIG. 31.

19. Use the drill to create second two holes in a second bone portion:

a. place the long drill into the fifth guide hole of the drill guide and drill into the second bone portion to the marked depth defined by the table of FIG. 31.

b. place the long drill into the sixth guide hole of the drill guide and drill into the second bone portion to the marked depth defined by the table of FIG. 31.

20. Remove the drill guide, leaving the short drill pins inserted in the first bone portion and second bone portion.

FIG. 33A is a perspective view of a foot, two short drill pins 3520, and an impactor 4200 according to an embodiment of the present disclosure. FIG. 33B is a perspective view of the foot, the two short drill pins 3520, the impactor 4200, and a compression staple 1000 according to an embodiment of the present disclosure. FIG. 34A is a perspective view of a foot and two short drill pins 3520 according to an embodiment of the present disclosure. FIG. 34B is a perspective view of the foot, the two short drill pins 3520, and an impactor 4200 according to an embodiment of the present disclosure.

Bone Preparation

21. Guide the impactor over the short drill pins in the bone until the impactor rests on the bone surface.

22. The distal end of the retractor may be representative of the final orientation and setting of the compression staple. If the bone surface is uneven, the compression staple may not sit flush with the bone surface. If the impactor does not sit adequately flush with the bone surface, remove the impactor and remove any bony prominences with rongeurs or similar instrument until the impactor sits flush to the bone surface at all for corners of the distal end of the impactor.

a. Note: short drill pins must remain inserted in the bone during bone preparation.

23. Use the impactor to validate the prepped bone surface. Repeat step 24 until the bone surface is adequately prepped.

FIG. 35A is a partial front view of an inserter 5020 and a compression staple 1000 according to an embodiment of the present disclosure.

Staple Distraction

24. Load the compression staple into the inserter (if necessary).

25. Rotate the knob clockwise to distract the compression staple legs to parallel. Do no distract past parallel.

a. Note: parallel may be determined by holding the compression staple against the fourth guide hole and the sixth guide hole of the drill guide (alternatively the third guide hole and the fifth guide hole may be used) and rotating the knob clockwise until the tips of the legs align with the fourth guide hole and the sixth guide hole. The knob may be rotated clockwise to distract and counter-clockwise to collapse the compression staple legs.

FIG. 35B is a perspective view of the inserter 5020, the compression staple 1000, two short drill pins 3520, and a foot according to an embodiment of the present disclosure. FIG. 36A is a perspective view of an inserter 5020, two short drill pins 3520, a compression staple 1000, and a foot according to an embodiment of the present disclosure. FIG. 36B is a perspective view of the inserter 5020, the two short drill pins 3520, the compression staple 1000 and the foot. FIG. 36C is a perspective view of the inserter 5020, the two short drill pins 3520, the compression staple 1000 and the foot. FIG. 36D is a perspective view of the inserter 5020, the two short drill pins 3520, the compression staple 1000 and the foot. FIG. 36E is a perspective view of the inserter 5020, the two short drill pins 3520, the compression staple 1000 and the foot. FIG. 36F is a perspective view of the inserter 5020, the two short drill pins 3520, the compression staple 1000 and the foot. FIG. 37 is a perspective view of an inserter 5020, a compression staple 1000, and a foot according to an embodiment of the present disclosure.

Staple Insertion

26. Slide the inserter with the compression staple in the distracted state over the short drill pins.

a. Note: pinching the short drill pins together so the tops of the short drill pins contact the pin notch may aid in insertion of the short drill pins into the inserter. Push the inserter distally over the short drill pins until the short drill pins are captive inside the inserter and verify that the compression staple tips align with the previously drilled holes in the bone portions.

27. Push the inserter by hand along the short drill pins until the compression staple legs are inserted into their corresponding predrilled holes.

28. Using a mallet, lightly impact the proximal end of the inserter until the inserter is close to, or lightly touching, the bone surface.

29. Release the compression staple from the inserter by turning the knob counter-clockwise and then depressing the button on the inserter.

30. Slide the inserter hooks out from under the compression staple bridge and remove the inserter.

FIG. 38A is a perspective view of an impactor 4200, a compression staple 1000, two short drill pins 3520, and a foot according to an embodiment of the present disclosure.

Impact Staple Flush

31. Place the impactor over the short drill pins. Using a mallet, set the compression staple flush with the bone surface.

32. Remove the impactor.

FIG. 38B is a perspective view of the foot and the compression staple 1000. FIG. 38C is a perspective view of the foot and the compression staple 1000.

Final Evaluation

33. Ensure the compression staple has provided adequate stability and compression.

34. Remove the short drill pins.

35. Repeat steps 1 through 36 to implant additional compression staples as desired. If a second compression staple is placed with the bridge near the first compression staple, ensure adequate spacing between the first staple bridge and the second staple bridge to avoid interference with the inserter hooks during insertion.

Those of skill in the art will recognize that this is only one of many potential methods that may be used for bone fixation using a compression staple. In alternative embodiments, the methods described herein may be used for bone fixation using compression staples other than those described herein. Additionally, or alternatively, the compression staples and instruments described herein may be used for bone fixation using methods other than those described herein.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment.

Recitation of the term "first" with respect to a feature or element does not necessarily imply the existence of a second or additional such feature or element. Elements recited in means-plus-function format are intended to be construed in accordance with 35 U.S.C. § 112(f). It will be apparent to those having skill in the art that changes may be made to the details of the above-described embodiments without departing from the underlying principles set forth herein.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, as well as components that are removably and/or non-removably coupled with each other. The term "abutting" refers to items that may be in direct physical contact with each other, although the items may not necessarily be attached together. The phrase "fluid communication" refers to two or more features that are connected such that a fluid within one feature is able to pass into another feature. Moreover, as defined herein the term "substantially" means within +/−20% of a target value, measurement, or desired characteristic.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the devices, systems, instruments, and methods disclosed herein.

What is claimed is:

1. A method of bone fixation using a compression staple system, the method comprising:

loading a compression staple comprising two legs into an inserter; wherein loading the compression staple comprises:

moving a moveable jaw of the inserter, relative to a stationary jaw of the inserter to an open position in which the moveable jaw is spaced apart from the stationary jaw a first distance;

engaging a first retention mechanism of the stationary jaw with the compression staple;

engaging a second retention mechanism of the moveable jaw with the compression staple; and moving the moveable jaw, relative to the stationary jaw, to a closed position in which the moveable jaw is spaced apart from the stationary jaw a second distance that is less than the first distance;

positioning a drill guide proximate a first bone portion and a second bone portion;

using the drill guide and a drill to create a first hole in the first bone portion and a second hole in the second bone portion, wherein the first hole and the second hole are configured to receive the two legs of the compression staple;

using the drill guide and a first drill pin, driving the first drill pin into the first bone portion;

using the drill guide and a second drill pin, driving the second drill pin into the second bone portion;

withdrawing the drill guide, leaving the first drill pin in the first bone portion and the second drill pin in the second bone portion;

guiding the inserter and the compression staple over the first drill pin and the second drill pin;

inserting the two legs of the compression staple into the first hole and the second hole;

actuating the inserter to release the compression staple; wherein actuating the inserter to release the compression staple comprises:

moving the moveable jaw, relative to the stationary jaw, to the open position in which the first retention mechanism disengages the compression staple; and disengaging the second retention mechanism from the compression staple;

wherein the stationary jaw and the moveable jaw remain parallel between the closed position and the open position;

withdrawing the inserter; and removing the first drill pin and the second drill pin.

2. The method of claim 1, further comprising:

guiding an impactor over the first drill pin and the second drill pin; and using the impactor to assess a first surface of the first bone portion and a second surface of the second bone portion to determine if the compression staple is insertable to be flush with the first surface and the second surface.

3. The method of claim 1, further comprising guiding an impactor over the first drill pin and the second drill pin to impact the compression staple flush with a first surface of the first bone portion and a second surface of the second bone portion.

4. The method of claim 1, wherein the drill guide comprises:

a handle;

a foot portion coupled to the handle;

a first guide sleeve slidably received in the foot portion, the first guide sleeve comprising a first aperture configured to guide the drill towards the first bone portion; and a second guide sleeve slidably received in the foot portion, the second guide sleeve comprising a second aperture configured to guide the drill towards the second bone portion; and the method further comprises:

with a first resilient member, urging a first bone contacting end of the first guide sleeve against the first bone portion; and with a second resilient member, urging a second bone contacting end of the second guide sleeve against the second bone portion, independently of urging the first bone contacting end of the first guide sleeve against the first bone portion.

5. The method of claim 1, wherein the first bone portion and the second bone portion are separated at a joint or a fracture.

6. The method of claim 5, wherein creating the first hole in the first bone portion comprises creating the first hole generally parallel to the joint or the fracture, and creating the second hole in the second bone portion comprises creating the second hole generally parallel to the joint or the fracture.

7. A method of bone fixation using a compression staple system, the method comprising:

loading a compression staple into an inserter;

positioning a drill guide proximate a first bone portion and a second bone portion;

wherein the drill guide comprises:

a handle;

a foot portion coupled to the handle;

a first guide sleeve slidably received in the foot portion and comprising a first aperture configured to guide a drill towards the first bone portion; and a second guide sleeve slidably received in the foot portion and comprising a second aperture configured to guide the drill towards the second bone portion;

wherein the first guide sleeve and the second guide sleeve are independently spring-loaded relative to the foot portion;

using the drill guide and a drill to create a first plurality of holes in the first bone portion and a second plurality of holes in the second bone portion;

using the drill guide and a first drill pin to drive the first drill pin into the first bone portion;

using the drill guide and a second drill pin to drive the second drill pin into the second bone portion;

withdrawing the drill guide and leaving the first drill pin in the first bone portion and the second drill pin in the second bone portion;

guiding the inserter and the compression staple over the first drill pin and the second drill pin;

inserting the compression staple into the first bone portion and the second bone portion;

actuating the inserter to release the compression staple;

withdrawing the inserter; and removing the first drill pin and the second drill pin.

8. The method of claim 7, further comprising guiding an impactor over the first drill pin and the second drill pin and using the impactor to assess a first surface of the first bone portion and a second surface of the second bone portion to determine if the compression staple is insertable to be flush with the first surface and the second surface.

9. The method of claim 7, further comprising guiding an impactor over the first drill pin and the second drill pin to impact the compression staple flush with a first surface of the first bone portion and a second surface of the second bone portion.

10. The method of claim 7, wherein the inserter is configured to releasably engage the compression staple and comprises:

a stationary jaw comprising a pair of first hooks configured to engage the compression staple;

a moveable jaw comprising a pair of second hooks configured to engage the compression staple;

a closed configuration wherein the stationary jaw is spaced apart from the moveable jaw a first distance; and an open configuration wherein the stationary jaw is spaced apart from the moveable jaw a second distance greater than the first distance;

wherein:

the compression staple is captive within the inserter with the inserter in the closed configuration;

the compression staple is releasable from the inserter with the inserter in the open configuration; and the stationary jaw and the moveable jaw remain parallel between the closed configuration and the open configuration.

11. The method of claim 7, wherein the first bone portion and the second bone portion are separated by a joint or a fracture.

12. The method of claim 11, wherein creating the first plurality of holes in the first bone portion comprises creating the first plurality of holes generally parallel to the joint or the fracture, and creating the second plurality of holes in the second bone portion comprises creating the second plurality of holes generally parallel to the joint or the fracture.

13. A method of bone fixation using a compression staple system, the method comprising:

loading a compression staple into an inserter; wherein the inserter is configured to releasably engage the compression staple and comprises:

a stationary jaw comprising a pair of first hooks configured to engage the compression staple;

a moveable jaw comprising a pair of second hooks configured to engage the compression staple;

a closed configuration wherein the stationary jaw is spaced apart from the moveable jaw a first distance; and an open configuration wherein the stationary jaw is spaced apart from the moveable jaw a second distance greater than the first distance;

wherein:

the compression staple is captive within the inserter with the inserter in the closed configuration;

the compression staple is releasable from the inserter with the inserter in the open configuration; and the stationary jaw and the moveable jaw remain parallel between the closed configuration and the open configuration;

using a drill guide and a drill to create a first hole in a first bone portion, a second hole in the first bone portion, a third hole in a second bone portion, and a fourth hole in the second bone portion, wherein the drill guide comprises:

a handle;

a foot portion coupled to the handle;

a first guide sleeve captively and slidably received in the foot portion, the first guide sleeve comprising:

a first aperture configured to guide the drill along a first trajectory; and a second aperture configured to guide the drill along a second trajectory; and a second guide sleeve captively and slidably received in the foot portion and spaced apart from the first guide sleeve, the second guide sleeve comprising:

a third aperture configured to guide the drill along a third trajectory; and a fourth aperture configured to guide the drill along a fourth trajectory;

wherein, the first trajectory, the second trajectory, the third trajectory, and the fourth trajectory are all parallel;

inserting the compression staple into the first hole, the second hole, the third hole, and the fourth hole;

actuating the inserter to release the compression staple; and withdrawing the inserter.

14. The method of claim 13, further comprising:

using the drill guide and a second drill to create a fifth hole in the first bone portion using a fifth aperture in the drill guide, the fifth aperture comprising a fifth trajectory; and using the drill guide and a third drill to create a sixth hole in the second bone portion using a sixth aperture in the drill guide, the sixth aperture comprising a sixth trajectory;

wherein the fifth trajectory and the sixth trajectory are parallel to the first trajectory.

15. The method of claim 13, further comprising guiding an impactor over a first drill pin inserted into the first bone portion and a second drill pin inserted into the second bone portion and using the impactor to assess a first surface of the first bone portion and a second surface of the second bone portion to determine if the compression staple is insertable to be flush with the first surface and the second surface.

16. The method of claim 13, further comprising guiding an impactor over a first drill pin inserted into the first bone portion and a second drill pin inserted into the second bone portion to impact the compression staple flush with a first surface of the first bone portion and a second surface of the second bone portion.

17. The method of claim 13, the method further comprises, with the first bone portion and the second bone portion separated by a joint or a fracture, creating the first hole in the first bone portion comprises creating the first hole generally parallel to the joint or the fracture, and creating the third hole in the second bone portion comprises creating the third hole generally parallel to the joint or the fracture.

* * * * *